(12) United States Patent
Christie et al.

(10) Patent No.: US 9,492,272 B2
(45) Date of Patent: Nov. 15, 2016

(54) MASKED INTRAOCULAR IMPLANTS AND LENSES

(75) Inventors: Bruce A. Christie, Claremont, CA (US); Alexei N. Kosmynine, Aliso Viejo, CA (US)

(73) Assignee: AcuFocus, Inc., Irvine, CA (US)

( * ) Notice: Subject to any disclaimer, the term of this patent is extended or adjusted under 35 U.S.C. 154(b) by 447 days.

(21) Appl. No.: 12/856,492

(22) Filed: Aug. 13, 2010

(65) Prior Publication Data

US 2011/0040376 A1    Feb. 17, 2011

Related U.S. Application Data

(60) Provisional application No. 61/233,794, filed on Aug. 13, 2009, provisional application No. 61/233,804, filed on Aug. 13, 2009.

(51) Int. Cl.
*A61F 2/16* (2006.01)
*B29D 11/02* (2006.01)
*B29D 11/00* (2006.01)

(52) U.S. Cl.
CPC ............... *A61F 2/16* (2013.01); *A61F 2/1613* (2013.01); *A61F 2/1659* (2013.01); *B29D 11/0048* (2013.01); *B29D 11/023* (2013.01); *A61F 2002/1681* (2013.01); *A61F 2210/0076* (2013.01); *A61F 2250/0053* (2013.01);
(Continued)

(58) Field of Classification Search
CPC .. A61F 2/1613; A61F 2/1616; A61F 2/1659; A61F 2/1637–2/1645
USPC ............................... 623/6.16–6.17, 6.27–6.28
See application file for complete search history.

(56) References Cited

U.S. PATENT DOCUMENTS

| 564,518 A | 7/1896 | Heilborn |
| 1,206,132 A | 11/1916 | Otte |
| 1,959,915 A | 5/1934 | Guthrie |

(Continued)

FOREIGN PATENT DOCUMENTS

| AU | 2004201751 | 5/2004 |
| CN | 1875895 | 12/2006 |

(Continued)

OTHER PUBLICATIONS

Accommodation Responses and Ageing. Heron et al. IOVS, Nov. 1999, vol. 40, No. 12, pp. 2872-2883.
(Continued)

*Primary Examiner* — Paul Prebilic
(74) *Attorney, Agent, or Firm* — Knobbe Martens Olson & Bear LLP

(57) ABSTRACT

Intraocular implants and methods of making intraocular implants are provided. The intraocular implants can improve the vision of a patient, such as by increasing the depth of focus of an eye of a patient. In particular, the intraocular implants can include a mask having an annular portion with a relatively low visible light transmission surrounding a relatively high transmission central portion such as a clear lens or aperture. This construct is adapted to provide an annular mask with a small aperture for light to pass through to the retina to increase depth of focus. The intraocular implant may have an optical power for refractive correction. The intraocular implant may be implanted in any location along the optical pathway in the eye, e.g., as an implant in the anterior or posterior chamber.

29 Claims, 64 Drawing Sheets

(52) U.S. Cl.
CPC *A61F2250/0058* (2013.01); *A61F 2250/0098* (2013.01)

(56) References Cited

U.S. PATENT DOCUMENTS

| | | | |
|---|---|---|---|
| 2,129,305 A | 9/1938 | Feinbloom | |
| 2,350,421 A | 6/1944 | Schoder et al. | |
| 2,470,927 A | 5/1949 | Hale, Jr. | |
| 2,714,721 A | 8/1955 | Stone, Jr. | |
| 3,034,403 A | 5/1962 | Neefe | |
| 3,270,099 A | 8/1966 | Camp | |
| 3,339,997 A | 9/1967 | Wesley | |
| 3,458,870 A | 8/1969 | Stone, Jr. | |
| 3,507,566 A | 4/1970 | Knapp | |
| 3,578,850 A | 5/1971 | Grant | |
| 3,600,098 A | 8/1971 | Mohrman | |
| 3,726,587 A | 4/1973 | Kendall | |
| 3,776,230 A | 12/1973 | Neefe | |
| 3,794,414 A | 2/1974 | Wesley | |
| 3,852,032 A | 12/1974 | Urbach | |
| 3,877,502 A | 4/1975 | Hunckler | |
| 3,996,627 A * | 12/1976 | Deeg et al. | 623/6.56 |
| 4,010,496 A | 3/1977 | Neefe | |
| 4,073,015 A | 2/1978 | Peyman | |
| 4,099,529 A | 7/1978 | Peyman | |
| 4,104,338 A | 8/1978 | Guerrieri | |
| 4,116,439 A | 9/1978 | Chavarria et al. | |
| 4,138,191 A | 2/1979 | Peyman | |
| 4,191,195 A | 3/1980 | Miller | |
| 4,210,391 A * | 7/1980 | Cohen | 351/159.39 |
| 4,272,191 A | 6/1981 | Bergkvist | |
| 4,298,996 A | 11/1981 | Barnet | |
| 4,312,575 A | 1/1982 | Peyman et al. | |
| 4,340,283 A * | 7/1982 | Cohen | 351/159.41 |
| 4,367,949 A | 1/1983 | Lavering | |
| 4,402,579 A | 9/1983 | Poler | |
| 4,402,681 A | 9/1983 | Haas et al. | |
| 4,423,728 A | 1/1984 | Lieberman | |
| 4,435,050 A | 3/1984 | Poler | |
| 4,450,593 A | 5/1984 | Poler | |
| 4,485,499 A | 12/1984 | Castleman | |
| 4,505,855 A | 3/1985 | Bruns et al. | |
| 4,528,311 A | 7/1985 | Beard et al. | |
| 4,536,240 A | 8/1985 | Winn | |
| 4,547,914 A | 10/1985 | Castleman | |
| 4,547,915 A | 10/1985 | Castleman | |
| 4,563,565 A | 1/1986 | Kampfer et al. | |
| 4,575,373 A | 3/1986 | Johnson | |
| 4,575,915 A | 3/1986 | Clark et al. | |
| 4,576,453 A | 3/1986 | Borowsky | |
| 4,607,617 A | 8/1986 | Choyce | |
| 4,612,012 A | 9/1986 | White | |
| 4,615,702 A | 10/1986 | Koziol et al. | |
| 4,617,023 A | 10/1986 | Peyman | |
| 4,624,669 A | 11/1986 | Grendahl | |
| 4,633,866 A | 1/1987 | Peyman et al. | |
| 4,636,049 A | 1/1987 | Blaker | |
| 4,636,211 A | 1/1987 | Nielsen et al. | |
| 4,636,212 A | 1/1987 | Posin et al. | |
| 4,637,697 A | 1/1987 | Freeman | |
| 4,639,105 A | 1/1987 | Neefe | |
| 4,641,934 A | 2/1987 | Freeman | |
| 4,642,112 A | 2/1987 | Freeman | |
| 4,646,720 A | 3/1987 | Peyman | |
| 4,655,774 A | 4/1987 | Choyce | |
| 4,665,913 A | 5/1987 | Esperance, Jr. | |
| 4,666,446 A | 5/1987 | Koziol et al. | |
| 4,669,466 A | 6/1987 | L'Esperance | |
| 4,669,834 A | 6/1987 | Richter | |
| 4,674,503 A | 6/1987 | Peyman et al. | |
| 4,676,790 A | 6/1987 | Kern | |
| 4,676,791 A | 6/1987 | Le Master et al. | |
| 4,678,422 A | 7/1987 | York | |
| 4,685,922 A | 8/1987 | Peyman | |
| 4,701,038 A | 10/1987 | Neefe | |
| 4,702,865 A | 10/1987 | Koziol et al. | |
| 4,704,016 A | 11/1987 | de Carle | |
| 4,710,003 A | 12/1987 | Masuda et al. | |
| 4,713,446 A | 12/1987 | DeVore et al. | |
| 4,715,858 A | 12/1987 | Lindstrom | |
| 4,729,373 A | 3/1988 | Peyman | |
| 4,753,654 A | 6/1988 | Posin et al. | |
| 4,767,647 A | 8/1988 | Bree | |
| 4,779,973 A | 10/1988 | Miller et al. | |
| 4,785,796 A | 11/1988 | Mattson | |
| 4,795,462 A * | 1/1989 | Grendahl | 623/6.28 |
| 4,798,608 A * | 1/1989 | Grendahl | 623/6.28 |
| 4,799,784 A | 1/1989 | Safir | |
| 4,799,931 A | 1/1989 | Lindstrom | |
| 4,806,382 A | 2/1989 | Goldberg et al. | |
| 4,807,623 A | 2/1989 | Lieberman | |
| 4,808,181 A | 2/1989 | Kelman | |
| 4,813,955 A | 3/1989 | Achatz et al. | |
| 4,814,050 A | 3/1989 | McGraw et al. | |
| 4,817,789 A | 4/1989 | Paul | |
| 4,838,266 A | 6/1989 | Koziol et al. | |
| 4,840,175 A | 6/1989 | Peyman | |
| 4,842,599 A | 6/1989 | Bronstein | |
| 4,851,003 A | 7/1989 | Lindstrom | |
| 4,863,466 A * | 9/1989 | Schlegel | 623/6.44 |
| 4,865,601 A | 9/1989 | Caldwell et al. | |
| 4,869,587 A | 9/1989 | Breger | |
| 4,878,910 A | 11/1989 | Koziol et al. | |
| 4,881,860 A | 11/1989 | Kanazawa | |
| 4,881,954 A | 11/1989 | Bikson et al. | |
| 4,890,913 A | 1/1990 | De Carle | |
| 4,891,043 A | 1/1990 | Zeimer et al. | |
| 4,898,461 A | 2/1990 | Portney | |
| 4,903,695 A | 2/1990 | Warner et al. | |
| 4,907,586 A | 3/1990 | Bille et al. | |
| 4,923,297 A | 5/1990 | Arndt | |
| 4,928,815 A | 5/1990 | Paul | |
| 4,932,970 A | 6/1990 | Portney | |
| 4,955,904 A | 9/1990 | Atebara et al. | |
| 4,958,922 A | 9/1990 | Binh et al. | |
| 4,965,545 A | 10/1990 | Johnson | |
| 4,971,432 A | 11/1990 | Koeniger | |
| 4,976,732 A * | 12/1990 | Vorosmarthy | 623/6.17 |
| 4,983,181 A | 1/1991 | Civerchia | |
| 4,985,559 A | 1/1991 | Goldberg et al. | |
| 4,990,165 A | 2/1991 | Bikson et al. | |
| 4,994,080 A | 2/1991 | Shepard | |
| 4,997,268 A | 3/1991 | Dauvergne | |
| 5,002,571 A | 3/1991 | O'Donnell, Jr. | |
| 5,013,319 A | 5/1991 | Davis | |
| 5,019,097 A | 5/1991 | Knight et al. | |
| 5,026,393 A | 6/1991 | Mackool | |
| 5,030,230 A | 7/1991 | White | |
| 5,041,133 A | 8/1991 | Sayano et al. | |
| 5,055,602 A | 10/1991 | Melpolder | |
| 5,061,914 A | 10/1991 | Busch et al. | |
| 5,067,961 A | 11/1991 | Kelman et al. | |
| 5,076,684 A | 12/1991 | Simpson et al. | |
| 5,087,015 A | 2/1992 | Galley | |
| 5,089,022 A | 2/1992 | Koester et al. | |
| 5,089,024 A | 2/1992 | Christie et al. | |
| 5,090,955 A | 2/1992 | Simon | |
| 5,094,521 A | 3/1992 | Jolson et al. | |
| 5,098,443 A | 3/1992 | Parel et al. | |
| 5,098,444 A | 3/1992 | Feaster | |
| 5,104,957 A | 4/1992 | Kelman et al. | |
| 5,108,169 A | 4/1992 | Mandell | |
| 5,108,428 A | 4/1992 | Capecchi et al. | |
| 5,112,328 A | 5/1992 | Taboada et al. | |
| 5,112,350 A | 5/1992 | Civerchia et al. | |
| 5,116,111 A | 5/1992 | Simpson et al. | |
| 5,119,555 A | 6/1992 | Johnson | |
| 5,120,120 A * | 6/1992 | Cohen | 351/159.49 |
| 5,120,121 A | 6/1992 | Rawlings et al. | |
| 5,123,921 A | 6/1992 | Werblin et al. | |
| 5,133,745 A | 7/1992 | Falcetta et al. | |
| 5,137,441 A | 8/1992 | Fogarty | |
| 5,147,395 A | 9/1992 | Willis | |
| 5,149,331 A | 9/1992 | Ferdman et al. | |

(56) References Cited

U.S. PATENT DOCUMENTS

| | | | |
|---|---|---|---|
| 5,152,789 A | 10/1992 | Willis | |
| 5,160,463 A | 11/1992 | Evans et al. | |
| 5,165,897 A | 11/1992 | Johnson | |
| 5,166,712 A | 11/1992 | Portney | |
| 5,171,318 A | 12/1992 | Gibson et al. | |
| 5,185,107 A | 2/1993 | Blake | |
| 5,185,152 A | 2/1993 | Peyman | |
| 5,188,494 A | 2/1993 | Hatin | |
| 5,192,316 A | 3/1993 | Ting | |
| 5,192,318 A | 3/1993 | Schneider et al. | |
| 5,196,026 A | 3/1993 | Barrett et al. | |
| 5,213,749 A | 5/1993 | Huss et al. | |
| 5,219,844 A | 6/1993 | Peyman et al. | |
| 5,225,858 A | 7/1993 | Portney | |
| 5,239,066 A | 8/1993 | Falkow et al. | |
| 5,245,367 A | 9/1993 | Miller et al. | |
| 5,245,738 A | 9/1993 | Johnson | |
| 5,258,412 A | 11/1993 | Peyman et al. | |
| 5,260,727 A * | 11/1993 | Oksman et al. | 351/159.03 |
| 5,261,997 A | 11/1993 | Inselmann | |
| 5,266,241 A | 11/1993 | Parekh | |
| 5,269,795 A | 12/1993 | Arnott | |
| 5,269,812 A | 12/1993 | White | |
| 5,270,744 A | 12/1993 | Portney | |
| 5,274,404 A | 12/1993 | Michael | |
| 5,282,971 A | 2/1994 | Degen et al. | |
| 5,288,436 A | 2/1994 | Liu et al. | |
| 5,292,514 A | 3/1994 | Capecchi et al. | |
| 5,296,881 A | 3/1994 | Freeman | |
| 5,300,116 A | 4/1994 | Chirila et al. | |
| 5,302,978 A | 4/1994 | Evans et al. | |
| 5,306,297 A | 4/1994 | Rheinish et al. | |
| 5,310,654 A | 5/1994 | Isberg et al. | |
| 5,312,330 A | 5/1994 | Klopotek | |
| 5,312,393 A | 5/1994 | Mastel | |
| 5,314,439 A | 5/1994 | Sugita | |
| 5,314,961 A | 5/1994 | Anton et al. | |
| 5,315,344 A | 5/1994 | Clark et al. | |
| 5,318,047 A | 6/1994 | Davenport et al. | |
| 5,322,649 A | 6/1994 | Rheinish et al. | |
| 5,323,788 A | 6/1994 | Silvestrini et al. | |
| 5,325,880 A | 7/1994 | Johnson et al. | |
| 5,332,802 A | 7/1994 | Kelman et al. | |
| 5,336,261 A | 8/1994 | Barrett et al. | |
| 5,346,689 A | 9/1994 | Peyman et al. | |
| 5,354,331 A | 10/1994 | Schachar | |
| 5,358,520 A | 10/1994 | Patel | |
| 5,366,499 A | 11/1994 | Py | |
| 5,372,580 A | 12/1994 | Simon et al. | |
| 5,374,272 A | 12/1994 | Arpa et al. | |
| D354,566 S | 1/1995 | Donahoo | |
| 5,391,201 A | 2/1995 | Barrett et al. | |
| 5,401,508 A | 3/1995 | Manesis | |
| 5,405,384 A | 4/1995 | Silvestrini | |
| 5,422,424 A | 6/1995 | Selsted et al. | |
| 5,433,745 A | 7/1995 | Graham et al. | |
| 5,434,630 A | 7/1995 | Bransome | |
| 5,437,274 A | 8/1995 | Khoobehi et al. | |
| 5,441,511 A | 8/1995 | Hanna | |
| 5,458,819 A | 10/1995 | Chirila et al. | |
| 5,474,548 A | 12/1995 | Knopp et al. | |
| 5,476,515 A | 12/1995 | Kelman et al. | |
| 5,480,427 A | 1/1996 | Kelman et al. | |
| 5,489,300 A | 2/1996 | Capecchi et al. | |
| 5,505,723 A | 4/1996 | Muller | |
| 5,507,740 A | 4/1996 | O'Donnell, Jr. | |
| 5,516,522 A | 5/1996 | Peyman et al. | |
| 5,522,888 A | 6/1996 | Civerchia | |
| 5,526,178 A | 6/1996 | Goldstein et al. | |
| 5,527,356 A | 6/1996 | Peyman et al. | |
| 5,547,468 A | 8/1996 | Simon et al. | |
| 5,547,473 A | 8/1996 | Peyman | |
| 5,567,365 A | 10/1996 | Weinschenk, III et al. | |
| D375,245 S | 11/1996 | Irving | |
| 5,571,177 A | 11/1996 | Deacon et al. | |
| 5,578,080 A * | 11/1996 | McDonald | A61F 2/16 623/6.17 |
| 5,579,063 A | 11/1996 | Magnante et al. | |
| RE35,421 E | 1/1997 | Ruiz et al. | |
| 5,599,537 A | 2/1997 | Miller, III et al. | |
| 5,603,774 A | 2/1997 | LeBoeuf et al. | |
| 5,605,938 A | 2/1997 | Roufa et al. | |
| 5,607,437 A | 3/1997 | Simon et al. | |
| 5,608,471 A | 3/1997 | Miller | |
| 5,610,719 A | 3/1997 | Allen et al. | |
| 5,624,456 A | 4/1997 | Hellenkamp | |
| 5,627,613 A | 5/1997 | Kaneko | |
| 5,628,794 A | 5/1997 | Lindstrom | |
| 5,628,795 A | 5/1997 | Langerman | |
| 5,628,798 A | 5/1997 | Eggleston et al. | |
| 5,631,243 A | 5/1997 | Kelman et al. | |
| 5,632,773 A | 5/1997 | Graham et al. | |
| 5,647,865 A | 7/1997 | Swinger | |
| 5,653,752 A | 8/1997 | Silvestrini et al. | |
| 5,662,706 A | 9/1997 | Legerton et al. | |
| 5,662,908 A | 9/1997 | Falkow et al. | |
| 5,672,885 A | 9/1997 | Allen et al. | |
| 5,674,724 A | 10/1997 | Miller, III et al. | |
| 5,674,736 A | 10/1997 | Miller, III et al. | |
| 5,693,092 A | 12/1997 | Silvestrini et al. | |
| 5,693,268 A | 12/1997 | Widman et al. | |
| 5,695,983 A | 12/1997 | Miller et al. | |
| 5,697,923 A | 12/1997 | Poler | |
| 5,697,973 A | 12/1997 | Peyman et al. | |
| 5,702,440 A | 12/1997 | Portney | |
| 5,708,049 A | 1/1998 | Katagiri et al. | |
| 5,713,844 A | 2/1998 | Peyman | |
| 5,713,957 A | 2/1998 | Steele et al. | |
| 5,719,656 A | 2/1998 | Bowling | |
| 5,722,971 A | 3/1998 | Peyman | |
| 5,725,575 A | 3/1998 | O'Donnell, Jr. | |
| 5,731,196 A | 3/1998 | Miller, III et al. | |
| 5,731,862 A | 3/1998 | Winkler | |
| 5,733,760 A | 3/1998 | Lu et al. | |
| 5,746,558 A | 5/1998 | Nygren et al. | |
| 5,752,967 A | 5/1998 | Kritzinger et al. | |
| 5,757,458 A | 5/1998 | Miller et al. | |
| 5,769,889 A | 6/1998 | Kelman | |
| 5,771,088 A | 6/1998 | Perrott | |
| 5,771,742 A | 6/1998 | Bokaie et al. | |
| 5,774,202 A | 6/1998 | Abraham et al. | |
| 5,782,911 A | 7/1998 | Herrick | |
| 5,786,883 A | 7/1998 | Miller et al. | |
| 5,800,533 A | 9/1998 | Eggleston et al. | |
| 5,806,530 A | 9/1998 | Herrick | |
| 5,814,680 A | 9/1998 | Imafuku et al. | |
| 5,824,086 A | 10/1998 | Silvestrini | |
| 5,836,313 A | 11/1998 | Perez et al. | |
| 5,837,156 A | 11/1998 | Cumming | |
| 5,840,848 A | 11/1998 | Sturrock et al. | |
| 5,843,105 A | 12/1998 | Mathis et al. | |
| 5,843,186 A | 12/1998 | Christ | |
| 5,855,605 A | 1/1999 | Herrick | |
| 5,858,980 A | 1/1999 | Weiner et al. | |
| 5,861,486 A | 1/1999 | DeVore et al. | |
| 5,863,537 A | 1/1999 | Dalliet et al. | |
| 5,864,128 A | 1/1999 | Plesko | |
| 5,864,378 A | 1/1999 | Portney | |
| 5,870,167 A | 2/1999 | Knopp et al. | |
| 5,874,537 A | 2/1999 | Kelman et al. | |
| 5,895,610 A | 4/1999 | Chang et al. | |
| 5,903,099 A | 5/1999 | Johnson et al. | |
| 5,905,561 A | 5/1999 | Lee et al. | |
| 5,910,537 A | 6/1999 | Feingold et al. | |
| 5,913,898 A | 6/1999 | Feingold et al. | |
| 5,919,185 A | 7/1999 | Peyman | |
| 5,925,294 A | 7/1999 | Shibuya | |
| 5,929,968 A | 7/1999 | Cotie et al. | |
| 5,960,812 A | 10/1999 | Johnson | |
| 5,964,748 A | 10/1999 | Peyman | |
| 5,964,776 A | 10/1999 | Peyman | |
| 5,965,330 A | 10/1999 | Evans et al. | |
| 5,980,040 A | 11/1999 | Xu et al. | |
| 5,997,559 A | 12/1999 | Ziemer | |

(56) References Cited

U.S. PATENT DOCUMENTS

| | | |
|---|---|---|
| 6,010,901 A | 1/2000 | Miller, III et al. |
| 6,024,447 A | 2/2000 | Portney |
| 6,036,957 A | 3/2000 | Weiner et al. |
| 6,063,073 A | 5/2000 | Peyman |
| 6,083,236 A | 7/2000 | Feingold |
| 6,090,141 A | 7/2000 | Lindstrom |
| 6,096,077 A | 8/2000 | Callahan et al. |
| 6,102,946 A | 8/2000 | Nigam |
| 6,106,552 A | 8/2000 | Lacombe et al. |
| 6,106,553 A | 8/2000 | Feingold et al. |
| 6,110,166 A | 8/2000 | Juhasz et al. |
| 6,126,286 A | 10/2000 | Portney |
| 6,138,307 A | 10/2000 | McDonald |
| 6,152,959 A | 11/2000 | Portney |
| 6,161,544 A | 12/2000 | DeVore et al. |
| 6,164,282 A | 12/2000 | Gwon et al. |
| 6,164,777 A | 12/2000 | Li et al. |
| 6,165,189 A | 12/2000 | Ziemer |
| 6,171,336 B1 | 1/2001 | Sawusch |
| 6,176,878 B1 | 1/2001 | Gwon et al. |
| 6,178,593 B1 | 1/2001 | Carlson |
| 6,183,498 B1 | 2/2001 | DeVore et al. |
| 6,197,019 B1 | 3/2001 | Peyman |
| 6,197,057 B1 | 3/2001 | Peyman et al. |
| 6,197,934 B1 | 3/2001 | DeVore et al. |
| 6,201,036 B1 | 3/2001 | Fedorov et al. |
| 6,203,538 B1 | 3/2001 | Peyman |
| 6,204,365 B1 | 3/2001 | DeVore et al. |
| 6,210,005 B1 | 4/2001 | Portney |
| 6,210,401 B1 | 4/2001 | Lai |
| 6,217,571 B1 | 4/2001 | Peyman |
| 6,217,596 B1 | 4/2001 | Farah |
| 6,221,067 B1 | 4/2001 | Peyman |
| 6,221,105 B1 | 4/2001 | Portney |
| 6,228,113 B1 | 5/2001 | Kaufman |
| 6,228,114 B1 | 5/2001 | Lee |
| 6,228,115 B1 | 5/2001 | Hoffmann et al. |
| 6,251,118 B1 | 6/2001 | Proudfoot et al. |
| 6,264,648 B1 | 7/2001 | Peyman |
| 6,277,146 B1 | 8/2001 | Peyman et al. |
| 6,280,470 B1 | 8/2001 | Peyman |
| 6,280,471 B1 | 8/2001 | Peyman |
| 6,283,595 B1 | 9/2001 | Breger |
| 6,302,877 B1 * | 10/2001 | Ruiz ................................ 606/5 |
| 6,304,390 B1 | 10/2001 | Takanashi |
| 6,308,590 B1 | 10/2001 | Berto |
| 6,335,006 B1 | 1/2002 | Miller |
| 6,335,190 B1 | 1/2002 | Zhou et al. |
| 6,357,875 B1 | 3/2002 | Herrick |
| 6,358,280 B1 | 3/2002 | Herrick |
| 6,361,560 B1 | 3/2002 | Nigam |
| 6,376,153 B2 | 4/2002 | Uchikawa et al. |
| 6,387,379 B1 | 5/2002 | Goldberg et al. |
| 6,391,055 B1 | 5/2002 | Ikada et al. |
| 6,391,230 B1 | 5/2002 | Sarbadhikari |
| 6,403,947 B1 | 6/2002 | Hoyt et al. |
| 6,406,494 B1 | 6/2002 | Laguette et al. |
| 6,416,179 B1 | 7/2002 | Lieberman et al. |
| 6,419,697 B1 | 7/2002 | Kelman |
| 6,423,093 B1 | 7/2002 | Hicks et al. |
| 6,425,917 B1 | 7/2002 | Blake |
| 6,432,246 B1 | 8/2002 | Blake |
| 6,436,092 B1 | 8/2002 | Peyman |
| 6,457,826 B1 | 10/2002 | Lett |
| 6,458,141 B1 | 10/2002 | Peyman |
| 6,461,384 B1 | 10/2002 | Hoffmann et al. |
| 6,470,108 B1 | 10/2002 | Johnson |
| 6,488,707 B1 | 12/2002 | Callahan et al. |
| 6,491,637 B2 | 12/2002 | Foster et al. |
| 6,494,910 B1 | 12/2002 | Ganem et al. |
| 6,497,700 B1 | 12/2002 | LaHaye |
| 6,503,276 B2 | 1/2003 | Lang et al. |
| 6,515,006 B2 | 2/2003 | Horn |
| 6,527,389 B2 | 3/2003 | Portney |
| 6,533,905 B2 | 3/2003 | Johnson et al. |
| 6,536,899 B1 | 3/2003 | Fiala |
| 6,551,307 B2 | 4/2003 | Peyman |
| 6,554,424 B1 | 4/2003 | Miller et al. |
| 6,554,860 B2 | 4/2003 | Hoffmann et al. |
| 6,555,103 B2 | 4/2003 | Leukel et al. |
| 6,569,199 B1 | 5/2003 | Dotan et al. |
| 6,575,573 B2 | 6/2003 | Lai et al. |
| 6,581,993 B2 | 6/2003 | Nigam |
| RE38,193 E | 7/2003 | Bowling |
| 6,588,022 B1 | 7/2003 | Anders et al. |
| 6,588,902 B2 | 7/2003 | Isogai |
| 6,589,280 B1 | 7/2003 | Koziol |
| 6,592,621 B1 | 7/2003 | Domino |
| 6,599,305 B1 | 7/2003 | Feingold |
| 6,607,527 B1 | 8/2003 | Ruiz et al. |
| 6,607,556 B1 | 8/2003 | Nigam |
| 6,613,088 B1 | 9/2003 | Babizhayev |
| 6,614,570 B2 | 9/2003 | Johnson et al. |
| 6,620,634 B2 | 9/2003 | Johnson et al. |
| 6,623,497 B1 | 9/2003 | Feingold |
| 6,623,522 B2 | 9/2003 | Nigam |
| 6,624,730 B2 | 9/2003 | Johnson et al. |
| 6,626,941 B2 | 9/2003 | Nigam |
| 6,632,244 B1 | 10/2003 | Nigam |
| 6,638,304 B2 | 10/2003 | Azar |
| 6,649,722 B2 | 11/2003 | Rosenzweig et al. |
| 6,655,804 B2 | 12/2003 | Streibig |
| 6,663,668 B1 | 12/2003 | Chaouk et al. |
| 6,669,795 B2 | 12/2003 | Johnson et al. |
| 6,673,112 B2 | 1/2004 | Nigam |
| 6,692,126 B1 | 2/2004 | Xie et al. |
| 6,702,807 B2 | 3/2004 | Peyman |
| 6,726,322 B2 | 4/2004 | Andino et al. |
| 6,729,599 B2 | 5/2004 | Johnson |
| 6,740,116 B2 | 5/2004 | Morcher |
| 6,742,761 B2 | 6/2004 | Johnson et al. |
| 6,746,890 B2 | 6/2004 | Gupta et al. |
| 6,755,858 B1 | 6/2004 | White |
| 6,786,926 B2 | 9/2004 | Peyman |
| 6,790,298 B2 | 9/2004 | Johnson et al. |
| 6,811,256 B1 | 11/2004 | Becherer et al. |
| 6,849,090 B2 | 2/2005 | Nigam |
| 6,855,163 B2 | 2/2005 | Peyman |
| 6,874,886 B2 | 4/2005 | Miller et al. |
| 6,899,424 B2 | 5/2005 | Miller et al. |
| 6,949,093 B1 | 9/2005 | Peyman |
| 6,951,556 B2 | 10/2005 | Epstein |
| 6,966,648 B2 | 11/2005 | Miller et al. |
| 6,976,997 B2 | 12/2005 | Noolandi et al. |
| 6,989,008 B2 | 1/2006 | Peyman |
| 7,001,374 B2 | 2/2006 | Peyman |
| 7,008,447 B2 | 3/2006 | Koziol |
| 7,025,455 B2 | 4/2006 | Roffman |
| 7,061,693 B2 | 6/2006 | Zalevsky |
| 7,099,057 B2 | 8/2006 | Parker et al. |
| 7,207,998 B2 | 4/2007 | Feingold |
| 7,276,080 B2 | 10/2007 | Murakami et al. |
| 7,287,852 B2 | 10/2007 | Fiala |
| 7,364,674 B1 | 4/2008 | Hoover |
| 7,399,811 B2 | 7/2008 | Mentak et al. |
| 7,404,637 B2 | 7/2008 | Miller et al. |
| 7,404,638 B2 * | 7/2008 | Miller et al. ............. 351/159.75 |
| 7,446,157 B2 | 11/2008 | Mentak et al. |
| 7,455,404 B2 | 11/2008 | Bandhauer et al. |
| 7,455,691 B2 | 11/2008 | Feingold et al. |
| 7,462,194 B1 | 12/2008 | Blake |
| 7,491,350 B2 | 2/2009 | Silvestrini |
| 7,497,866 B2 | 3/2009 | Perez |
| 7,628,810 B2 | 12/2009 | Christie et al. |
| 7,641,337 B2 | 1/2010 | Altmann |
| 7,645,291 B2 | 1/2010 | Ross et al. |
| 7,645,299 B2 | 1/2010 | Koziol |
| 7,745,555 B2 | 6/2010 | Mentak et al. |
| 7,828,844 B2 | 11/2010 | Marmo et al. |
| 7,842,367 B2 | 11/2010 | Mentak |
| 7,976,577 B2 | 7/2011 | Silvestrini |
| D645,337 S | 9/2011 | Hsu et al. |
| 8,043,371 B2 | 10/2011 | Paul et al. |
| 8,048,972 B2 | 11/2011 | Mentak et al. |

(56) References Cited

U.S. PATENT DOCUMENTS

| | | |
|---|---|---|
| 8,079,706 B2 | 12/2011 | Silvestrini et al. |
| D656,526 S | 3/2012 | Christie et al. |
| 8,241,354 B2 * | 8/2012 | Hong .................. A61F 2/1613 623/6.27 |
| 8,287,592 B2 | 10/2012 | Silvestrini |
| 8,343,215 B2 | 1/2013 | Miller et al. |
| 8,349,006 B2 | 1/2013 | Zhao et al. |
| D681,086 S | 4/2013 | Christie et al. |
| 8,420,753 B2 | 4/2013 | Mentak et al. |
| 8,460,374 B2 | 6/2013 | Christie et al. |
| 8,568,478 B2 | 10/2013 | Zickler et al. |
| 8,604,098 B2 | 12/2013 | Boydston et al. |
| 8,740,978 B2 | 6/2014 | Weeber et al. |
| 8,752,958 B2 | 6/2014 | Miller et al. |
| 8,858,624 B2 | 10/2014 | Christie et al. |
| 8,864,824 B2 | 10/2014 | Silvestrini et al. |
| 9,005,281 B2 | 4/2015 | Christie et al. |
| 9,138,142 B2 | 9/2015 | Christie et al. |
| 9,204,962 B2 | 12/2015 | Silvestrini |
| 2001/0004702 A1 | 6/2001 | Peyman |
| 2001/0027314 A1 | 10/2001 | Peyman |
| 2001/0034516 A1 | 10/2001 | Peyman |
| 2001/0047203 A1 | 11/2001 | Dalton et al. |
| 2001/0050750 A1 | 12/2001 | Breger |
| 2002/0010510 A1 | 1/2002 | Silvestrini |
| 2002/0028330 A1 | 3/2002 | Patel et al. |
| 2002/0055753 A1 | 5/2002 | Silvestrini |
| 2002/0057148 A1 | 5/2002 | Johnson et al. |
| 2002/0075447 A1 | 6/2002 | Andino et al. |
| 2002/0082288 A1 | 6/2002 | Horn |
| 2002/0107337 A1 | 8/2002 | Rosenzweig et al. |
| 2002/0107566 A1 | 8/2002 | Nigam |
| 2002/0111677 A1 | 8/2002 | Nigam |
| 2002/0120329 A1 * | 8/2002 | Lang et al. .................. 623/6.4 |
| 2002/0128710 A1 | 9/2002 | Eggleston |
| 2002/0167640 A1 | 11/2002 | Francis et al. |
| 2002/0169491 A1 | 11/2002 | Foster et al. |
| 2002/0173846 A1 | 11/2002 | Blake et al. |
| 2002/0188351 A1 | 12/2002 | Laguette |
| 2002/0196409 A1 | 12/2002 | Jani |
| 2003/0002994 A1 | 1/2003 | Johnson et al. |
| 2003/0007122 A1 | 1/2003 | Streibig |
| 2003/0014042 A1 | 1/2003 | Juhasz et al. |
| 2003/0014107 A1 | 1/2003 | Reynard |
| 2003/0033013 A1 | 2/2003 | Callahan et al. |
| 2003/0045930 A1 | 3/2003 | Nguyen |
| 2003/0055497 A1 | 3/2003 | Hicks et al. |
| 2003/0071893 A1 | 4/2003 | Miller et al. |
| 2003/0078655 A1 | 4/2003 | Callahan et al. |
| 2003/0088313 A1 | 5/2003 | Nigam |
| 2003/0093083 A1 | 5/2003 | Peyman |
| 2003/0105521 A1 | 6/2003 | Perez |
| 2003/0127318 A1 | 7/2003 | Johnson et al. |
| 2003/0135272 A1 | 7/2003 | Brady et al. |
| 2003/0149480 A1 | 8/2003 | Shadduck |
| 2003/0204258 A1 | 10/2003 | Graham et al. |
| 2003/0216763 A1 | 11/2003 | Patel |
| 2003/0220653 A1 | 11/2003 | Perez |
| 2004/0014253 A1 | 1/2004 | Gupta et al. |
| 2004/0015234 A1 | 1/2004 | Peyman |
| 2004/0019379 A1 | 1/2004 | Glick et al. |
| 2004/0047014 A1 | 3/2004 | Parker et al. |
| 2004/0056371 A1 | 3/2004 | Liao et al. |
| 2004/0068317 A1 | 4/2004 | Knight |
| 2004/0078075 A1 | 4/2004 | Koziol |
| 2004/0080239 A1 | 4/2004 | Gupta et al. |
| 2004/0106929 A1 | 6/2004 | Masket |
| 2004/0243231 A1 | 12/2004 | Koziol |
| 2005/0027355 A1 | 2/2005 | Murakami et al. |
| 2005/0031697 A1 | 2/2005 | Vehige et al. |
| 2005/0033420 A1 | 2/2005 | Christie et al. |
| 2005/0046794 A1 | 3/2005 | Silvestrini et al. |
| 2005/0049621 A1 | 3/2005 | Feingold et al. |
| 2005/0080485 A1 | 4/2005 | Nigam |
| 2005/0090895 A1 | 4/2005 | Peyman |
| 2005/0119738 A1 | 6/2005 | Nigam |
| 2005/0124983 A1 | 6/2005 | Frey et al. |
| 2005/0137703 A1 | 6/2005 | Chen |
| 2005/0143751 A1 | 6/2005 | Makker et al. |
| 2005/0143812 A1 | 6/2005 | Paul et al. |
| 2005/0182488 A1 | 8/2005 | Peyman |
| 2005/0187621 A1 | 8/2005 | Brady |
| 2005/0246019 A1 | 11/2005 | Blake et al. |
| 2005/0288784 A1 | 12/2005 | Peyman |
| 2006/0064077 A1 | 3/2006 | Peyman |
| 2006/0079959 A1 | 4/2006 | Christie et al. |
| 2006/0079960 A1 | 4/2006 | Christie et al. |
| 2006/0098162 A1 | 5/2006 | Bandhauer et al. |
| 2006/0113054 A1 | 6/2006 | Silvestrini |
| 2006/0118263 A1 * | 6/2006 | Silvestrini .................. 164/46 |
| 2006/0184243 A1 | 8/2006 | Yilmaz |
| 2006/0203192 A1 * | 9/2006 | Miller et al. .................. 351/163 |
| 2006/0232665 A1 | 10/2006 | Schowengerdt et al. |
| 2006/0235428 A1 | 10/2006 | Silvestrini |
| 2006/0235514 A1 | 10/2006 | Silvestrini |
| 2006/0241751 A1 | 10/2006 | Marmo et al. |
| 2006/0252844 A1 | 11/2006 | Mentak |
| 2006/0265058 A1 | 11/2006 | Silvestrini |
| 2006/0268226 A1 | 11/2006 | Christie et al. |
| 2006/0268227 A1 | 11/2006 | Christie et al. |
| 2006/0268228 A1 | 11/2006 | Christie et al. |
| 2006/0268229 A1 | 11/2006 | Silvestrini et al. |
| 2006/0270946 A1 | 11/2006 | Silvestrini et al. |
| 2006/0271026 A1 | 11/2006 | Silvestrini et al. |
| 2006/0271027 A1 | 11/2006 | Silvestrini et al. |
| 2006/0271176 A1 | 11/2006 | Christie et al. |
| 2006/0271177 A1 | 11/2006 | Christie et al. |
| 2006/0271178 A1 | 11/2006 | Christie et al. |
| 2006/0271179 A1 | 11/2006 | Christie et al. |
| 2006/0271180 A1 | 11/2006 | Christie et al. |
| 2006/0271181 A1 | 11/2006 | Christie et al. |
| 2006/0271182 A1 | 11/2006 | Christie et al. |
| 2006/0271183 A1 | 11/2006 | Christie et al. |
| 2006/0271184 A1 | 11/2006 | Silvestrini |
| 2006/0271185 A1 | 11/2006 | Silvestrini |
| 2006/0274264 A1 | 12/2006 | Christie et al. |
| 2006/0274265 A1 | 12/2006 | Christie et al. |
| 2007/0016234 A1 | 1/2007 | Daxer |
| 2007/0032866 A1 | 2/2007 | Portney |
| 2007/0091472 A1 | 4/2007 | Alkemper et al. |
| 2007/0092592 A1 | 4/2007 | Chiang |
| 2007/0129797 A1 | 6/2007 | Lang et al. |
| 2007/0219542 A1 | 9/2007 | Yahagi |
| 2007/0225691 A1 | 9/2007 | Silvestrini et al. |
| 2008/0033546 A1 | 2/2008 | Liang |
| 2008/0077238 A1 * | 3/2008 | Deacon et al. .............. 623/6.16 |
| 2008/0100921 A1 | 5/2008 | Nishikawa |
| 2008/0125862 A1 | 5/2008 | Blake |
| 2008/0151183 A1 | 6/2008 | Altmann |
| 2008/0212030 A1 | 9/2008 | Bentley et al. |
| 2008/0221674 A1 | 9/2008 | Blum et al. |
| 2008/0255663 A1 | 10/2008 | Akpek et al. |
| 2008/0269884 A1 | 10/2008 | Vannoy |
| 2008/0306587 A1 | 12/2008 | Your |
| 2009/0012505 A1 | 1/2009 | Chernyak |
| 2009/0021692 A1 | 1/2009 | Miller et al. |
| 2009/0059168 A1 | 3/2009 | Miller et al. |
| 2009/0069817 A1 | 3/2009 | Peyman |
| 2009/0171458 A1 | 7/2009 | Kellan et al. |
| 2009/0204207 A1 | 8/2009 | Blum et al. |
| 2009/0222086 A1 | 9/2009 | Lui et al. |
| 2009/0234448 A1 | 9/2009 | Weeber et al. |
| 2009/0306773 A1 | 12/2009 | Silversrini et al. |
| 2010/0082100 A1 | 4/2010 | Mikawa |
| 2010/0312336 A1 * | 12/2010 | Hong et al. .................. 623/6.27 |
| 2011/0040376 A1 | 2/2011 | Christie et al. |
| 2011/0125261 A1 | 5/2011 | Portney |
| 2011/0172675 A1 | 7/2011 | Danta et al. |
| 2011/0251685 A1 | 10/2011 | Chu |
| 2012/0109294 A1 | 5/2012 | Olson |
| 2012/0143325 A1 | 6/2012 | Christie et al. |
| 2012/0203239 A1 | 8/2012 | Vukich et al. |
| 2012/0245683 A1 | 9/2012 | Christie et al. |
| 2012/0310338 A1 | 12/2012 | Christie et al. |

(56) References Cited

U.S. PATENT DOCUMENTS

| | | |
|---|---|---|
| 2013/0053953 A1 | 2/2013 | Silvestrini |
| 2013/0103147 A1 | 4/2013 | Christie et al. |
| 2013/0131795 A1 | 5/2013 | Miller et al. |
| 2013/0238091 A1 | 9/2013 | Danta et al. |
| 2013/0268071 A1 | 10/2013 | Vilupuru et al. |
| 2014/0131905 A1 | 5/2014 | Webb |
| 2014/0264981 A1 | 9/2014 | Reboul et al. |
| 2014/0379078 A1 | 12/2014 | Trindade |
| 2015/0025627 A1 | 1/2015 | Christie et al. |
| 2015/0073549 A1 | 3/2015 | Webb et al. |
| 2015/0366658 A1 | 12/2015 | Christie et al. |
| 2016/0081794 A1 | 3/2016 | Silvestrini |
| 2016/0135947 A1 | 5/2016 | Webb et al. |

FOREIGN PATENT DOCUMENTS

| | | |
|---|---|---|
| CN | 101322663 | 12/2008 |
| DE | 41 34 320 | 4/1992 |
| EP | 0165652 | 12/1985 |
| EP | 0286433 | 10/1988 |
| EP | 0443094 | 8/1991 |
| EP | 0457553 | 11/1991 |
| EP | 1173790 A0 | 1/2002 |
| EP | 1674049 | 6/2006 |
| EP | 1548489 B1 | 8/2006 |
| EP | 2319457 | 5/2011 |
| EP | 2243052 B1 | 9/2011 |
| EP | 2365379 | 9/2011 |
| EP | 2455799 | 5/2012 |
| EP | 2823789 | 1/2015 |
| EP | 2364457 B1 | 8/2015 |
| FR | 369 993 | 1/1907 |
| FR | 2599156 | 5/1988 |
| FR | 2620687 | 3/1989 |
| FR | 2649605 | 1/1991 |
| GB | 1 026 839 | 4/1966 |
| GB | 1276003 | 6/1972 |
| JP | 62167343 A | 7/1987 |
| JP | 63-17096 | 4/1988 |
| JP | 64-002644 | 1/1989 |
| JP | H02-7954 | 1/1990 |
| JP | 03-001857 | 1/1991 |
| JP | 04-158859 | 6/1992 |
| JP | H05-65340 | 9/1993 |
| JP | 6-502782 | 3/1994 |
| JP | 6-509731 | 11/1994 |
| JP | H07-067896 | 3/1995 |
| JP | 07-178125 | 7/1995 |
| JP | 07-265340 | 10/1995 |
| JP | 08-103457 | 4/1996 |
| JP | 09-502542 | 3/1997 |
| JP | H09-502542 | 3/1997 |
| JP | 11-503657 | 8/1997 |
| JP | 04-158859 | 6/1998 |
| JP | 2000-047145 | 2/2000 |
| JP | 2002-14772 | 1/2002 |
| JP | 2002-537895 | 11/2002 |
| JP | 2003-502109 | 1/2003 |
| JP | 2004-510199 | 4/2004 |
| JP | 2004-538034 | 12/2004 |
| JP | 2005-533576 | 11/2005 |
| JP | 2007-516794 | 6/2007 |
| JP | 2007-523720 | 8/2007 |
| JP | 2008-506710 | 3/2008 |
| JP | S59-54527 | 5/2008 |
| KR | 10-0335722 | 5/2002 |
| RU | 2138837 | 9/1999 |
| SU | 1380743 A1 | 3/1998 |
| WO | WO 87/05797 | 10/1987 |
| WO | WO 92/05694 | 4/1992 |
| WO | WO 93/03776 | 3/1993 |
| WO | WO 94/01058 | 1/1994 |
| WO | WO 94/05232 | 3/1994 |
| WO | WO 94/23327 | 10/1994 |
| WO | WO 95/02356 | 1/1995 |
| WO | WO 95/03747 | 2/1995 |
| WO | WO 95/08135 | 3/1995 |
| WO | WO 96/35397 | 11/1996 |
| WO | WO 97/48004 | 12/1997 |
| WO | WO 97/48005 | 12/1997 |
| WO | WO 98/27896 | 7/1998 |
| WO | WO 98/48715 | 11/1998 |
| WO | WO 99/07309 | 2/1999 |
| WO | WO 00/25704 | 5/2000 |
| WO | WO 00/38594 | 7/2000 |
| WO | WO 00/51682 | 9/2000 |
| WO | WO 00/52516 A2 | 9/2000 |
| WO | WO 00/70388 | 11/2000 |
| WO | WO 00/52516 A3 | 1/2001 |
| WO | WO 01/10641 A | 2/2001 |
| WO | WO 01/15779 | 3/2001 |
| WO | WO 01/17460 | 3/2001 |
| WO | WO 01/19364 | 3/2001 |
| WO | WO 01/82815 | 11/2001 |
| WO | WO 01/87189 | 11/2001 |
| WO | WO 02/13881 | 2/2002 |
| WO | WO 02/27388 | 4/2002 |
| WO | WO 02/076320 | 10/2002 |
| WO | WO 02/102241 A2 | 12/2002 |
| WO | WO 03/020177 | 3/2003 |
| WO | WO 03/022168 | 3/2003 |
| WO | WO 03/030763 A1 | 4/2003 |
| WO | WO 03/061518 | 7/2003 |
| WO | WO 2004/014969 | 2/2004 |
| WO | WO 2004/034917 | 4/2004 |
| WO | WO 2004/050132 | 6/2004 |
| WO | WO 2004/105588 A2 | 12/2004 |
| WO | WO 2004/113959 | 12/2004 |
| WO | WO 2005/082265 | 9/2005 |
| WO | WO 2006/020638 | 2/2006 |
| WO | WO 2006/047534 | 5/2006 |
| WO | WO 2006/047698 | 5/2006 |
| WO | WO 2006/060380 | 6/2006 |
| WO | WO 2006/113377 | 10/2006 |
| WO | WO 2006/113411 | 10/2006 |
| WO | WO 2006/113563 | 10/2006 |
| WO | WO 2006/113564 | 10/2006 |
| WO | WO 2007/057734 | 10/2007 |
| WO | WO 2007/133384 | 11/2007 |
| WO | WO 2007/142981 | 12/2007 |
| WO | WO 2008/036671 A1 | 3/2008 |
| WO | WO 2008/102096 | 8/2008 |
| WO | WO 2009/050511 | 4/2009 |
| WO | WO 2009/122409 | 10/2009 |
| WO | WO 2009/140080 | 11/2009 |
| WO | WO 2009/149060 | 12/2009 |
| WO | WO 2010/059214 | 5/2010 |
| WO | WO 2011/020074 | 2/2011 |
| WO | WO 2011/020078 | 2/2011 |
| WO | WO 2011/047076 | 4/2011 |
| WO | WO 2011/069059 | 6/2011 |
| WO | WO 2011/088107 | 7/2011 |
| WO | WO 2013/019871 | 2/2013 |
| WO | WO 2013/082545 | 6/2013 |
| WO | WO 2013/101793 | 7/2013 |
| WO | WO 2013/112589 | 8/2013 |
| WO | WO 2013/123265 | 8/2013 |
| WO | WO 2014/054946 | 4/2014 |
| WO | WO 2014/074610 | 5/2014 |
| WO | WO 2014/158653 | 10/2014 |
| WO | WO 2015/021323 | 2/2015 |
| WO | WO 2015/069927 | 5/2015 |
| WO | WO 2015/073718 | 5/2015 |
| WO | WO 2016/081493 | 5/2016 |

OTHER PUBLICATIONS

Age Changes in the Interactions between the Accommodation and Vergence Systems. Heron et al. Optometry and Vision Science. vol. 78, No. 10, Oct. 2001.

Anterior Ciliary Sclerotomy for Treatment of Presbyopia: A Prospective Controlled Study. Hamilton et al. Ophthalmology, vol. 109, No. 11: Nov. 2002: pp. 1970-1977.

(56) References Cited

OTHER PUBLICATIONS

Brooks, J. et al., Identification of a vimentin-reactive Peptide associated with ocular lens membranes as cytokeratin, Ophthalmic Res., Jan.-Feb. 2003, pp. 8-11, vol. 35.
Can Accommodation be Surgically Restored in Human Presbyopia? Glasser, Adrian. Optometry and Vision Science, vol. 76, No. 9, Sep. 1999.
Choice of Spatial Frequency for Contrast Sensitivity Evaluation After Corneal Refractive Surgery. Montes-Mico et al. Journal of Refractive Surgery, vol. 17: Nov./Dec. 2001: pp. 646-651.
Chow, C., et al., Broadband optical ultrasound sensor with a unique open-cavity structure, J. Biomed. Opt., Jan. 2011, pp. 017001-017001-6, vol. 16.
Clinical Characteristics of Lamellar Channel Deposits After Implementation of Intacs. Ruckhofer et al. J Cataract Refract Surg, vol. 26, Oct. 2000: pp. 1473-1479.
Corneal Topography: The State of the Art, Alignment of Videokeratographs. Mandell et al. Chpt. 2, pp. 17-23, Jan. 1995.
Dynamic retinoscopy and accomodation. Whitefoot et al. Ophthal. Physiol. Opt. vol. 12, Jan. 1992, pp. 8-17.
Eight Years Experience with Permalens Intracorneal Lenses in Nonhuman Primates. Werblin et al. Refractive & Corneal Surgery, vol. 8, Jan./Feb. 1992, pp. 12-21.
Evaluate surgical routine to determine DLK cause, surgeon advises. Piechocki, Michael. Ocular Surgery News: Refractive Surgery, Jan. 1, 2003: p. 14.
Explanation for the observation of isogyres in crystalline lenses viewed between crossed polarizers. Opthal. Physiol. Opt., vol. 13, Apr. 1993, pp. 209-211.
FDA Summary of Safety and Effectiveness Data for XACT Foldable Hydrophopic Acrylic UV Absorving Posterior Chamber Intraocular Lens discussing clinical investigation beginning on May 8, 2002.
Flap Measurements With the Hansatome Microkeratome. Spadea et al. Journal of Refractive Surgery, vol. 18, Mar./Apr. 2002: pp. 149-154.
Gamez, G., et al., Development of a pulsed radio frequency glow discharge for three-dimensional elemental surface imaging. 1. Application to biopolymer analysis, Anal. Chem., Feb. 2007, pp. 1317-1326, vol. 79.
Griffith et al.; "Functional Human Corneal Equivalents Constructed from Cell Lines", SCIENCE, vol. 286, Dec. 10, 1999 pp. 2169-2172.
Hara, T., et al., Accommodative intraocular lens with spring action. Part 1. Design and placement in an excised animal eye, Ophthalmic Surg., Feb. 1990, pp. 128-133, vol. 21.
Hara, T., et al., Ten-year results of anterior chamber fixation of the posterior chamber intraocular lens, Arch. Ophthalmol., Aug. 2004, pp. 1112-1116.
Hayashi, K., et al., Intraocular lens factors that may affect anterior capsule contraction, Ophthalmology, Feb. 2005, pp. 286-292, vol. 112.
Hayashi, K., et al., Comparison of decentration and tilt between one piece and three piece polymethyl methacrylate intraocular lenses, Br. J. Ophthalmol., Apr. 1998, pp. 419-422, vol. 82.
Holes in Clear Lenses Demonstrate a Pinhole Effect. Zacharia et al. Arch Ophthalmol, vol. 106, Apr. 1988, pp. 511-513.
Hybrid diffractive-refractive achromatic spectacle lenses. Charman, W. N. Opthal. Physiol. Opt., vol. 14, Oct. 1994: pp. 389-392.
Izak, A., et al., Loop memory of haptic materials in posterior chamber intraocular lenses, J. Cataract Refract. Surg., Jul. 2002, pp. 1229-1235, vol. 28.
Kimura, W., et al., Comparison of shape recovery ratios in various IOL haptics, Nippon Ganka Gakkai Zasshi, Jun. 1991, pp. 548-555, vol. 95.
Kimura, W., et al., Comparison of shape recovery ratios in various intraocular lens haptics, J. Cataract. Refract. Surg., Nov. 1992, pp. 547-553, vol. 18.
Kimura, W., et al., Comparison of shape recovery ratios of single-piece poly(methyl methacrylate) intraocular lens haptics., J. Cataract. Refract. Surg., Sep. 1993, pp. 635-639, vol. 19.
Ko, A., et al., Seroreactivity against aqueous-soluble and detergent-soluble retinal proteins in posterior uveitis, Arch. Ophthalmol., Apr. 2011, pp. 415-420, vol. 129.
Kocak, N., et al., Intraocular lens haptic fracturing with the neodymium:YAG laser In vitro study, J. Cataract Refract. Surg., Apr. 2006, pp. 662-665, vol. 32.
Lipid Deposits Posterior to Impermeable Intracornel Lenses in Rhesus Monkeys: Clinical, Histochemical, and Ultrastructural Studies. Rodrigues et al. Refractive & Corneal Surgery, vol. 6, Jan./Feb. 1990: DO. 32-37.
Mastel Precision: Fiber Optic Ring Illuminator (Product Nos. 3776 & 4050) U.S. Pat. No. 5312393 User Manual. Rev: A02: Jan. 11, 1995, pp. 1-25.
Mastel Precision: The Ring Light. http://www.mastel.com/ring_light.html. Jul. 28, 2003.
Measurement of the wave-front aberration of the eye by a fast psychophysical procedure. He et al. J. Opt. Soc. Am. A, vol. 15, No. 9: Sep. 1998, pp. 2449-2455.
Notch in contrast sensitivity function of optical origin: diffraction effects of acrylic filters. Irving et al. Ophthal. Physiol. Opt., vol. 13, Apr. 1993: pp. 179-182.
Optical Modeling of Contact Lens Performance Final Report Covering Period Jul. 15, 1994-Mar. 31, 1995. Grivenkamp et al. for Pilkington Barnes Hind, Issued Apr. 5, 1995.
Optometric Clinical Practice Guideline Care of the Patient With Presbyopia: Reference Guide for Clinicians. Mancil et al. Mar. 20, 1998.
PCT/US2010/045548 International Search Report and Written Opinion, dated Dec. 20, 2010 in 19 pages.
PermaVision intracorneallens shows promise for hyperopia. Kronemyer, Bob. Ocular Surgery News: Jan. 1, 2003; p. 8.
Perspectives in Refraction: Quantification of the Pinhole Effect. Miller et al. Survey of Ophthalmology, vol. 21, No. 4, Jan./Feb. 1977, pp. 347-350.
Sally Pobojewski, "New U-developed laser performs high-precision corneal surgery", News and Information Services, The University Record, Jul. 16, 1997.
Poly(methyl methacrylate) model study of optical surface quality after excimer laser photo refractive keratectomy. Hauge et al. J Cataract Refract Surg., vol. 27, Dec. 2001, pp. 2026-2035.
"Refractive Keratoplasty: Acute Morphologic Features," by Baumgarter et al, The CLAO Journal-Apr. 1985, vol. II, No. 2, pp. 163-169.
Refractive keratoplasty with intrastromal hydrogel lenticular implants. McCarey et al. Invest. Ophthalmol. Vis. ScL, Jul. 1981, pp. 107-115.
Retinal Image Quality in the Human Eye as a Function of the Accommodation. Lopex-Gil et al. Vision Research, vol. 38, No. 19, Jul. 3, 1998, pp. 1-11.
Simple parametric model of the human ocular modulation transfer function, A. Deeley et al. Ophthal. Physiol. Opt., vol. 11, Jan. 1991, pp. 91-93.
Karin R. Slettin, MD et al., "An In Vivo Model of Femtosecond Laser Intrastromal Refractive Surgery", Experimental Science, Opthalmic Surgery and Lasers, Nov./Dec. 1999, vol. 30, No. 9, pp. 742-749.
Subjective Depth-of-Focus of the Eye. Atchison et al. Optometry and Vision Science, vol. 74, No. 7, Jul. 1997, pp. 511-520.
Subrayan, V., et al., Improving quality of vision with an anterior surface modified prolate intraocular lens: A prospective clinical trial, Int. J. Ophthalmol., Jun. 2008, pp. 122-124, vol. 1, No. 2.
Surgeon: Severe corneal lesions after LASIK are not stage 4 DLK. Piechocki, Michael. Ocular SurgeryNews; Jan. 1, 2003, pp. 16-17.
Swinger et al., "Keratophakia and Keratomileusis-Clinical Results", American Academy of Opthalmology, Aug. 1981, vol. 88, No. 8, pp. 709-715.
Use of a digital infrared pupillometer to assess patient suitability for refractive surgery. Rosen et al. J Cataract Refract Surg., vol. 28: Aug. 2002. pp. 1433-1438.

(56) References Cited

OTHER PUBLICATIONS

Accommodation and acuity under night-driving illumination levels. Arumi et al. Opthal. Physiol. Opt. vol. 17, No. 4, pp. 291-299, Jul. 1997.

Accommodation and Presbyopia. Croft et al., International Opthalmology Clinics: Spring 2001, vol. 41, Issue 2, pp. 33-46.

Accommodation dynamics as a function of age. Heron et al. Opthal. Physiol. Opt. Sep. 2002 22:389-396.

Accommodative responses to anisoaccommodative targets. Koh et al. Ophthal. Physiol. Opt. vol. 18, No. 3, pp. 254-262, May 1998.

Accommodation responses to flickering stimuli. Chauhan et al. Ophthal. Physiol. Opt. vol. 16. No. 5, pp. 391-408, Sep. 1996.

Accommodation to perceived depth in stereo tests. Koh et al. Ophthal. Physiol. Opt. vol. 18, No. 3, pp. 279-284, May 1998.

Binder et al., "Hydrogel keratophakia in non-human primates", Current Eye Research, vol. 1, No. 9, Jan. 1981, pp. 535-542.

Cao et al., "Comparative study of the use of poly(glycolic acid), calcium alginate and pluronics in the engineering of autologous porcine cartilage", Polymers for Tissue Engineering, pp. 315-327, VSP 1998.

Changes in the static accommodation response with age. Kalsi et al. Ophthal. Physiol. Opt. vol. 21, No. 1, pp. 77-84, Jan. 2001.

Choyce, P. "Implants with Coloured and Opaque Portions: Implants with Built-In Stenopeic Aperture," pp. 21-26 "Uniocular Aphakia Corrected by Anterior Chamber Implants with Built-In Stenipeic Aperture," pp. 132-136, Intraocular Lenses and Implants, 1964.

Contemporary Polymer Applications for Corneal Surgery. McCarey, Bernard E. pp. 504-505, Sep. 1981.

"Corneal Surgery" by L. Girard, The C.V. Mosby Publishing Company, London Sep. 1981 pp. 107-141.

Dynamics of the accommodation response to abrupt changes in target vergence as a function of age. Heron et al. Vision Research 41 (Feb. 2001) 507-519.

Eduard Jaeger's Test-Types (Schrift-Scalen) and Historical Development of Vision Tests. Runge, Paul E. Tr. Am. Ophth. Soc. vol. 98, 2000: 375.

EP 00 913659.9 Examination Report, dated Jul. 20, 2006, 5 pp.

"Epikeratophakia: Techniques, Compositions, and Clinical Results" by Werblin, Opthalmology, 1983, pp. 45-58.

Errors in determining the direction of the visual axis in the presence of defocus. Atchison et al. Ophthal. Physiol. Opt., vol. 18, No. 5, pp. 463-467, Sep. 1998.

FDA Summary of Safety and Effectiveness Data for Tecnis Multifocal Posterior Chamber Intraocular Lens, Models ZM900 and ZMA00, Jan. 2009.

FDA Summary of Safety and Effectiveness Data for the Advanced Vision Science, Inc. XACT Foldable Hydrophopic Acrylic Ultraviolet Light-Absorbing Posterior Chamber Intraocular Lens (Model X-60 and Model X-70), Feb. 2009.

FDA Summary of Safety and Effectiveness Data for EC-3 IOL, (Models EC-3 IOL and EC-3 Precision Aspheric Lens), Oct. 2010.

FDA Summary of Safety and Effectiveness Data for Aaren Scientific's EC-3 IOL, Oct. 2010.

Focused and divided attention in stereoscopic deth. Wickens et al. SPIE, vol. 1256 Stereoscopic Displays and Applications (1990); pp. 28-34.

Glasier, M., et al., A solid-phase assay for the quantitation of total protein eluted from balafilcon, lotrafilcon, and etafilcon contact lenses, Current Eye Research, Jan. 2008, pp. 631-640, vol. 33, No. 8.

Groppi, J. J. "New Aspects in the Fitting of the Multi-Range Bifocal Contact Lens" Contacto, vol. 15:22-29 1971.

Hayasaka, S., et al., Scanning electron microscopic study of polyvinylidene fluoride degradation by ocular tissue extracts, Jpn. J. Ophthalmol., 1984, pp. 131-135, vol. 28.

Hidaka, T., et al, Adaptive optics instrumentation in submillimeter/terahertz spectroscopy with a flexible polyvinylidene fluoride cladding hollow waveguide, Rev. Sci. Instrum., Aug. 2007, pp. 086109-1-086109-2, vol. 78.

Human Visual System—Image Formation, Encyclopedia of Imaging Science and Technology, Roorda, A., Jan. 2002, pp. 539-557.

Iijima et al. "Formation of a spherical multicellular aggregate (spheroid) of animal cells in the pores of polyurethane foam as a cell culture substratum and its application to a hybrid artificial liver", Polymers for Tissue Engineering , pp. 273-286, VSP 1998.

Imaging in the 21st century. Charman, W. N. Ophthal. Physiol. Opt., vol. 18, No. 2, pp. 210-223, Mar. 1998.

Intra-Ocular Lenses and Implants. Choyce, Peter. Chpts.4 & 17, 1964.

Intraocular pressure after excimer laser myopic refractive surgery. Montes-Mico et al. Ophthal. Physiol. Opt., vol. 21, No. 3, pp. 228-235, May 2001.

Intrastromal Crystalline Deposits Following Hydrogel Keratophakia in Monkeys. Parks et al. Cornea 12(1): 29-34, Jan. 1993.

"Keratomileusis and Keratophakia in the Surgical Correction of Aphakia" by Barraquer, Cataract Surgery and Special Techniques, prior to 1996 pp. 270-289.

"Lamellar Corneal Stromectomy for the Operative Treatment of Myopia" by Tadeusz Krwawicz, Notes, Cases, Instruments—May 1964, pp. 828-833.

Microstructural Changes in Polyester Biotextiles During Implantation in Humans. King et al. NC State University: JTATM, vol. 1, Issue 3, Spring 2001, pp. 1-8.

Miller et al. "Quantification of the Pinhole effect" Perspectives in Refraction, vol. 21:347-350 Jan.-Feb. 1977.

Moran, C., et al. Polyvinylidene flouride polymer applied in an intraocular pressure sensor, Jpn. J. Appl. Phys., Jun. 24, 2005, pp. L885-L887, vol. 44, Issue 27.

Near vision, lags of accommodation and myopia. Charman, W. N. Ophthal. Physiol. Opt., vol. 19, No. 2, pp. 126-133, Mar. 1999.

New Visual Acuity Charts for Clinical Research. Ferris et al. American Journal of Ophthalmology, 94: 91-96, Jul. 1982.

Night myopia and driving. Charman, W. N. Ophthal. Physiol. Opt., vol. 16, No. 6, p. 474-485, Nov. 1996.

On modeling the causes of presbyopia. Glasser, A. Vision Research 41(Nov. 2001) 3083-3087.

On the linearity of accommodation dynamics. Charman, W. N. Vision Research 40 (Jul. 2000) 2057-2066.

Optical Aspects of Tolerances to Uncorrected Ocular Astigmatism. Charman et al. Optometry and Vision Science, vol. 70, No. 2: pp. 111-117, Feb. 1993.

Prince, S., et al., Sorption of alkylbenzyldimethylammonium chloride homologs to various filter media used in processing ophthalmics, APhA Annual Meeting, Nov. 1996, pp. 103, vol. 143.

Procyon: Marketing Information for Distributors: Pupil Measurement and Refractive Surgery (Samples from Academic Papers 1994 and 2002). pp. 1-17.

Rosenbloom "The Controlled-Pupil Contact Lens in Low Vision Problems" Journal of the American Optometric Association, pp. 836, 838, 840 Aug. 1969.

Shingleton, B., Reply: pupil stretch technique, J. Cataract Refract. Surg., Mar. 2007, pp. 362, vol. 33.

Subjective Sensitivity to Small Changes in the Contrast of a Suprathreshold Grating, The. Walsh et al. Vision Res., vol. 30, No. 1, pp. 163-193, Jan. 1990.

Surface Modification Properties of Parylene for Medical Applications, The. Wolgemuth, Lonny. Business Briefing: Medical Device Manufacturing & Technology 2002, pp. 1-4.

Surface tension control of collagen biomaterials by the selective hydrolysis of internal carboxyamides of the protein matrix. Revista Brasileira de Engenharia Biomedica, v. 15, n. 1-2, p. 55-61, Jan. 1999.

Takahashi, E. "Use and Interpretation of the Pinhole Test" The Optometric Weekly, pp. 83-86 May 1965.

Tasaki, I., et al., Demonstration of heat production associated with spreading depression in the amphibian retina, Biochem. Biophys. Res. Commun., Jan. 1991, pp. 293-297, vol. 174.

(56) References Cited

OTHER PUBLICATIONS

Theoretical and practical performance of a concentric bifocal intraocular implant lens. Charman, W.N. Vision Research 38 (Sep. 1998) 2841-2853.
Vision and driving—a literature review and commentary. Charman, W.N. Ophthal. Physiol. Opt., vol. 17, No. 5, pp. 371-391, Sep. 1997.
Wesley, N. K. "Research on the Multi-Range Lens," pp. 18-24, Nov. 1970.
Yamauchi et al., "Cultivation of fibroblast cells on keratin coated substrata", Polymers for Tissue Engineering, pp. 329-340, VS 1998.
Patel, C.K., et al. "Imaging the macula through a black occlusive intraocular lens". Arch. Ophthalmol. Oct. 2010; 128(10):1374-1376.
Yusuf, et al., "Inability to perform posterior segment monitoring by scanning laser ophthalmoscopy or optical coherence tomography with some occlusive intraocular lenses in clinical use", J. Cataract Refract. Surg., Mar. 2012, 38: 513-513.
Yusuf, et al., "Occlusive IOLs for Intractable Diplopia Demonstrate a Novel Near-Infrared Window of Transmission for SLO/OCT Imaging and Clinical Assessment". Investigative Ophthalmology & Visual Science, May 2011, 52(6): 3737-3743.
Internet Archive Wayback Machine; Aniridia Implants; downloaded from https://web.archive.org/web/20110824062840/http://www.morcher.com/nc/produkte/aniridiaimplants.html (Archived Aug. 24, 2011; printed on Feb. 5, 2015).
Guyton A.C., Textbook of Medical Physiology, 7th Edition, W.B. Saunders Company, Jan. 1986: Chapter 58, pp. 700-710.
International Search Report and Written Opinion for PCT/US2010/0455481 mailed Dec. 20, 2010 in 20 pages. [104VPC].
Lu Xuequan, et al. "Radiation preparation and thermo-response swelling of interpenetrating polymer network hydrogel composed of PNIPAAm and PMMA", Radiation Physics and Chemistry, vol. 57, Mar. 2000, pp. 477-480, XP002473596.

* cited by examiner

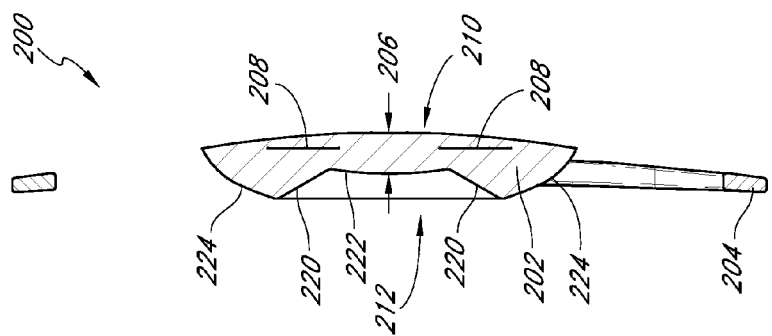
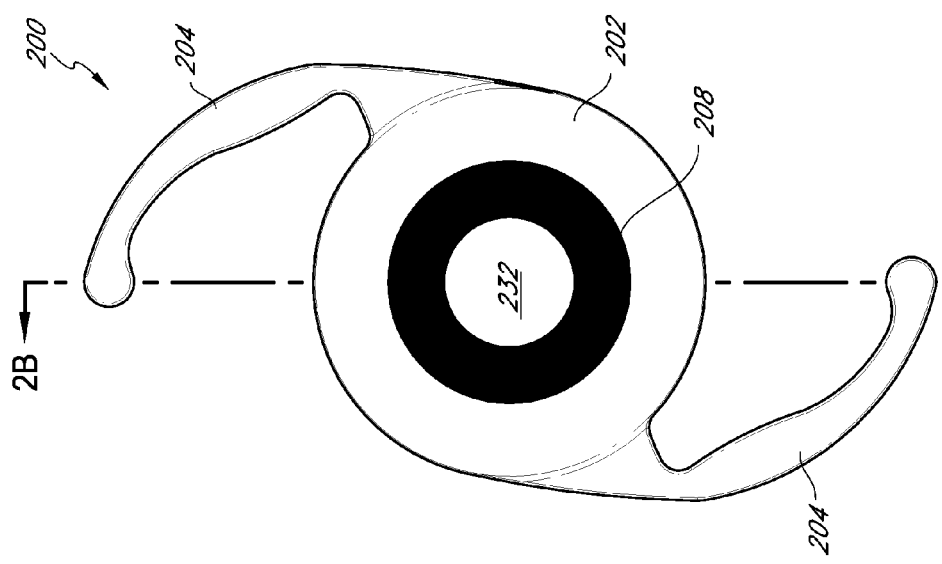

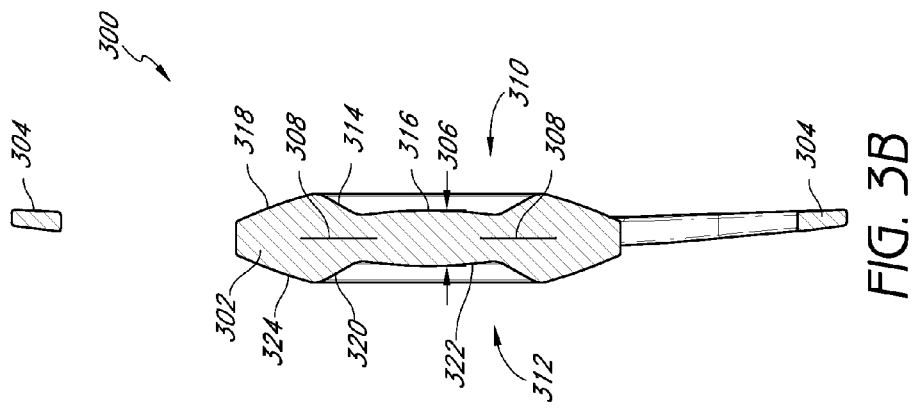
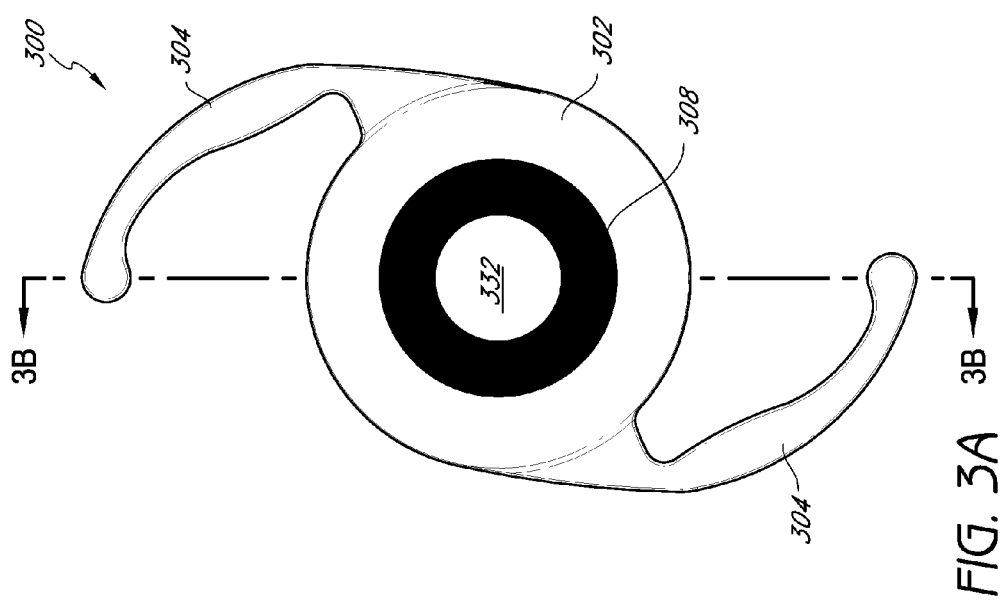

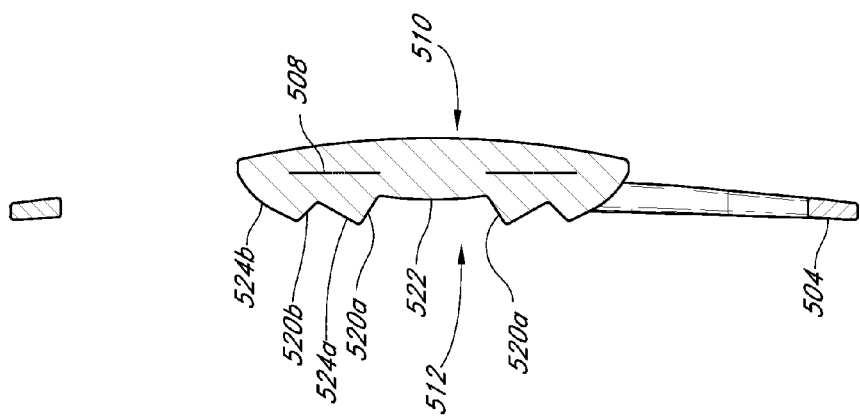
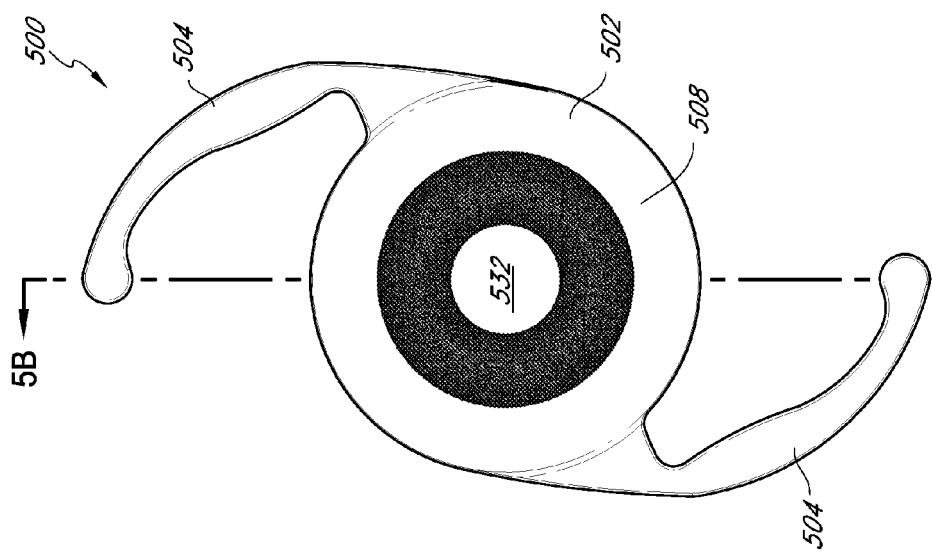

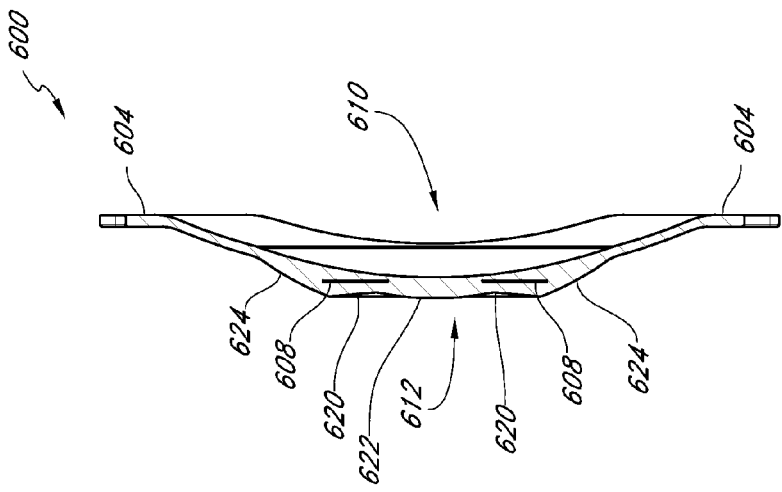
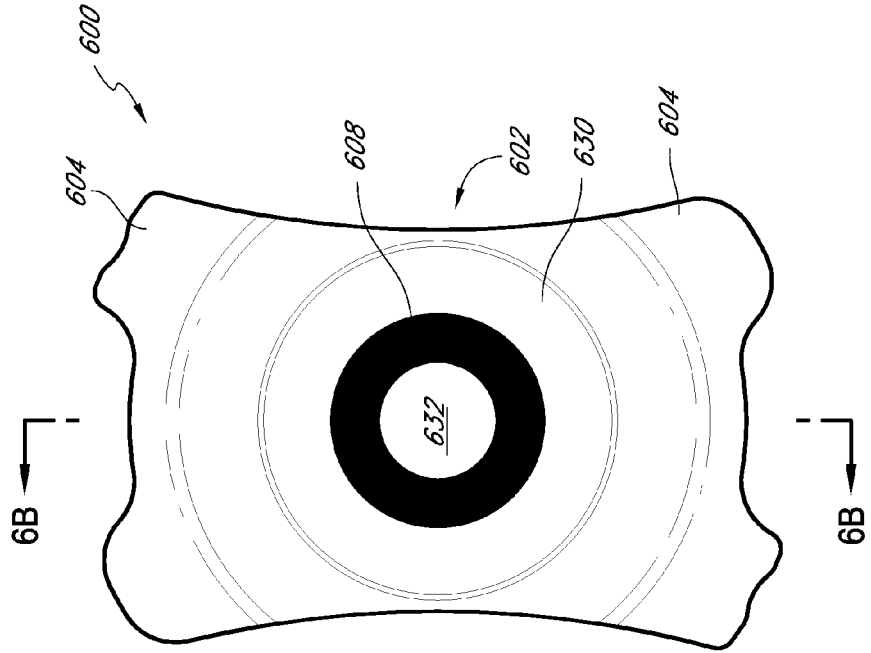
FIG. 6B
FIG. 6A

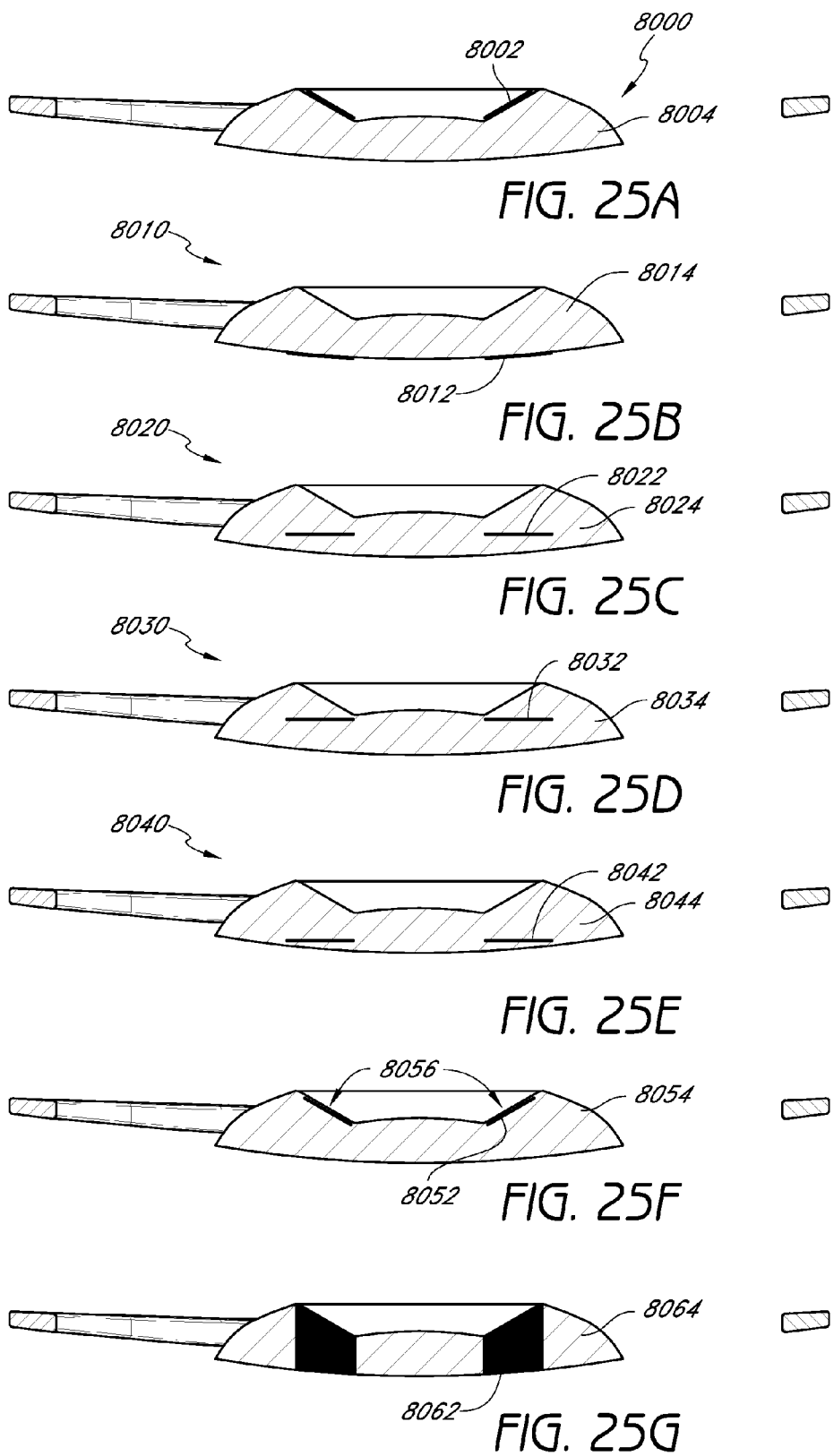

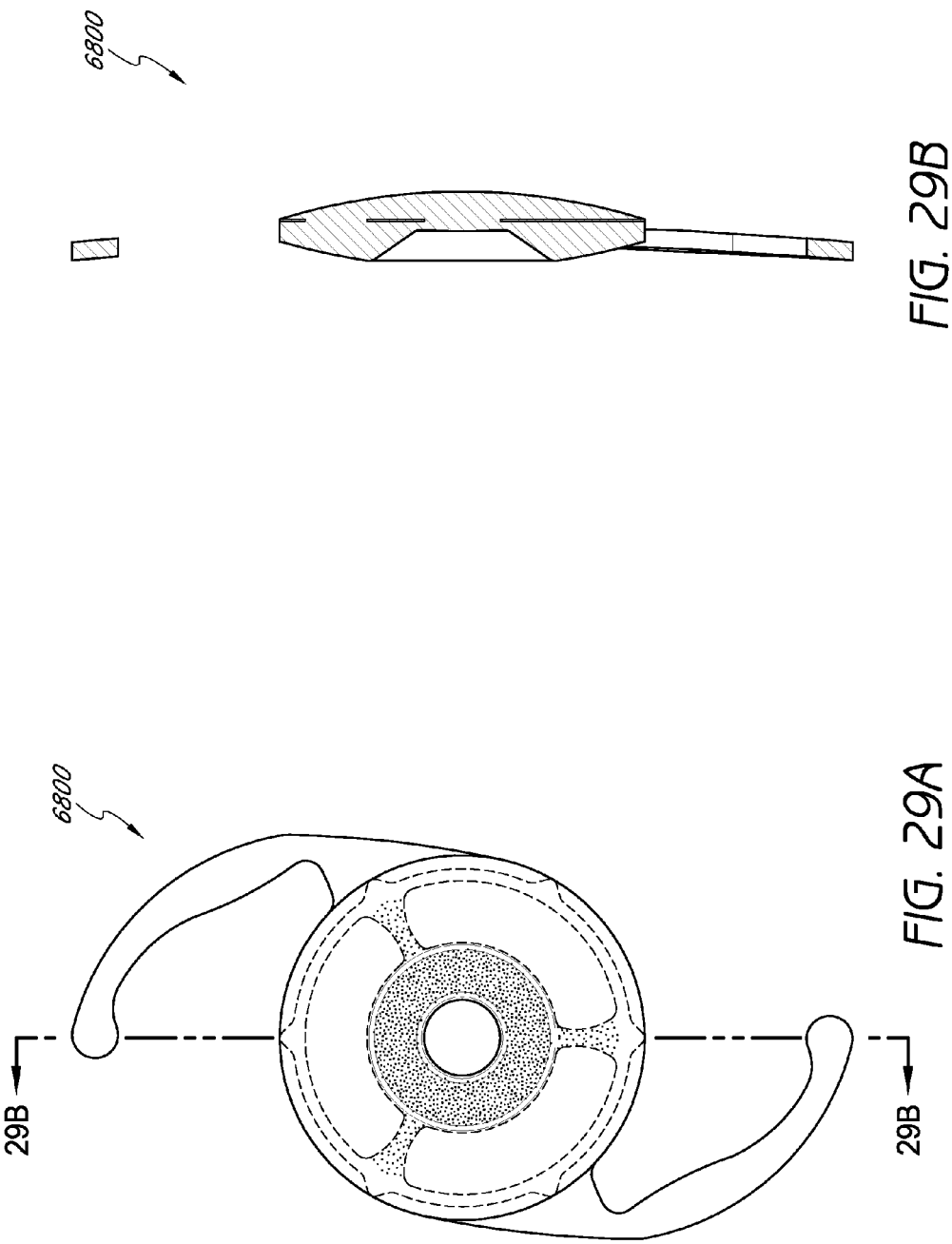

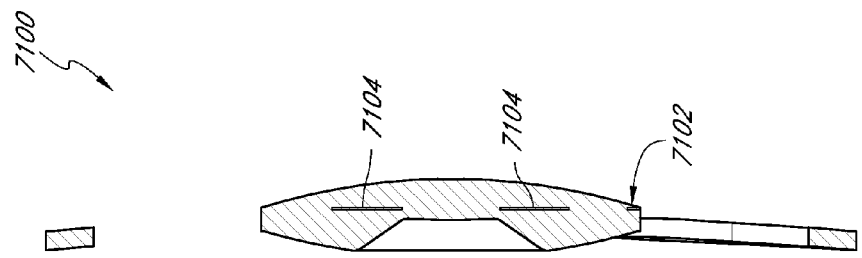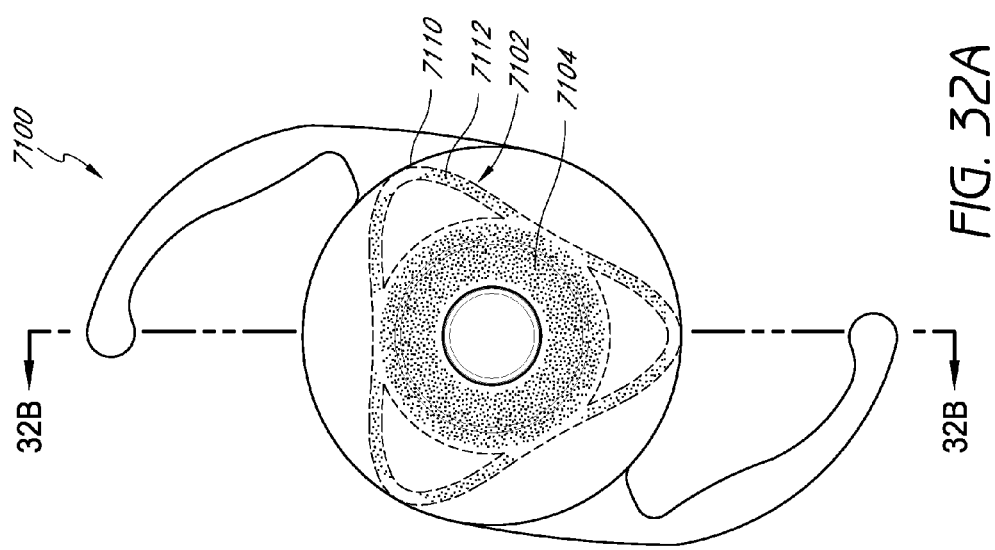

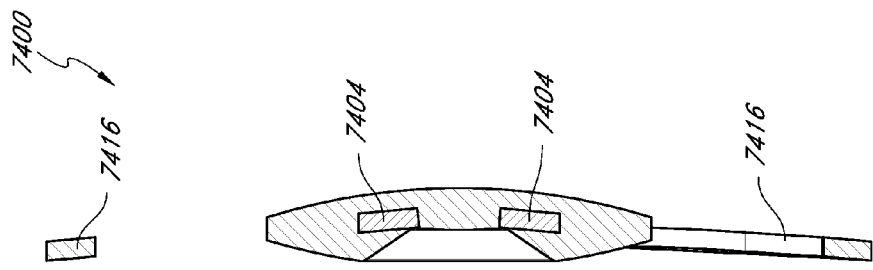
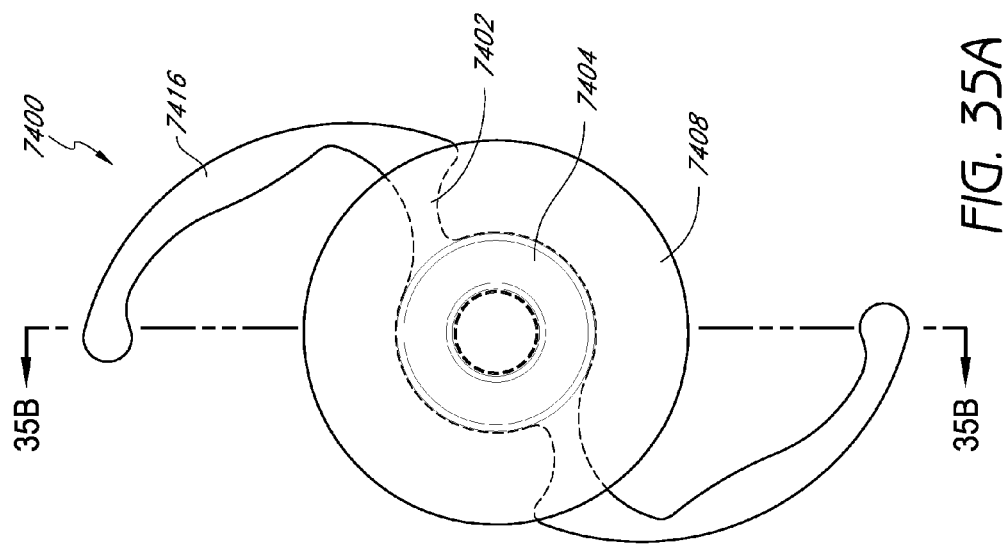
FIG. 35B
FIG. 35A

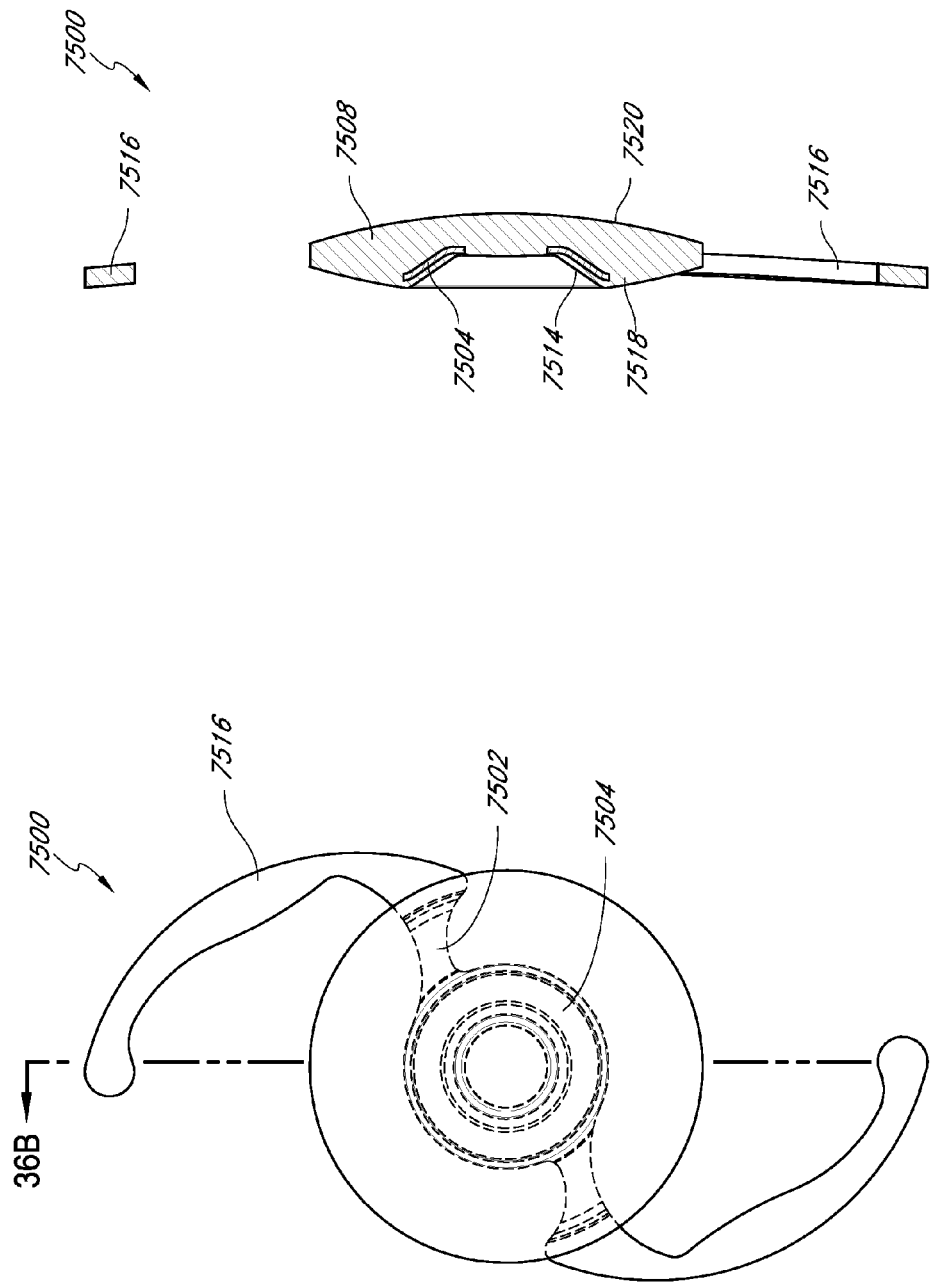

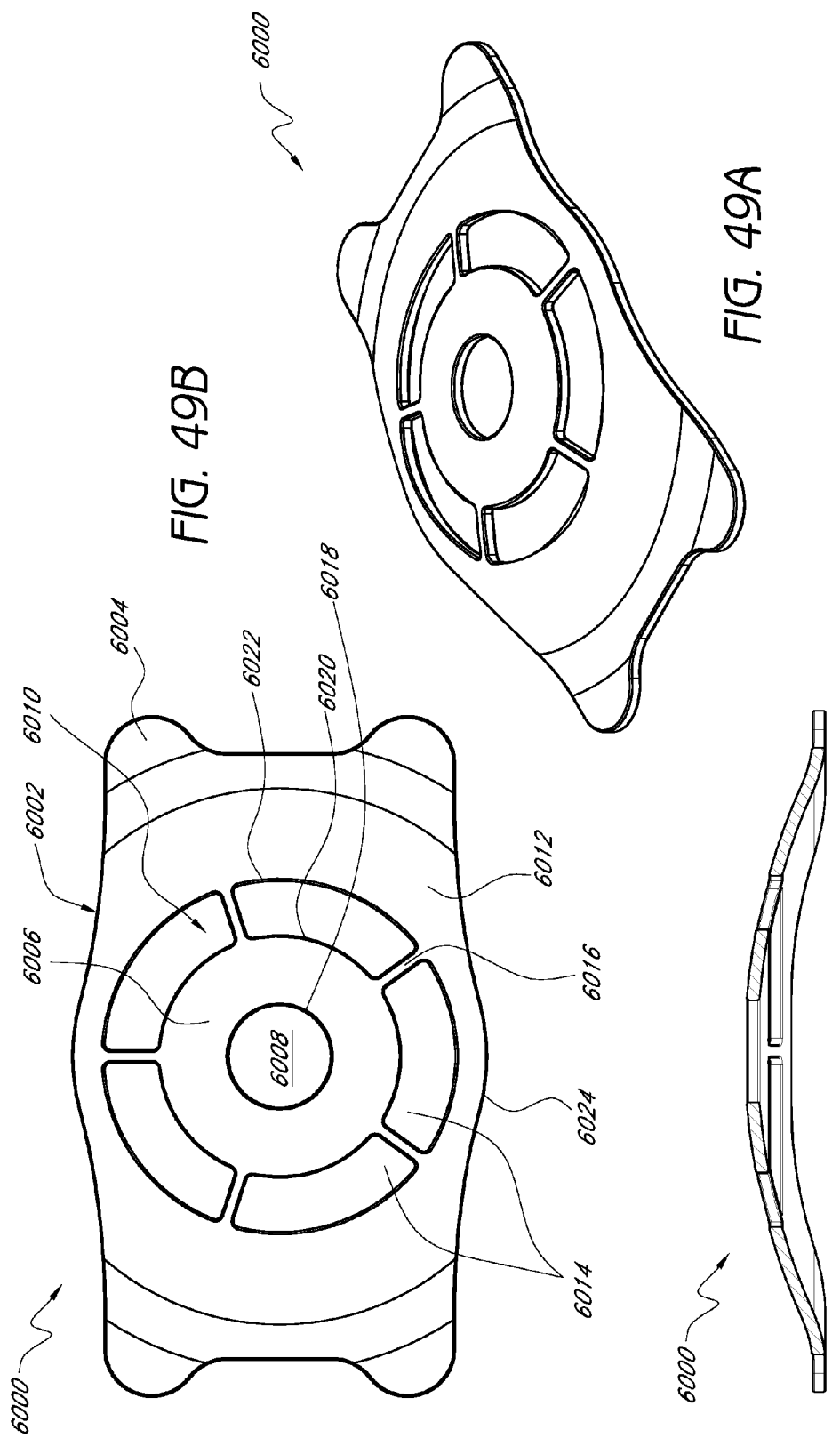

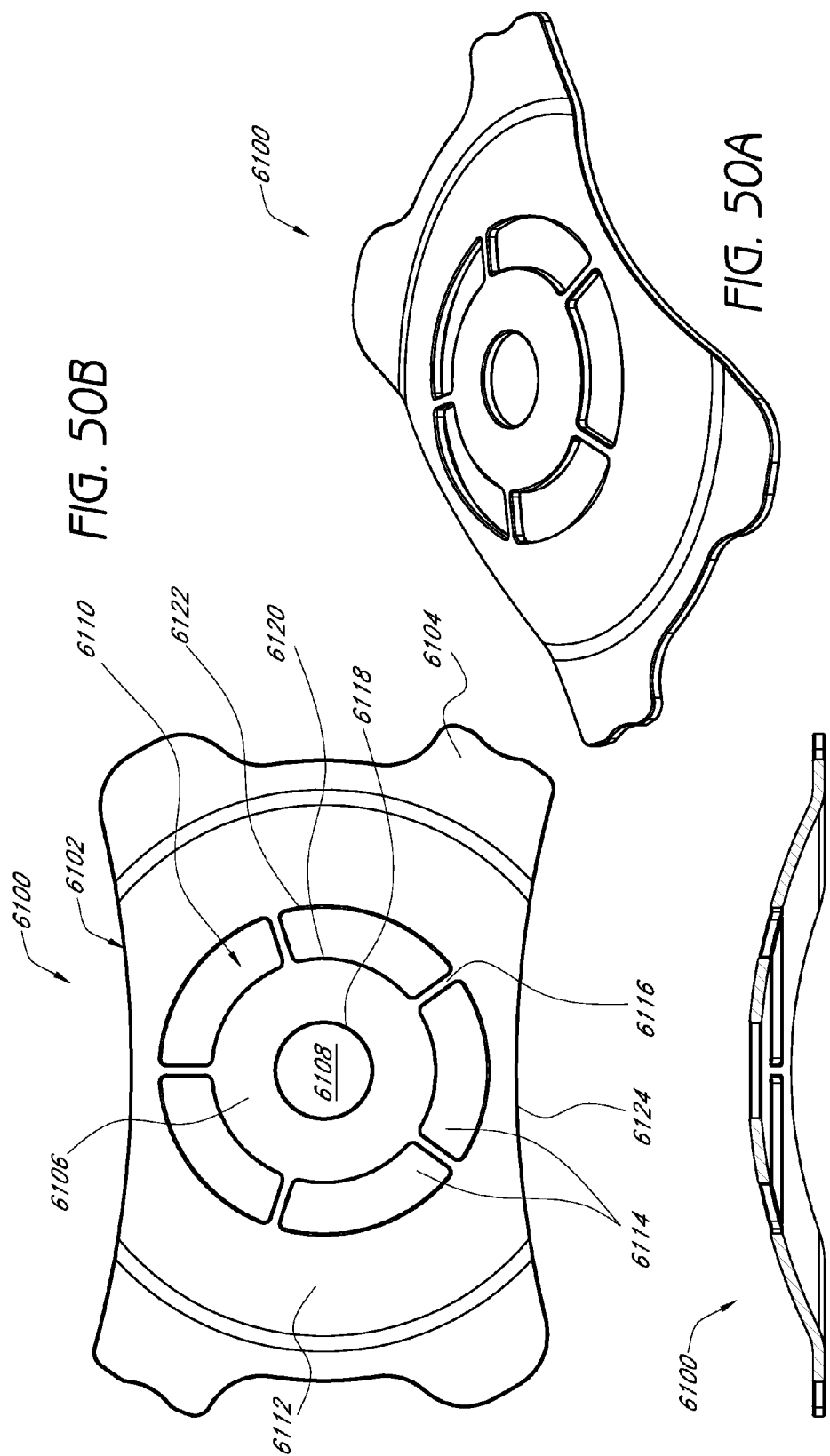

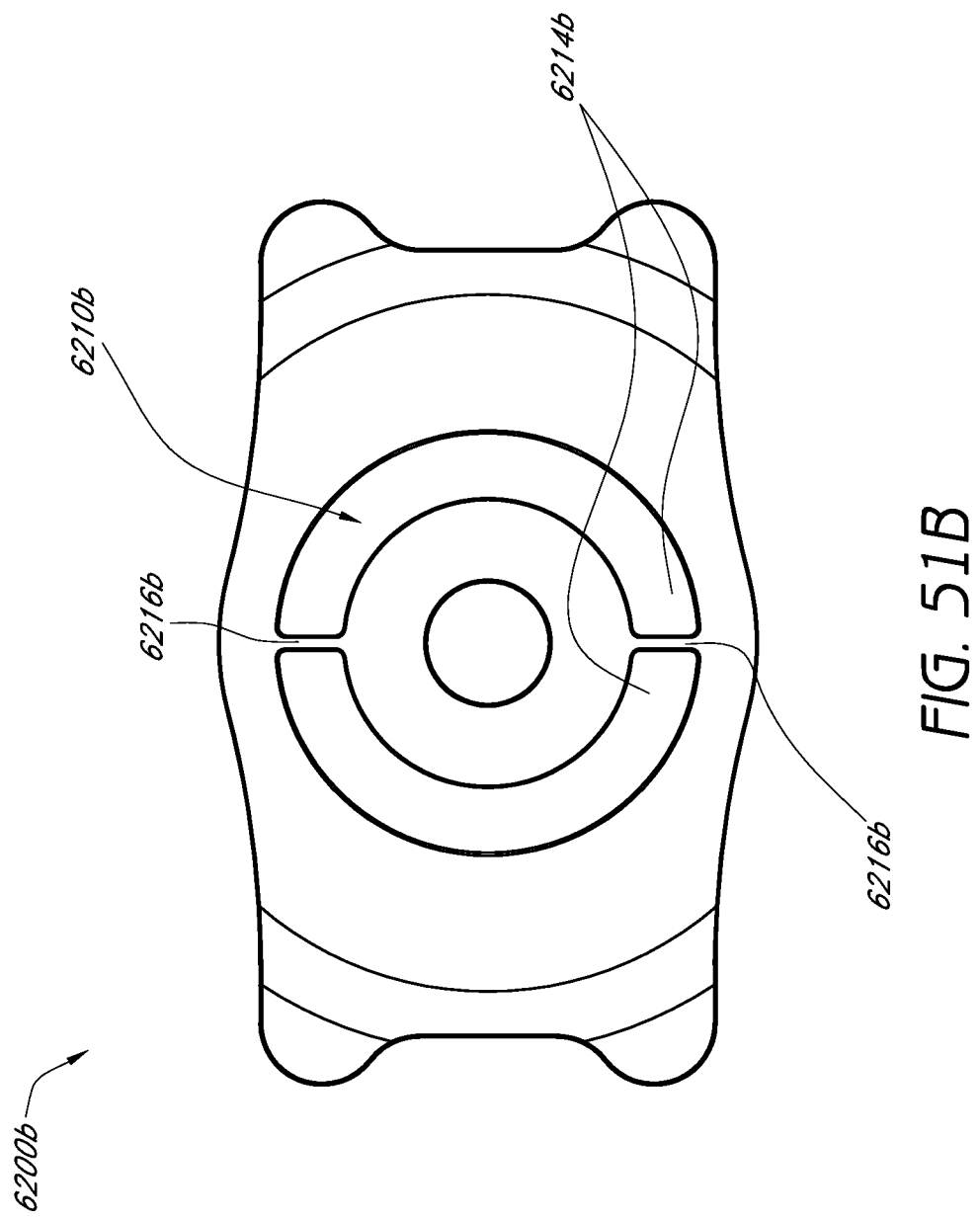

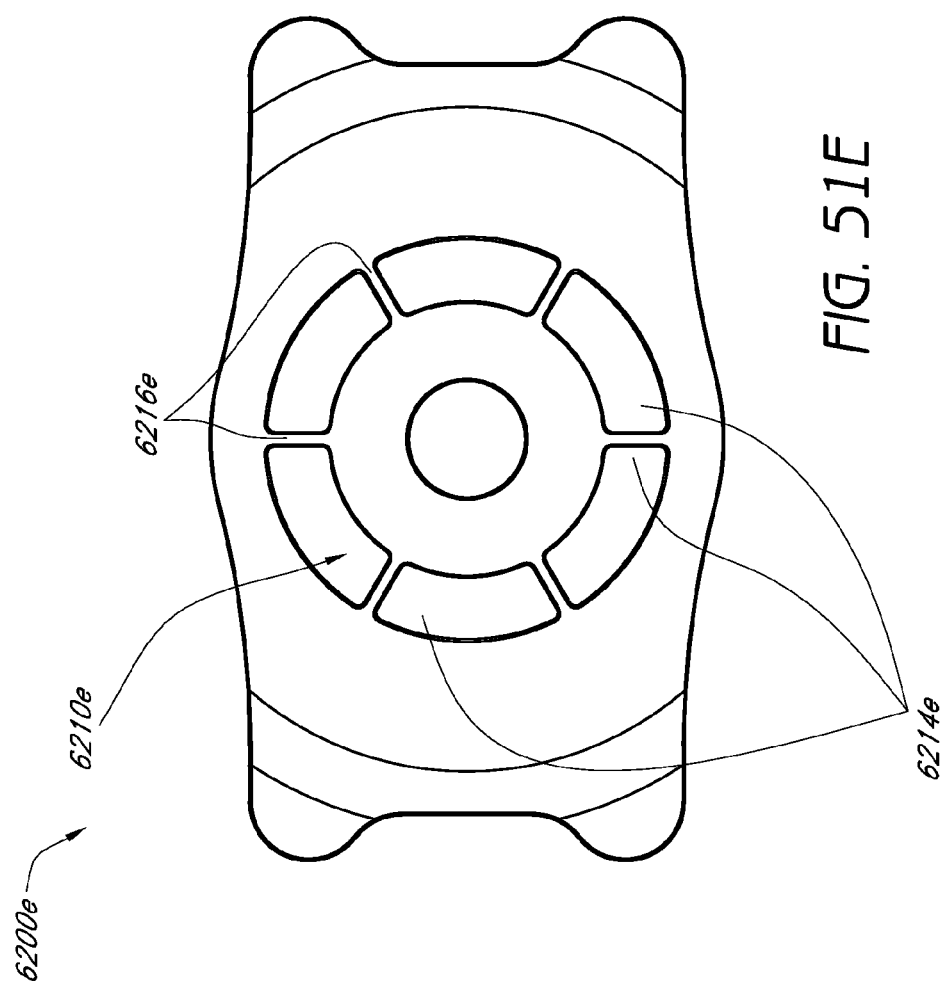

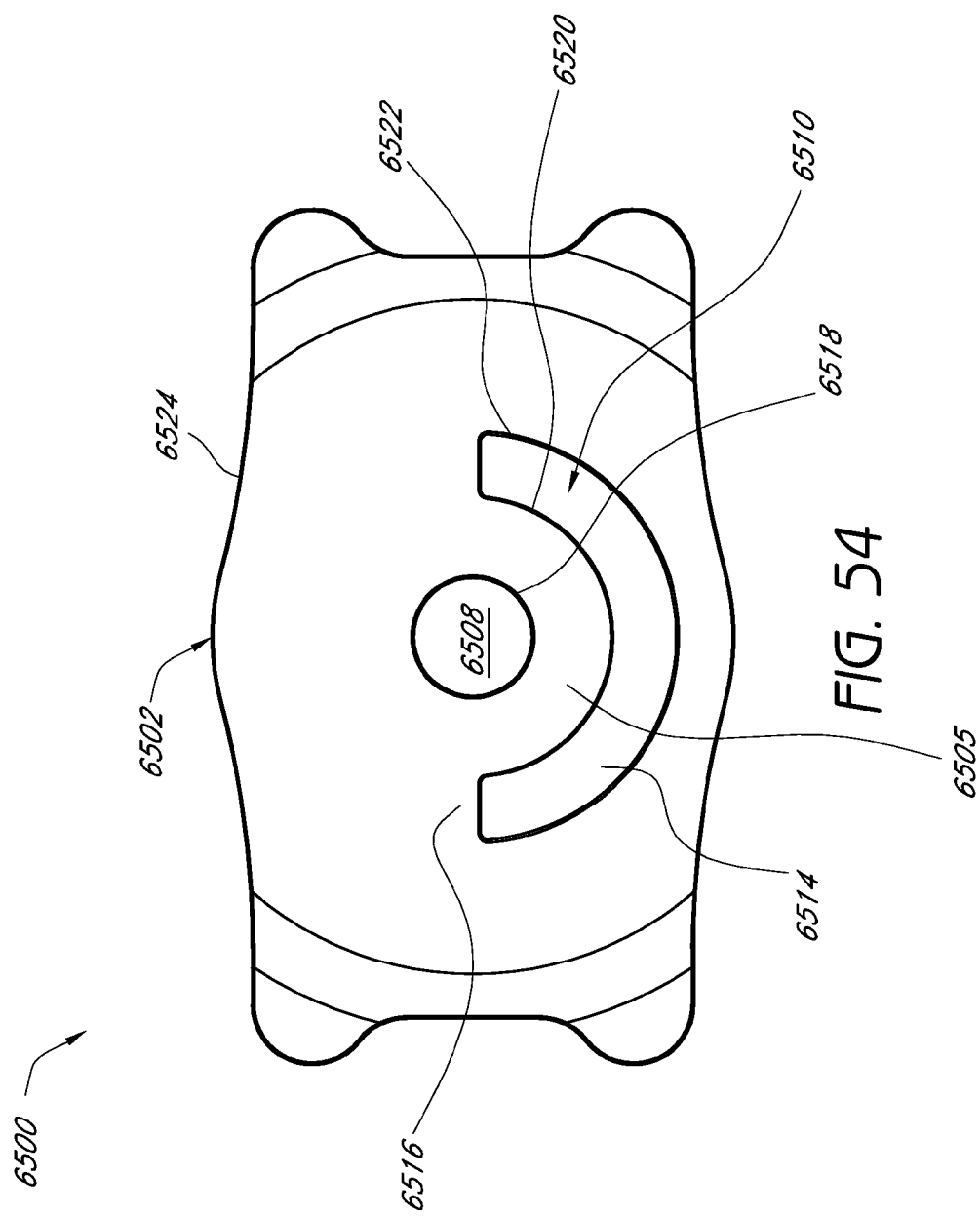

MASKED INTRAOCULAR IMPLANTS AND LENSES

CROSS-REFERENCE TO RELATED APPLICATIONS

This application claims the benefit of U.S. Provisional Application Nos. 61/233,794, filed Aug. 13, 2009, and 61/233,804, filed Aug. 13, 2009, the entirety of each of which is hereby incorporated by reference.

BACKGROUND

1. Field

This application relates generally to the field of intraocular devices. More particularly, this application is directed to intraocular implants and lenses (IOLs), with an aperture to increase depth of focus (e.g. "masked" intraocular lenses) and methods of making.

2. Description of the Related Art

The human eye functions to provide vision by transmitting and focusing light through a clear outer portion called the cornea, and further refining the focus of the image by way of a crystalline lens onto a retina. The quality of the focused image depends on many factors including the size and shape of the eye, and the transparency of the cornea and the lens.

The optical power of the eye is determined by the optical power of the cornea and the crystalline lens. In a normal, healthy eye, sharp images of distant objects are formed on the retina (emmetropia). In many eyes, images of distant objects are either formed in front of the retina because the eye is abnormally long or the cornea is abnormally steep (myopia), or formed in back of the retina because the eye is abnormally short or the cornea is abnormally flat (hyperopia). The cornea also may be asymmetric or toric, resulting in an uncompensated cylindrical refractive error referred to as corneal astigmatism.

A normally functioning human eye is capable of selectively focusing on either near or far objects through a process known as accommodation. Accommodation is achieved by inducing deformation in a lens located inside the eye, which is referred to as the crystalline lens. Such deformation is induced by muscles called ciliary muscles. In most individuals, the ability to accommodate diminishes with age and these individuals cannot see up close without vision correction. If far vision also is deficient, such individuals are usually prescribed bifocal lenses.

SUMMARY OF THE INVENTION

This application is directed to intraocular implants for improving the vision of a patient, such as by increasing the depth of focus of an eye of a patient. The intraocular implants can include a mask having an annular portion with a relatively low visible light transmission surrounding a relatively high transmission central portion such as a clear lens or aperture. This construct is adapted to provide an annular mask with a small aperture for light to pass through to the retina to increase depth of focus, sometimes referred to herein as pin-hole imaging or pin-hole vision correction. The intraocular implant may have an optical power for refractive correction. For example, the mask can be embodied in or combined with intraocular lenses (IOLs). The intraocular implant may be implanted in any location along the optical pathway in the eye, e.g., as an implant in the anterior or posterior chamber.

IOLs have been developed that provide a safe and effective surgical solution for cataracts. These lenses are surgically implanted after removal of a cataractous natural lens of the eye, restoring clarity and providing a replacement for the optical power that was removed. In a successful IOL implantation, the patient is typically emmetropic afterwards, meaning that their eye is focused for distance. However, conventional IOLs cannot accommodate to focus at different distances, so the patient typically needs additional correction (e.g., reading glasses) to see near objects clearly. Intraocular implants disclosed herein provide an improvement over presently available IOLs by incorporating a "mask" in the form of an aperture that improves depth of focus.

In certain embodiments, an intraocular device includes a lens body. The lens body includes an anterior and posterior surface. The posterior surface includes a first convex portion, a second concave portion and a third convex portion. The second concave portion is adjacent the first convex portion and the third convex portion. The third convex portion is annular and surrounds the second concave portion, and the second concave portion is annular and surrounds the first convex portion. An optical power between the first convex portion and the anterior surface is positive and an optical power between the third convex portion and the anterior surface is positive. The lens body further includes a mask positioned between the second concave portion and the anterior surface.

In certain embodiments, a lens body of an intraocular device includes a first surface and a second surface. A first portion of the first surface is convex, a second portion of the first surface is concave, and a third portion of the first surface is convex. The second portion is adjacent the first portion and the third portion. The lens body further includes a mask positioned to block a substantial portion of optical aberrations that would be created by the light passing through the second portion of the first surface.

In certain embodiments, an intraocular device includes a lens body with a positive optical power. The lens body includes an outer region and a recessed central region. At least a portion of the recessed central region includes a thickness less than at least a portion of the outer region. The lens body further includes a mask coupled with a curved transition between the outer region the recessed central region.

In certain embodiments, a method of making an intraocular device includes providing a lens body with a first surface and a second surface. The method further includes forming a convex surface on a first portion of the first surface, a concave surface on a second portion of the first surface and a convex surface on a third portion of the first surface. The second portion is adjacent the first portion and the third portion. The method also includes attaching a mask to the lens body that is positioned to block a substantial portion of the light passing through the second portion of the first surface.

In certain embodiments, a method of making an intraocular device includes forming a rod with an optically transparent inner region along a length of the rod, an optically transparent outer region along the length of the rod and a substantially optically non-transparent region along the length of the rod between the inner region and the outer region. The substantially non-transparent region can be a middle region, as discussed below. The method also can include sectioning the rod along a plane substantially perpendicular to an axis parallel to the length of the rod to form a lens body with a first surface and a second surface. The method also can include forming a convex surface on a first portion of the first surface. The first portion can correspond to the inner region of the sectioned rod. The method can include forming a concave surface on a second portion of the first surface. The second portion can correspond to the non-transparent region. The method can include forming a convex surface on a third portion of the first surface. The third portion can correspond to the outer region. The second portion is adjacent the first portion and the third portion. In some embodiments, the non-transparent region is positioned such that, in use, the non-transparent region blocks a substantial portion of the light passing through the second portion of the first surface.

In certain embodiments, a method of making an intraocular device includes forming a lens body around a mask. The mask includes an aperture and an annular region, and the lens body comprising a first surface and a second surface. The method further includes forming a convex surface on a first portion of the first surface, a concave surface on a second portion of the first surface and a convex surface on a third portion of the first surface. The second portion is adjacent the first portion and the third portion. Forming the lens body around the mask includes locating the mask within the lens body such that, in use, the mask blocks a substantial portion of the light passing through the second portion of the first surface.

In certain embodiments, an intraocular implant includes an implant body. The implant body can include a pin-hole aperture in the implant body, and a mask substantially around the pin-hole aperture. The implant body can further include an outer hole region substantially outside an outer perimeter of the mask. The outer hole region can include at least one outer hole and at least one connection portion. An outer region of the implant body can be attached to the mask by the at least one connection portion.

In some embodiments, an intraocular device includes a lens body comprising a surface with a transition zone, the transition zone configured to reduce a thickness of the lens body along an optical axis of the lens body, and a mask configured to block a substantial portion of optical aberrations that would be created by light passing through the transition zone.

In further embodiments, an intraocular device includes a lens body comprising a first surface and a second surface. The first surface comprises a first portion, a second portion and a third portion. An optic axis of the lens body passes through the first portion, and the second portion is between the first portion and the third portion. The intraocular device can also include a mask positioned between the second surface and the second portion of the first surface. A distance from the first portion neighboring the second portion to a plane perpendicular to the optic axis and tangent to the second surface can comprise a first distance, and a distance from the third portion neighboring the second portion to the plane perpendicular to the optic axis and tangent to the second surface can comprise a second distance greater than the first distance.

In other embodiments, a method for improving the vision of a patient includes providing an intraocular device comprising a lens body comprising a surface with a transition zone. The transition zone can be configured to reduce a thickness of the lens body along an optic axis of the lens body, and the intraocular device can further include a mask configured to block a substantial portion of optical aberrations that would be created by light passing through the transition zone. The method can further include inserting the intraocular device into an intraocular space of an eye.

In certain embodiments, an intraocular implant includes an implant body comprising an outer surface that includes a posterior surface and an anterior surface, an opaque mask positioned between the posterior surface and the anterior surface of the implant body. The mask comprising an aperture. The intraocular implant can further include a support member coupled to the mask and extending from the mask to the outer surface of the implant body. The support member can extend from the mask to the posterior surface of the implant body. A first portion of the support member neighboring the mask can have a first cross-sectional area parallel the mask and a second portion of the support member neighboring the posterior surface can have a second cross-sectional area parallel the mask that is less than the first cross-sectional area. The support member may be configured to be removable from the intraocular implant. The support member may include a plurality of holes characterized in that at least one of the hole size, shape, orientation, and spacing of the plurality of holes is varied to reduce the tendency of the holes to produce visible diffraction patterns.

In certain embodiments, a method of making an intraocular implant includes providing an opaque mask comprising an aperture and at least one support member coupled to the mask, positioning the mask within a mold chamber such that the at least one support member is coupled to the mold chamber so that the mask resists movement, and flowing a lens material into the mold chamber so that at least a portion of the mask is encased within the lens material. The method may further include removing at least a portion of the at least one support member after injecting the lens material.

In other embodiments, a method of making an intraocular implant includes coupling an opaque mask comprising an aperture to a surface of a mold chamber, and flowing a lens material into the mold chamber to form an optic coupled to the mask.

In further embodiments, a method of making an intraocular implant includes removing a portion of a surface of an optic to form an annular cavity around an aperture region, at least partially filling the cavity with an opaque material, removing at least some of the aperture region and a central region of the optic to reduce a thickness of the aperture region of the optic. At least some of the opaque material may remain on the surface of the optic to form an opaque mask.

In another embodiment, a method of making an intraocular implant includes providing an optic with an annular cavity around an aperture region, at least partially filling the cavity with an opaque material, removing at least some of the aperture region and a central region of the optic to reduce a thickness of the aperture region of the optic. At least some of the opaque material can remain on the surface of the optic to form an opaque mask.

In even further embodiments, a method of making an intraocular implant includes positioning an opaque mask with an aperture within a mold cavity such that the mask is not in physical contact with the mold cavity, and injecting an implant body material into the mold cavity to form an implant body around the mask. For example, the mask can be positioned with magnetic fields or with wires extending from the mask to a frame outside of the mold cavity.

In certain embodiments, a intraocular implant includes an implant body comprising a body material and a mask with an aperture positioned within the implant body. The mask can include a plurality of holes that extend between a posterior surface and an anterior surface of the mask. The body material can extend through the plurality of holes of the mask, and the plurality of holes can be characterized in that at least one of the hole size, shape, orientation, and spacing of the plurality of holes is varied to reduce the tendency of the holes to produce visible diffraction patterns. The plurality of holes may be positioned at irregular locations. A first plurality of the holes may include first hole size, shape or spacing and at least another plurality of holes may include a second hole size, shape, or spacing different from the first holes size, shape, or spacing. A first plurality of the holes may include first hole size, a second plurality of the holes may include a second hole size different from the third hole size, and a third plurality of holes may include a third hole size different from the first holes size and the second hole size.

In certain embodiments, an intraocular implant includes an implant body configured to be implanted into a sulcus region of an eye of a patient. The implant body can include an aperture that is at least partially surrounded by an opaque region forming a mask and an outer hole region substantially outside an outer perimeter of the mask. The outer hole region can include at least one outer hole and at least one connection portion, and the outer hole region can have an incident visible light transmission of at least 90%. The implant body may also include an outer region attached to the mask by the at least one connection portion.

In other embodiments, a method of making an intraocular implant includes providing an implant body configured to be implanted into a sulcus region of an eye of a patient, forming an aperture in the implant body by removing a portion of the implant body, and forming at least one opening between the outer edge of the structure and a opaque mask region that neighbors the aperture.

BRIEF DESCRIPTION OF THE DRAWINGS

FIG. 2A illustrates a front plan view of an embodiment of an intraocular lens with a recessed central region on the anterior surface as described herein.

FIG. 2B illustrates a cross-sectional view of the intraocular lens of FIG. 2A.

FIG. 3A illustrates a front plan view of an embodiment of an intraocular lens with a recessed central region on the posterior surface and anterior surface as described herein.

FIG. 3B illustrates a cross-sectional view of the intraocular lens of FIG. 3A.

FIG. 5A illustrates a front plan view of an embodiment of an intraocular lens with two transition zones and a single mask as described herein.

FIG. 5B illustrates a cross-sectional view of the intraocular lens of FIG. 5A.

FIG. 6A illustrates a front plan view of an embodiment of an intraocular lens with a concave posterior surface and a positive optical power as described herein.

FIG. 6B illustrates a cross-sectional view of the intraocular lens of FIG. 6A.

FIG. 25A is a cross-sectional view of an embodiment of an intraocular implant with a mask coupled to the anterior surface of a transition zone as described herein.

FIG. 25B is a cross-sectional view of an embodiment of an intraocular implant with a mask coupled to the posterior surface as described herein.

FIG. 25C is a cross-sectional view of an embodiment of an intraocular implant with a mask embedded within the implant body about midway between the posterior and anterior surfaces as described herein.

FIG. 25D is a cross-sectional view of an embodiment of an intraocular implant with a mask embedded within the implant body which is closer to the anterior surface than the posterior surface as described herein.

FIG. 25E is a cross-sectional view of an embodiment of an intraocular implant with a mask embedded within the implant body which is closer to the posterior surface than the anterior surface as described herein.

FIG. 25F is a cross-sectional view of an embodiment of an intraocular implant with a mask embedded within the implant body and within close proximity of the anterior surface of a transition zone as described herein.

FIG. 25G is a cross-sectional view of an embodiment of an intraocular implant with a mask that extends between the anterior and posterior surfaces as described herein.

FIG. 29A is a front plan view of an embodiment of an intraocular implant with a different optical power than the intraocular implant of FIG. 27A.

FIG. 29B is a cross-sectional view of the intraocular implant of FIG. 29A.

FIG. 32A is a front plan view of another embodiment of an intraocular implant with a mask that extends radially beyond the outer periphery of the transition zone as described herein.

FIG. 32B is a cross-sectional view of the intraocular implant of FIG. 32A.

FIG. 35A is a front plan view of an embodiment of an intraocular implant with a support member coupled with a haptic as described herein.

FIG. 35B is a cross-sectional view of the intraocular implant of FIG. 35A.

FIG. 36A is a front plan view of another embodiment of an intraocular implant with a support member coupled with a haptic as described herein.

FIG. 36B is a cross-sectional view of the intraocular implant of FIG. 36A.

FIG. 49A is a top perspective view of an embodiment of an intraocular implant with five outer holes described herein.

FIG. 49B is a top plan view of the intraocular implant of FIG. 56A.

FIG. 49C is a side elevational view of the intraocular implant of FIG. 56A.

FIG. 50A is a top perspective view of an embodiment of an intraocular implant with a different haptic than the intraocular implant of FIG. 56A described herein.

FIG. 50B is a top plan view of the intraocular implant of FIG. 57A.

FIG. 50C is a side elevational view of the intraocular implant of FIG. 57A.

FIG. 51B is a top plan view of an embodiment of an intraocular implant with two outer holes described herein.

FIG. 51E is a top plan view of an embodiment of an intraocular implant with six outer holes described herein.

FIG. 54 is a top plan view of an embodiment of an intraocular implant with an outer hole region that partially surrounds the aperture described herein.

DETAILED DESCRIPTION

Figure 1B:
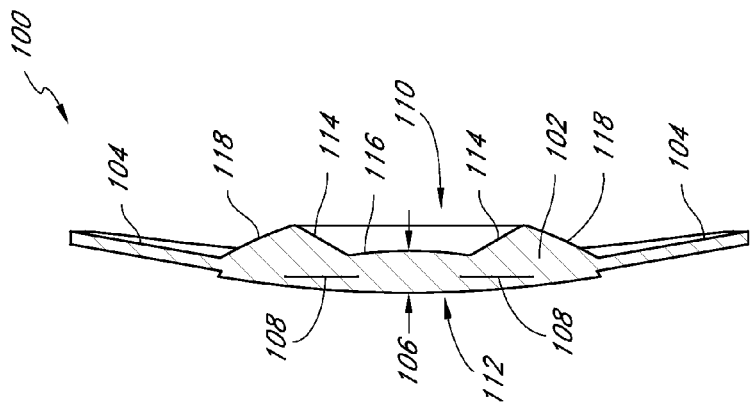
FIG. 1B illustrates a cross-sectional view of the intraocular lens of FIG. 1A.

This application is directed to intraocular implants and methods of implanting intraocular implants. The natural lens of an eye is often replaced with an intraocular lens when the natural lens has been clouded over by a cataract. An intraocular lens may also be implanted into the eye to correct other refractive defects without removing the natural lens. The intraocular implants of the preferred embodiments include a mask adapted to provide a small aperture for light to pass through to the retina to increase depth of focus, sometimes referred to herein as pinhole imaging or pinhole vision correction. The intraocular implants may be implanted in the anterior chamber or the posterior chamber of the eye. In the posterior chamber, the implants may be fixated in the ciliary sulcus, in the capsular bag, or anywhere an intraocular implant is fixated. In some embodiments discussed below, the intraocular lenses have a reduced thickness in a central region compared to conventional intraocular lenses. The reduced thickness in the central region can help improve implantation of the intraocular lens. In further embodiments discussed below, intraocular implants can have an outer hole region (e.g. perforated region) to improve a patient's low light vision.

I. Intraocular Implants with Reduced Thickness

Several alternatives to fixed-focus IOLs have been developed, including multifocal IOLs and accommodating IOLs that attempt to provide the ability to see clearly at both distance and near. Multifocal IOLs do provide good acuity at both distance and near, but these lenses typically do not perform well at intermediate distances and are associated with glare, halos, and night vision difficulties associated with the presence of unfocused light. Accommodating IOLs of several designs have also been developed, but none so far has been able to replicate the function of the natural crystalline lens. IOLs with apertures have been described by Vorosmarthy (U.S. Pat. No. 4,976,732). These devices, however, do not attempt to change focus from far to near, but merely attempt to reduce the blurry image from defocus to a level where a presbyopic emmetrope can read. Notably, Vorosmarthy did not address the issue of reducing thickness of a masked IOL for application in small-incision surgery.

Some embodiments of the present application provide a masked IOL with a thinner optic than has been known in the art. The advantage to a thinner optic is that the IOL can be inserted through a smaller incision into the eye. Since corneal incisions tend to distort the cornea and impair vision, reducing the size of the incision will improve the quality of vision. The optic is made thinner by means similar to a Fresnel lens, where alternating concentric zones provide focusing power and height steps. While the thickness reduction possible with a Fresnel lens is significant, the height steps are optically inappropriate for clinical application. They do not focus light to an image at the fovea, but instead scatter light, leading to dysphotopsias (streaks, shadows, halos, etc.) in the patient's vision. By combining Fresnel-type height steps with a mask that blocks light from passing through the steps and allows light to pass only through the focusing surfaces, one can eliminate the dysphotopsias associated with a common Fresnel lens, obtaining the benefit of reduced thickness without introducing unwanted optical effects.

Generally, intraocular implants are implanted into the eye by rolling up an intraocular implant and inserting the rolled up intraocular implant into a tube. The tube is inserted into an incision in the eye, and the intraocular implant is ejected out of the tube and deployed within the eye. Intraocular implants can be implanted within the lens capsule after removal of the natural lens, or in the anterior chamber, posterior chamber, and can be coupled with or attached to the ciliary sulcus (sometimes referred to herein as "sulcus-fixated"). Depending on the location of the intraocular implant within the eye, dimensions of the intraocular implant, including but not limited to the aperture of the mask, may be adjusted. By reducing the thickness of in the central region of the intraocular lens, the intraocular lens can be rolled up tighter and inserted into a smaller tube. A smaller incision can be made in the eye if a smaller tube is used. The result is a less invasive procedure with quicker recovery time for the patient. Also, compared with a conventional posterior chamber phakic intraocular lens, a reduced thickness lens that is fixated in the ciliary sulcus will allow more space between the intraocular lens posterior surface and the natural crystalline lens surface, thereby reducing the potential for contact between these surfaces.

In certain embodiments, an intraocular lens 100 includes a lens body 102 with an optical power to refract light and correct refractive errors of the eye. Certain embodiments are illustrated in FIGS. 1-10. The intraocular lens 100 may include one or more haptics 104 to prevent the intraocular lens 100 from moving or rotating within the eye. As used herein the term "haptic" is intended to be a broad term encompassing struts and other mechanical structures that can be apposed against an inner surface of an eye and mounted to a lens structure to securely position a lens in an optical path of an eye. The haptics 104 can be a variety of shapes and sizes depending on the location the intraocular lens 100 is implanted in the eye. Haptics illustrated in FIGS. 1-10 can be interchanged with any variety of haptic. For example, the haptics illustrated in FIGS. 1-10 can be combined with the intraocular lens illustrated in FIGS. 1-10. Haptics may be C-shaped, J-shaped, plate design, or any other design. An intraocular implant described herein may have two, three, four, or more haptics. The haptics may be of open or closed configuration and may be planar, angled, or step-vaulted. Examples of haptics are disclosed in U.S. Pat. Nos. 4,634,442; 5,192,319; 6,106,553; 6,228,115; Re. 34,251; 7,455,691; and U.S. Patent Application Publication 2003/0199978, which are incorporated in their entirety by reference.

Figure 1A:
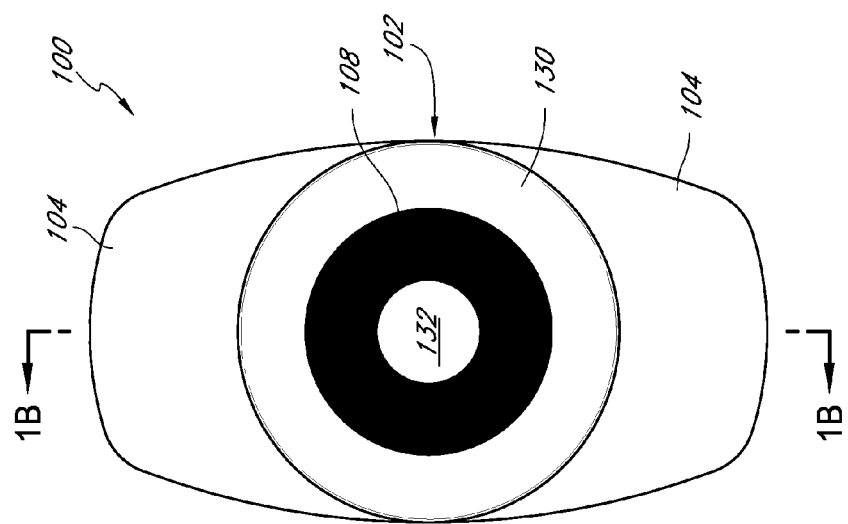
FIG. 1A illustrates a front plan view of an embodiment of an intraocular lens with a recessed central region on the posterior surface as described herein.

In certain embodiments, the lens body 102 includes a posterior surface 110 and an anterior surface 112, as illustrated in FIGS. 1A-B. The lens body 102 includes a first portion 116 (e.g., inner portion or central region), a second portion 114 (e.g., transition zone) and a third portion 118 (e.g., outer portion or region) on the posterior surface 110.

The second portion 114 can be between and/or adjacent the first portion 116 and the third portion 118. The second portion 114 can substantially surround the first portion 116, and the third portion 118 can substantially surround the second portion 114. In certain embodiments, the first portion 116 is substantially circular, and the second portion 114 and third portion 118 are substantially annular. The first portion 116 and third portion 118 can refract light or have an optical power to improve a patient's vision. The second portion 114 has one or more facets, grooves, crests, troughs, depressions, contours, surface curvatures, etc. to make the first portion 116 closer to the anterior surface 112 than if the posterior surface 110 did not have the second portion 114. The second portion 114 can also be described as a "transition zone" between the first portion 116 and the third portion 118. For example, the second portion 114 transition zone can slope toward the anterior surface 112 from the third portion 118 to the first portion 116. In certain embodiments, the second portion 114 transition zone includes a surface substantially perpendicular to the anterior surface 112. The transition zones are like those incorporated in a Fresnel lens. They enable the lens body to be made thinner than would be required in a conventional lens design. However, as with Fresnel lenses, the transition zones introduce optical aberrations that would not be clinically acceptable in intraocular lenses.

The intraocular lens 100 can include a mask 108 that can be positioned to block a substantial portion of light that would pass through the second portion 114 transition zone of the posterior surface 110. "Blocked" as used in this context includes preventing at least a portion of light from passing through the mask, as well as preventing substantially all the light from passing through the mask. If the mask 108 did not block the light rays that would pass through the second portion 114, aberrations would result since the refraction of light (e.g. optical power, etc.) in the second portion 114 is typically different than in the first portion 116 and the third portion 118.

In certain embodiments, the first portion 116 is convex, the second portion 114 is concave, and the third portion 118 is convex. In certain embodiments, the first portion 116 and the third portion 118 have a positive or converging optical power and the second portion 114 has a negative or diverging optical power. The second portion 114 may have curvature or no curvature in a direction extending radially from the first portion 116 to the third portion 118. For example, the second portion 114 may have a positive or negative curvature (e.g., convex or concave) in a direction extending radially from the first portion 116 to the third portion 118. Furthermore, the second portion 114 may form a closed loop and have surface similar to an outer surface of a frustoconical shape.

In certain embodiments, the first portion 116 is within a central region 132 of the lens body 102. The central region 132 can be recessed within the lens body 102. In certain embodiments, the third portion 118 is within an outer region 130 of the lens body 102. In certain embodiments, an outer perimeter of the first portion 116 is surrounded and/or enclosed by an inner perimeter of the second portion 114. In certain embodiments, an outer perimeter of the second portion 114 is surrounded and/or enclosed by an inner perimeter of the third portion 118. In certain embodiments, the maximum thickness of the lens body 102 in the region of the first portion 116 is less than the maximum thickness of the lens body 102 in the region of the second portion 114.

In certain embodiments, a lens body 202 includes a first portion 222, a second portion 220 and a third portion 224 on the anterior surface 212, as illustrated in FIGS. 2A-B. The first portion 222, the second portion 220 and the third portion 224 on the anterior surface 212 can have similar features as described above for the first portion 116, the second portion 114 and the third portion 118 on the anterior surface 112. The intraocular lens 200 can include a mask 208 that is positioned to block a substantial portion of light that passes through the second portion 220 of the anterior surface 212.

In certain embodiments, both an anterior surface 312 and a posterior surface 310 have a first portion 316, 322, a second portion 314, 320 and a third portion 318, 324, as illustrated in FIGS. 3A-B. A mask 308 can be positioned so that a substantial portion of the light that passes through the second portion 320 of the anterior surface 312 and the light that would pass through the second portion 314 of the posterior surface 310 will be blocked by the mask 308.

In certain embodiments, the mask is coupled with the second portion, which is concave. For example, the mask can be located adjacent the second portion. In certain embodiments, the mask is attached to the posterior surface, the anterior surface, or the posterior and the anterior surfaces. In certain embodiments, the mask is within the lens body or between the posterior surface and the anterior surface. The radial width or the area of the mask can be about the same as the radial width or the area of the second portion. In certain embodiments, the mask can extend at least partially into the area of the first portion and/or the third portion of the lens body. By extending the mask into the first portion and/or the third portion, the mask can block light that enters at large angles off the optical center axis of the lens body and that may then pass through the second portion.

Figure 4B:
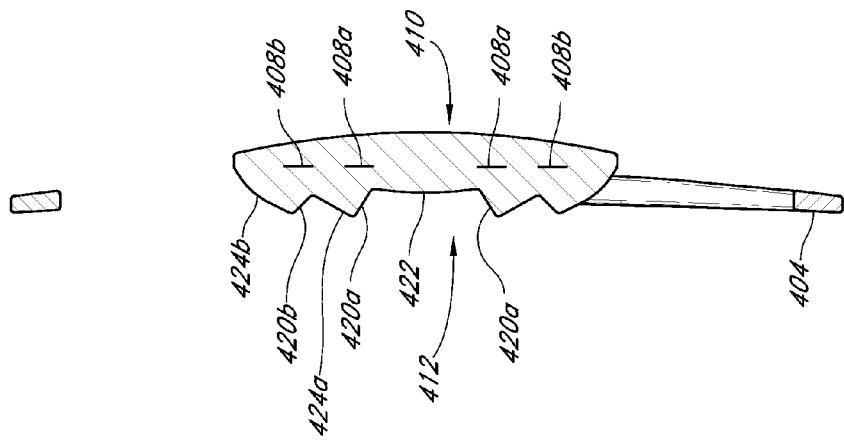
FIG. 4B illustrates a cross-sectional view of the intraocular lens of FIG. 4A.
Figure 4A:
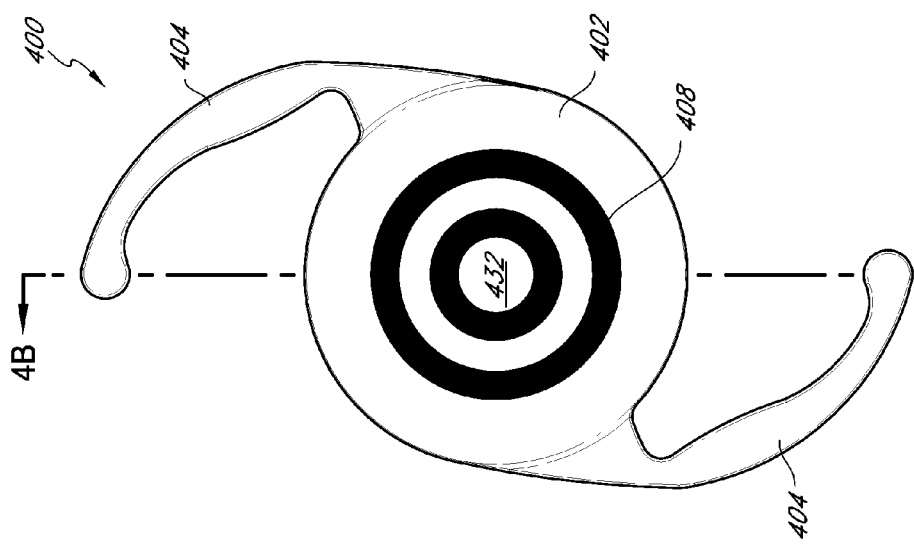
FIG. 4A illustrates a front plan view of an embodiment of an intraocular lens with two transition zones and two masks as described herein.

Illustrated in FIGS. 4A-B, an intraocular lens 400 can further include a fourth portion 420b and a fifth portion 424b on the anterior surface 412 and/or the posterior surface 410. The fourth portion 420b is adjacent the third portion 424a and can substantially surround the third portion 424a. The fifth portion 424b is adjacent the fourth portion 420b and can substantially surround the fourth portion 420b. The fourth portion 420b can have similar features as described above for the second portion 420a, and the fifth portion 424b can have similar features as described above for the third portion 424a. The intraocular lens 400 can include a first mask 408a that is positioned to block a substantial portion of light that passes through the second portion 420a of the anterior surface 412, and a second mask 408b that is positioned to block a substantial portion of light that passes through the fourth portion 420b of the anterior surface 412. It should be understood that additional pairs of portions with a mask like the fourth portion 420b, the fifth portion 424b and the second mask 408b can be further included in an intraocular lens.

FIGS. 5A-B illustrate an intraocular lens 500 similar to the intraocular lens 400 illustrated in FIGS. 4A-B. Instead of the intraocular lens 400 having a first mask 408a and a second mask 408b, the intraocular lens 500 has a single mask 508 with a plurality of light transmission holes that allow at least partial light transmission through the mask 508. The light transmission holes can be configured to allow substantially no light that passes through the second portion 520a and the fourth portion 520b to pass through the mask 508, but allow at least some light that passes through the third portion 524a to pass through the mask 508. For example, a middle annular region of the mask can have a plurality of holes to allow at least some light to pass through the mask, and an inner annular region and an outer annular region can have substantially no holes. Light transmission structures or holes are further discussed in sections below and can be applied to embodiments discussed herein.

The variety of intraocular lenses described herein are designed to suit the vision correction needs of particular patients. For example, for patients with relatively small pupils, dim light may present more of a vision issue than for patients with larger pupils. For smaller pupil patients, a mask with more light transmission and/or a smaller outer diameter will increase the amount of light that reaches the retina and may improve vision in dim light situations. Conversely, for larger pupil patients, less light transmission and/or a larger outer diameter mask may improve low-contrast near vision and block more unfocused light. The masked IOLs described herein give the surgeon flexibility to prescribe the appropriate combination of masked IOL features for particular patients.

Figure 7B:
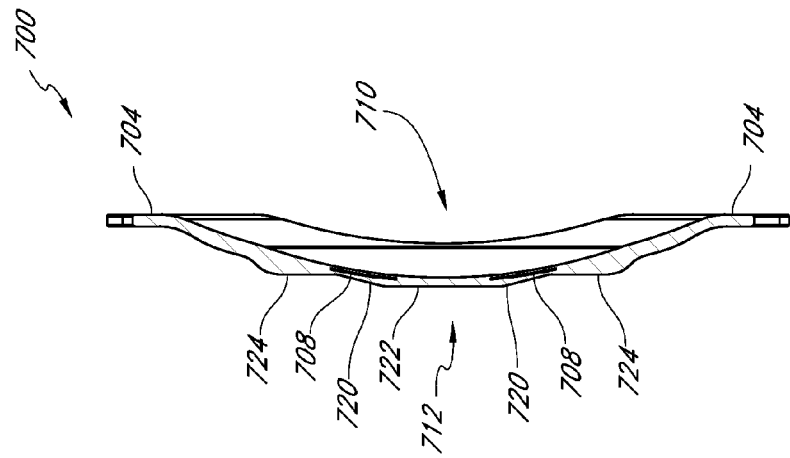
FIG. 7B illustrates a cross-sectional view of the intraocular lens of FIG. 7A.
Figure 7A:
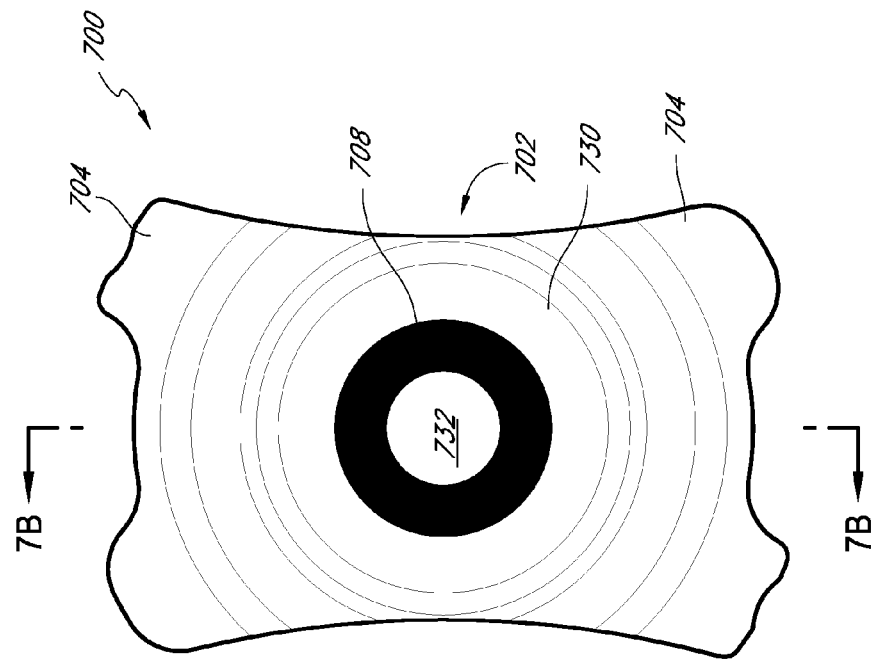
FIG. 7A illustrates a front plan view of an embodiment of an intraocular lens with a concave posterior surface and a negative optical power as described herein.

FIGS. 6-7 illustrate additional embodiments of intraocular lenses 600, 700. The posterior surface and anterior surface of an intraocular lens can have a variety of curvatures. For example, the posterior surface and/or the anterior surface can be concave or convex. FIGS. 6A-B illustrates an intraocular lens 600 with a concave posterior surface 610 with an anterior surface 612 to create a positive optical power lens. FIGS. 7A-B illustrate an intraocular lens 700 with a concave posterior surface 710 with an anterior surface 712 to create a negative optical power lens. Both intraocular lenses 600, 700 have a second portion 620, 720 to reduce the overall thickness of the intraocular lenses 600, 700. Both intraocular lenses 600, 700 also can include a mask 608, 708 to block light that passes through the second portion 620, 720. For negative power intraocular lenses, such as the intraocular lens 700 of FIG. 7, the thickness of the central region 732 of the lens body 702 may not be reduced by the second portion 720. However, the thickness of the outer region 730 of the lens body 702 can be reduced by the second portion 720 (e.g., transition zone). Advantageously, if an intraocular lens has a positive optical power or a negative optical power, the thickness of at least a portion of the lens body can be reduced by having the lens body include a second portion.

Tables I and II illustrate examples of intraocular lens with reduced lens body thicknesses. The column labeled "Reduced" corresponds to an intraocular lens with a second portion (e.g. transition zone), and the column labeled "Original" is corresponds to an intraocular lens without a second portion. The optic diameter is the diameter of the outer-most portion of the lens body with an optical power. The reduction percentage of the center region thickness indicated in Tables I and II can be about proportional to the reduction in the possible rolled up diameter of a reduced thickness IOL. Therefore, the reduction percentage of the center region thickness indicated in Tables I and II can also be about proportional to the reduction in the incision size that can be used during implantation of the IOL in a patient. An IOL is rolled up and inserted into a tube, and the tube is inserted into the incision. The IOL can then be deployed into the intraocular space of the eye. The IOL is often rolled up as tight as possible so that open space (e.g., voids) is minimized in a cross-section of the tube at a location where the implant body has the greatest cross-sectional area that is generally parallel with the optical axis of the implant body. Therefore, the cross-sectional area of the tube is greater than or equal to the greatest cross-sectional area of the implant body that is generally parallel with the optical axis of the implant body. For example, a 36% reduction in the cross sectional area of the implant body could reduce the cross sectional area of the tube by 36% or could reduce the diameter of the tube by about 20%. A minimum incision length is generally one-half of the circumference of the tube. Therefore, a 36% reduction in the cross sectional area of the implant body can result in about 20% reduction in incision length. For example, a 1.8 mm incision could be reduced to about 1.44 mm. A smaller incision is beneficial because it avoids post-operative astigmatism.

TABLE I

Examples of reduced thickness IOLs with positive optical power.

| Optic Diameter [mm] | Material [Ref. index] | Diopter | Center region thickness [mm] | | | Cross section area of center region [mm$^2$] | | |
|---|---|---|---|---|---|---|---|---|
| | | | Original | Reduced | Reduction [%] | Original | Reduced | Reduction [%] |
| Biconvex IOL | | | | | | | | |
| 5.5 | 1.4300 | 18.0 | 0.94 | 0.42 | 55 | 3.96 | 2.48 | 37 |
| 5.5 | 1.4300 | 24.0 | 1.20 | 0.56 | 53 | 4.93 | 3.13 | 37 |
| 5.5 | 1.4583 | 18.0 | 0.77 | 0.32 | 58 | 3.32 | 2.05 | 38 |
| 5.5 | 1.4583 | 24.0 | 0.96 | 0.42 | 56 | 4.02 | 2.51 | 38 |
| 6.0 | 1.4300 | 18.0 | 1.08 | 0.50 | 54 | 4.76 | 3.08 | 35 |
| 6.0 | 1.4300 | 24.0 | 1.40 | 0.62 | 56 | 6.04 | 3.85 | 36 |
| 6.0 | 1.4583 | 18.0 | 0.87 | 0.37 | 57 | 3.92 | 2.50 | 36 |
| 6.0 | 1.4583 | 24.0 | 1.10 | 0.50 | 55 | 4.88 | 3.13 | 36 |
| Sulcus-fixated IOL | | | | | | | | |
| 5.5 | 1.4583 | 5.0 | 0.34 | 0.15 | 56 | 1.75 | 1.22 | 30 |
| 5.5 | 1.4583 | 10.0 | 0.52 | 0.20 | 62 | 2.43 | 1.51 | 38 |
| 6.0 | 1.4583 | 5.0 | 0.37 | 0.17 | 54 | 1.95 | 1.36 | 30 |
| 6.0 | 1.4583 | 10.0 | 0.59 | 0.21 | 64 | 2.86 | 1.76 | 38 |

TABLE II

Examples of reduced thickness IOLs with negative optical power.

| Optic Diameter [mm] | Material [Ref. index] | Diopter | Outer region thickness [mm] | | | Cross section area of outer region [mm$^2$] | | |
|---|---|---|---|---|---|---|---|---|
| | | | Original | Reduced | Reduction [%] | Original | Reduced | Reduction [%] |
| Sulcus-fixated IOL | | | | | | | | |
| 5.5 | 1.4583 | −5.0 | 0.26 | 0.17 | 35 | 1.09 | 0.77 | 29 |
| 5.5 | 1.4583 | −10.0 | 0.41 | 0.25 | 39 | 1.52 | 0.97 | 36 |
| 6.0 | 1.4583 | −5.0 | 0.29 | 0.20 | 31 | 1.12 | 0.77 | 31 |
| 6.0 | 1.4583 | −10.0 | 0.48 | 0.32 | 33 | 1.57 | 0.99 | 37 |

Figure 8:
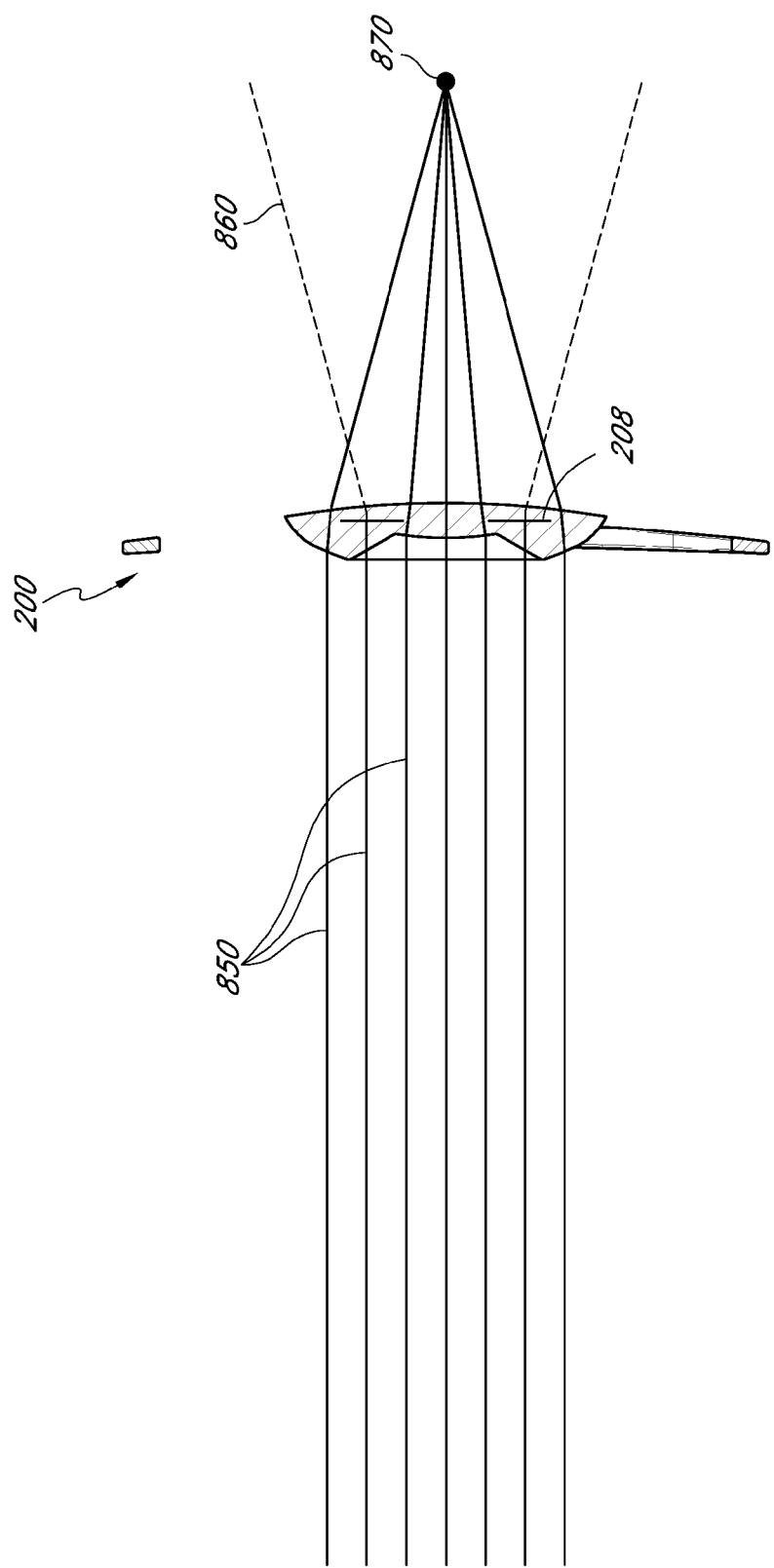
FIG. 8 is a cross-sectional schematic representation of light passing through the intraocular lens of FIG. 2B.

FIG. 8 illustrates the operation of the intraocular lens 200 of FIGS. 2A-B. In use, light enters the anterior surface 212, passes through the lens body 202 and exits the posterior surface 210 of the intraocular lens 200. The mask 208 is located such that the mask 208 blocks a substantial portion of the light rays 850 that pass through the second portion 220 of the anterior surface 212, as illustrated in FIG. 8. If the mask 208 did not block the light rays 850 that pass through the second portion 220, aberrations would result. For example, if the curvature of the second portion 220 is configured to provide a negative or divergent optical power, light rays 860 passing through this region would diverge and not focus, as illustrated in FIG. 8. The light rays 850 that pass through the first portion 222 and/or the third portion 224 would have a positive or convergent optical power. If the first portion 222 and the third portion 224 have a similar curvature or optical power, light rays 450 entering the anterior surface 212 and passing through the first portion 222 and/or the third portion 224 would converge at a common point 870 after passing through the posterior surface 210, as illustrated in FIG. 8. FIG. 9A illustrates an intraocular lens 200 implanted within the capsular bag 954 of an eye 952. Parallel light rays 950 that pass through the intraocular lens 200 converge on the retina 956.

The lens body 202 can include one or more materials. In certain embodiments, the lens body 202 includes two or more materials. For example, the first portion 222 and the third portion 224 can include different materials. If the materials selected for the first portion 222 and the third portion 224 have different refractive indexes, the curvature of the first portion 222 and the third portion 224 can be different to obtain a similar optical power (e.g. dioptric power) for both portions.

Generally, the optical power of an intraocular lens is selected for focusing on far objects. A natural lens can deform to change the focal distance for far and near viewing. Conventional artificial intraocular lenses are generally unable to change the focal distance. For example, an eye that is presbyopic or where an artificial intraocular lens has an optical power for farther distance, light rays that enter the eye and pass through the cornea and the natural lens or artificial intraocular lens converge at a point behind or in front of the retina and do not converge at a point on the retina. The light rays strike the retina over a larger area than if the light rays converged at a point on the retina. The patient experiences this as blurred vision, particularly for up-close objects such as when reading. For such conditions, the mask 208 of the intraocular lens 200 can be configured with an aperture such that only a subset of light rays, e.g. a central portion, are transmitted to the retina. The mask 208 with an aperture can improve the depth of focus of a human eye. For example, the aperture can be a pin-hole aperture. The mask 208 blocks a portion of the outer light rays resulting in more focused light rays. The mask 208 can include an annular region surrounding an aperture. The aperture can be substantially centrally located on the mask. For example, the aperture can be located around a central axis of the mask, also referred to as the optical axis of the mask. The aperture of the mask can be circular or any other shape.

The mask 208 can be positioned in a variety of locations in or on the intraocular lens 200. The mask 208 can be through the lens body 202. The mask 208 can be positioned on the anterior or posterior surface of the lens body 202. In certain embodiments, the mask 208 is embedded within the lens body. For example, the mask 208 can be positioned substantially at the midway line between the posterior and anterior surfaces of the lens body 202. In certain embodiments, the mask 208 is positioned between the midway line and the posterior surface of the lens body 202. Certain embodiments include the mask 208 being positioned midway, one-third or two-thirds between the midway line and the posterior surface of the lens body 202. In certain other embodiments, the mask 208 is positioned between the midway line and the anterior surface of the lens body 202. Certain embodiments include the mask 208 being positioned midway, one-third or two-thirds between the midway line and the anterior surface of the lens body 202. If the transition zone is on the anterior surface of the implant body and the mask is positioned to be on or near the surface of the transition zone on the anterior surface, the mask may not extend beyond the transition zone since light even at large angles from the optical axis that hits or passes through the transition zone surface would be blocked by the mask.

In certain embodiments, the mask 208 of an intraocular lens 200 has an aperture wherein the mask blocks a portion of the light to improve viewing near objects, similar to a mask discussed above. Advantageously, the mask 208 can provide as an aperture and can block a portion light that may not converging on the retina 956 and also block light that passes through the second portion 220, creating aberrations, as described above. In certain embodiments, the aperture of the mask 208 has a diameter of about 1 to 2 mm. In certain embodiments, the mask 208 has an outer perimeter with a diameter of about 3 to 5 mm.

Figure 9:
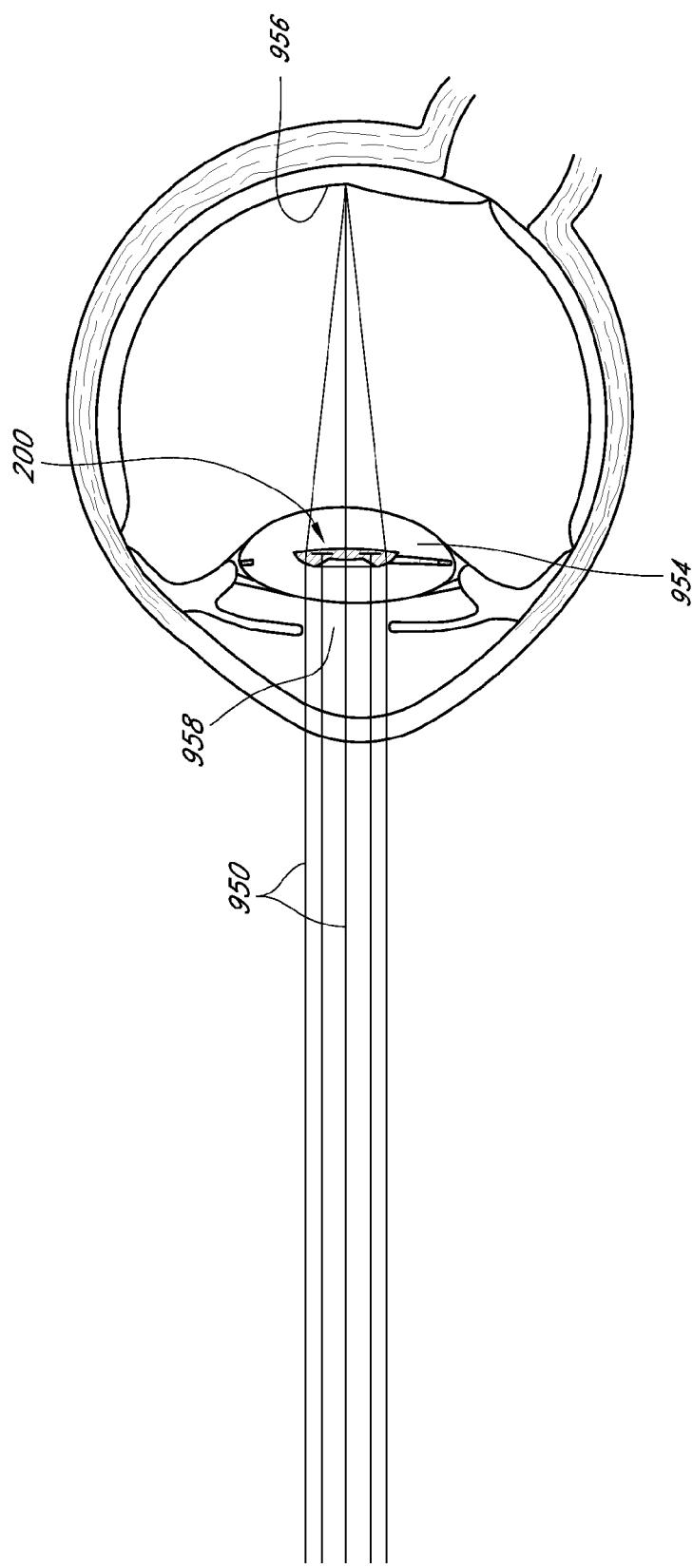
FIG. 9 is a schematic representation of light from a far object transmitted through an eye having an embodiment of an intraocular lens that is in the capsular bag.

In certain embodiments, the third portion 224 of intraocular lens 200 can improve low light vision. As the pupil of the eye enlarges, eventually light rays will enter and pass through the third portion 224 of the intraocular lens 200. As illustrated in FIG. 9, if the pupil 958 of the eye 952 is large enough so that light rays 950 pass through the third portion 224 of the intraocular lens 200, additional light rays 950 will strike the retina. As discussed above, the intraocular lens 200 can have an optical power to correct for viewing far objects so that light rays from a far object are focused at one point on the retina. Near objects during low light conditions may result in an unfocused image if the intraocular lens 200 has an optical power to view far objects.

The mask 208 can have different degrees of opacity. For example, the mask 208 can block substantially all of visible light or may block a portion of visible light. The opacity of the mask 208 may also vary in different regions of the mask 208. In certain embodiments, the opacity of the outer edge and/or the inner edge of the mask 208 is less than the central region of the mask 208. The opacity in different regions may transition abruptly or have a gradient transition. Additional examples of opacity transitions can be found in U.S. Pat. Nos. 5,662,706, 5,905,561 and 5,965,330, which are incorporated in their entirety by reference.

Figure 10B:
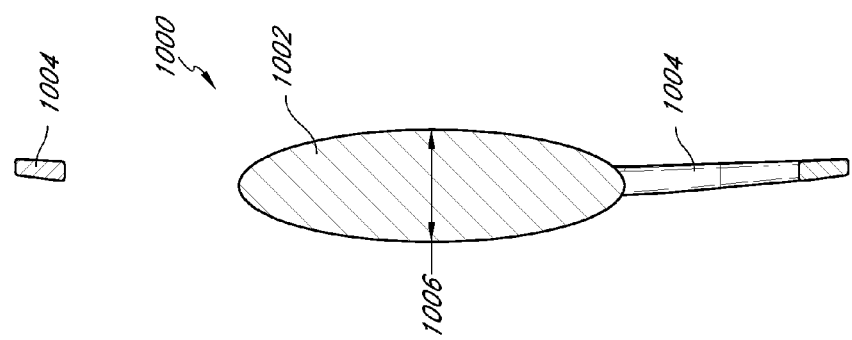
FIG. 10B illustrates a cross-sectional view of the conventional intraocular lens of FIG. 10A.
Figure 10A:
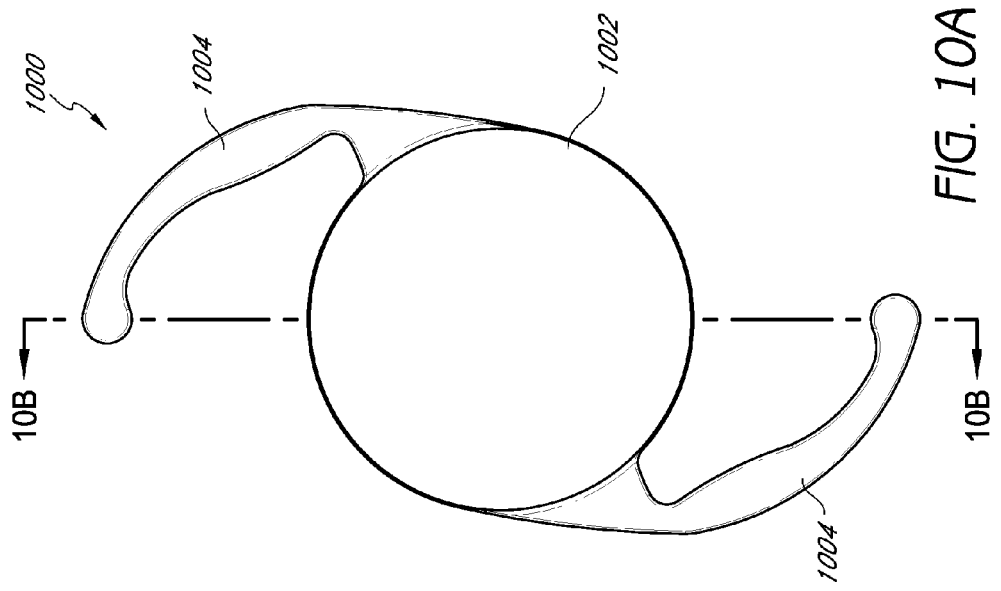
FIG. 10A illustrates a top view of a conventional intraocular lens.

A conventional intraocular lens 1000 is illustrated in FIGS. 10A-B. By having a recessed portion on the posterior surface 310 (created by second portions 314) and/or the anterior surface 312 (created by second portion 320) of the lens body 302, the maximum thickness of the intraocular lens 300 is reduced compared to a conventional lens body 1002 without such portions, as shown in FIG. 10B. The cross-sectional thickness of the lens body 1002 is generally dependent on the optical power of the intraocular lens 1000 and the material of the lens body 1002. In particular, the central region of the lens body 1002 is generally the thickest section of the intraocular lens 1000 with a central region cross-sectional thickness 1006. In certain embodiments disclosed herein, a lens body 202 of an intraocular lens 200 has a central region thickness 206 less than the central region thickness 1006 of other common lens bodies. In the embodiment of FIG. 3B, the thickness 306 is further reduced compared to a conventional intraocular lens 1000.

Generally, as discussed above, intraocular lenses are implanted into the eye by rolling up an intraocular lens and inserting the rolled up intraocular lens into a tube. One advantage to a thinner lens body is that it the intraocular lens can be more tightly rolled up resulting in being able to use a small tube and a small incision. Another advantage to a thinner lens body is that the intraocular lens can decrease risks associated with implanting in different locations within the eye. For example, an intraocular lens 200 can be implanted within the anterior chamber. An intraocular lens 200 can also be positioned within the posterior chamber so that the first portion 216 of the posterior surface 210 floats above the natural crystalline lens. The potential for contact between the posterior surface 210 of the intraocular lens 200 and the natural crystalline lens will be reduced because the reduced thickness of the intraocular lens 200. For example, the intraocular lens 200 can be coupled with or attached to the ciliary sulcus (sometimes referred to herein as "sulcus-fixated"). An intraocular lens 200 can also be implanted in the capsular bag, as illustrated in FIG. 9. Depending on the location of the intraocular lens within the eye, dimensions of the intraocular lens 200 including but not limited to the aperture of the mask 208 may be adjusted.

The intraocular lens 200 and/or the lens body 202 can be made from one or more materials. In certain embodiments, the intraocular lens 200 and/or the lens body 202 can comprise polymers (e.g. PMMA, PVDF, polypropylene, polycarbonate, PEEK, polyethylene, acrylic copolymers, polystyrene, PVC, polysulfone), hydrogels, and silicone.

II. Masks Providing Depth of Focus Correction

Figure 11A:
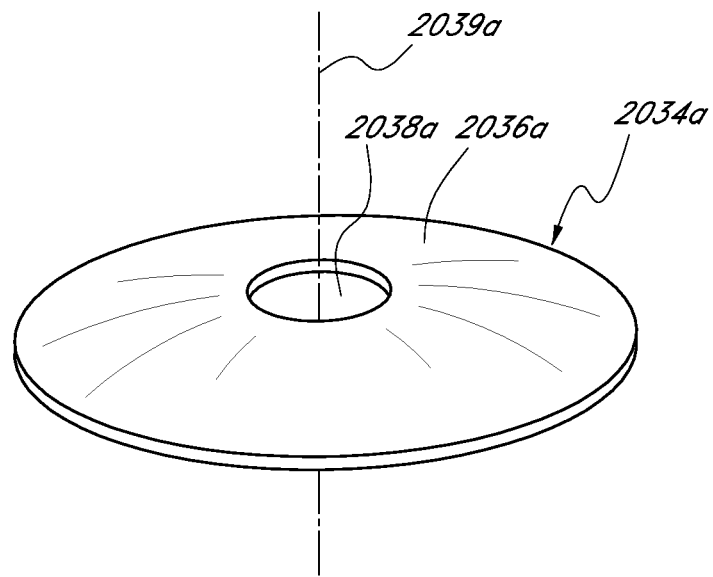
FIG. 11A is a perspective view of one embodiment of a mask.
Figure 11B:
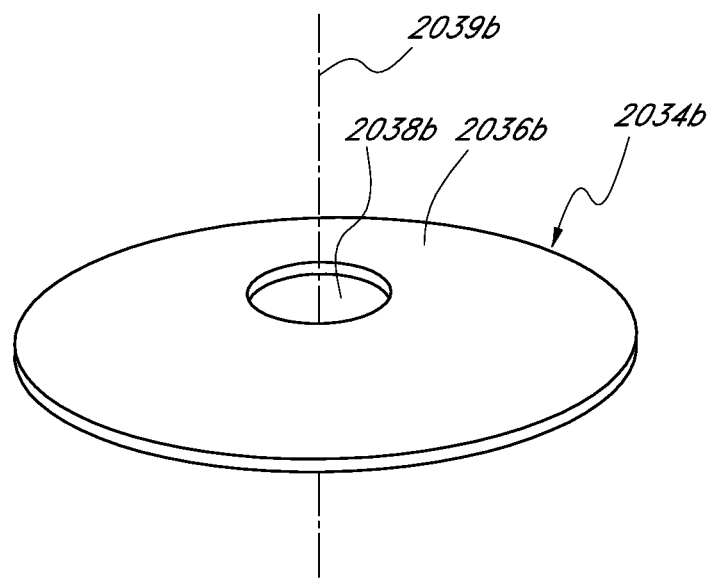
FIG. 11B is a perspective view of an embodiment of a substantially flat mask.

A variety of variations of masks that can be positioned on or within the implant body 2014 are discussed herein, and also described in U.S. Pat. No. 7,628,810, U.S. Patent Publication No. 2006/0113054, and U.S. Patent Publication No. 2006/0265058 which are hereby incorporated by reference in their entirety. FIG. 11A illustrates one embodiment of a mask 2034a. The mask 2034a can include an annular region 2036a surrounding a pinhole opening or aperture 2038a substantially centrally located on the mask 2034a. The pinhole aperture 2038a can be generally located around a central axis 2039a, referred to herein as the optical axis of the mask 2034a. The pinhole aperture 2038a can be in the shape of a circle. FIG. 11B illustrates another embodiment of a mask 2034b similar to the mask 2034a illustrated in FIG. 11A. The annular region 2036a of the mask 2034a of FIG. 11A has a curvature from the outer periphery to the inner periphery of the annular region 2036a; while the annular region 2036b of the mask 2034b of FIG. 11B is substantially flat.

The mask can have dimensions configured to function with the implant body to improve a patient's vision. For example, the thickness of the mask can vary depending on the location of the mask relative to the implant body. For example, if the mask is embedded within the implant body, the mask can have a thickness greater than zero and less than the thickness of the implant body. Alternatively, if the mask is coupled to a surface of the implant body, the mask may preferably have a thickness no greater than necessary to have desired opacity so that the mask does not add additional thickness to the intraocular lens. In certain embodiments, the mask has a thickness of greater than zero and less than about 0.5 mm. In one embodiment, the mask has a thickness of about 0.25 mm. If the mask is on or near the surface of the transition zone, the mask can have a shape similar or the same as the transition zone.

Figure 12:
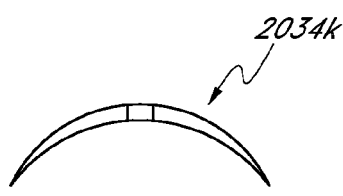
FIG. 12 is a side view of an embodiment of a mask having varying thickness.
Figure 13:
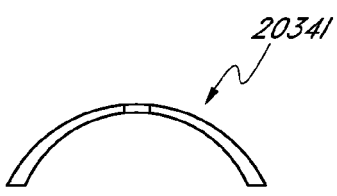
FIG. 13 is a side view of another embodiment of a mask having varying thickness.

The mask may have a constant thickness, as discussed below. However, in some embodiments, the thickness of the mask may vary between the inner periphery (near the aperture 2038) and the outer periphery. FIG. 12 shows a mask 2034k that has a gradually decreasing thickness from the inner periphery to the outer periphery. FIG. 13 shows a mask 2034l that has a gradually increasing thickness from the inner periphery to the outer periphery. Other cross-sectional profiles are also possible.

The annular region 2036 can be at least partially opaque or can be completely opaque. The degree of opacity of the annular region 2036 prevents at least some or substantially all light from being transmitted through the mask 2032. Opacity of the annular region 2036 may be achieved in any of several different ways.

For example, in one embodiment, the material used to make mask 2034 may be naturally opaque. Alternatively, the material used to make the mask 2034 may be substantially clear, but treated with a dye or other pigmentation agent to render region 2036 substantially or completely opaque. In still another example, the surface of the mask 2034 may be treated physically or chemically (such as by etching) to alter the refractive and transmissive properties of the mask 2034 and make it less transmissive to light.

Figure 14:
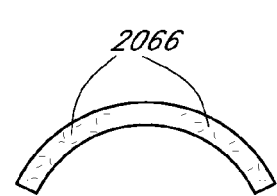
FIG. 14 is a side view of an embodiment of a mask with a material to provide opacity to the mask.

In still another alternative, the surface of the mask 2034 may be treated with a particulate deposited thereon. For example, the surface of the mask 2034 may be deposited with particulate of titanium, gold or carbon to provide opacity to the surface of the mask 2034. In another alternative, the particulate may be encapsulated within the interior of the mask 2034, as generally shown in FIG. 14. Finally, the mask 2034 may be patterned to provide areas of varying light transmissivity.

In another embodiment, the mask may be formed from co-extruded rods made of material having different light transmissive properties. The co-extruded rod may then be sliced to provide disks for a plurality of masks, such as those described herein.

Other embodiments employ different ways of controlling the light transmissivity through a mask. For example, the mask may be a gel-filled disk, as shown in FIG. 14. The gel may be a hydrogel or collagen, or other suitable material that is biocompatible with the mask material and can be introduced into the interior of the mask. The gel within the mask may include particulate 2066 suspended within the gel. Examples of suitable particulate are gold, titanium, and carbon particulate, which, as discussed above, may alternatively be deposited on the surface of the mask.

The material of the mask 2034 may be any polymeric material. Where the mask 2034 is applied to the intraocular implant, the material of the mask 2034 should be biocompatible. Where a gel is used, the material is suitable for holding a gel. Examples of suitable materials for the mask 2034 include the preferred polymethylmethacrylate or other suitable polymers or co-polymers, such as hydrogels, and the like. Of course, as indicated above, for non-gel-filled materials, a preferred material may be a fibrous material, such as a Dacron mesh.

Figure 15:
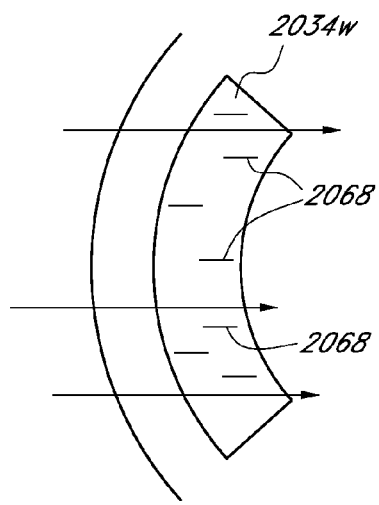
FIG. 15 is an enlarged, diagrammatic view of an embodiment of a mask that includes particulate structure adapted for selectively controlling light transmission through the mask in a low light environment.
Figure 16:
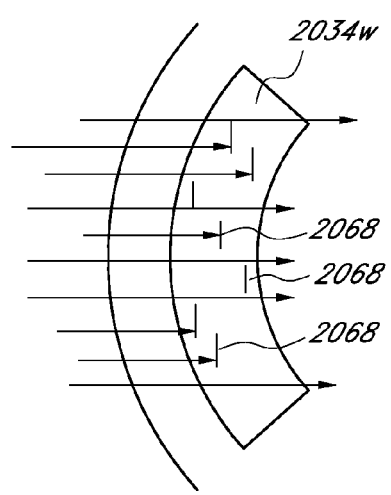
FIG. 16 is a view of the mask of FIG. 15 in a bright light environment.

FIGS. 15 and 16 illustrate one embodiment where a mask 2034w comprises a plurality of nanites 2068. "Nanites" are small particulate structures that have been adapted to selectively transmit or block light entering the eye of the patient. The particles may be of a very small size typical of the particles used in nanotechnology applications. The nanites 2068 are suspended in the gel or otherwise inserted into the interior of the mask 2034w, as generally shown in FIGS. 15 and 16. The nanites 2068 can be preprogrammed to respond to different light environments.

Thus, as shown in FIG. 15, in a high light environment, the nanites 2068 turn and position themselves to substantially and selectively block some of the light from entering the eye. However, in a low light environment where it is desirable for more light to enter the eye, nanites may respond by turning or be otherwise positioned to allow more light to enter the eye, as shown in FIG. 16.

Nano-devices or nanites are crystalline structures grown in laboratories. The nanites may be treated such that they are receptive to different stimuli such as light. In accordance with one aspect of certain embodiments, the nanites can be imparted with energy where, in response to a low light and high light environments, they rotate in the manner described above and generally shown in FIG. 16.

Nanoscale devices and systems and their fabrication are described in Smith et al., "Nanofabrication," Physics Today, February 1990, pp. 24-30 and in Craighead, "Nanoelectromechanical Systems," Science, Nov. 24, 2000, Vol. 290, pp. 1502-1505, both of which are incorporated by reference herein in their entirety. Tailoring the properties of small-sized particles for optical applications is disclosed in Chen et al. "Diffractive Phase Elements Based on Two-Dimensional Artificial Dielectrics," Optics Letters, Jan. 15, 1995, Vol. 20, No. 2, pp. 121-123, also incorporated by reference herein in its entirety.

In additional embodiments, a photochromic material can be used as the mask or in addition to mask. Under bright light conditions, the photochromic material can darken thereby creating a mask and enhancing near vision. Under dim light conditions, the photochromic lightens, which allows more light to pass through to the retina. In certain embodiments, under dim light conditions, the photochromic lightens to expose an optic of the intraocular implant.

The mask can have different degrees of opacity. For example, the mask can block substantially all of visible light or may block a portion of visible light. The opacity of the mask may also vary in different regions of the mask. In certain embodiments, the opacity of the outer edge and/or the inner edge of the mask is less than the central region of the mask. The opacity in different regions may transition abruptly or have a gradient transition. Additional examples of opacity transitions can be found in U.S. Pat. Nos. 5,662,706, 5,905,561 and 5,965,330, which are incorporated in their entirety by reference.

Figure 17:
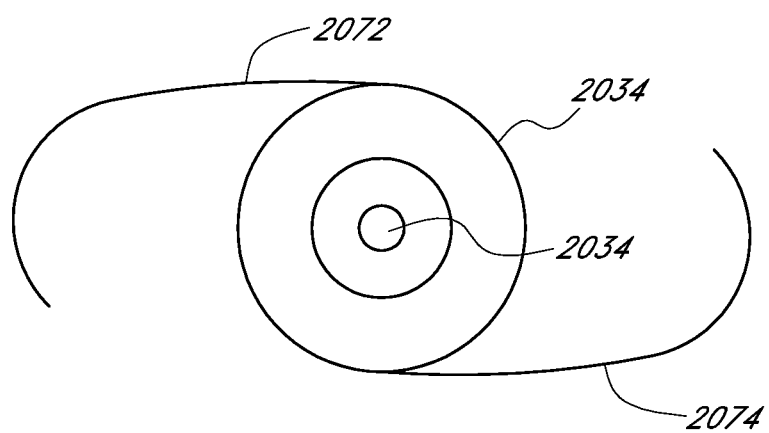
FIG. 17 is another embodiment of a mask that includes connectors for securing the mask within the eye.

In some embodiments, the mask 2034 is attached or fixed to the eye 2010 by support strands 2072 and 2074 shown in FIG. 17 and generally described in U.S. Pat. No. 4,976,732, incorporated by reference herein in its entirety.

Further mask details are disclosed in U.S. Pat. No. 4,976,732, issued Dec. 11, 1990 and in U.S. patent application Ser. No. 10/854,033, filed May 26, 2004, both of which are incorporated by reference herein in their entirety.

An advantage to embodiments that include a mask with an aperture (e.g., pin-hole aperture) described herein over multifocal IOLs, contact lenses, or treatments of the cornea is that all of these latter approaches divide the available light coming through the aperture into two or more foci while a mask approach has a single focus (monofocal). This limitation forces designers of multifocal optics to choose how much of the light is directed to each focal point, and to deal with the effects of the unfocused light that is always present in any image. In order to maximize acuity at the important distances of infinity (>6M) and 40 cm (normal reading distance), it is typical to provide little or no light focused at an intermediate distance, and as a result, visual acuity at these distances is poor.

Figure 59:
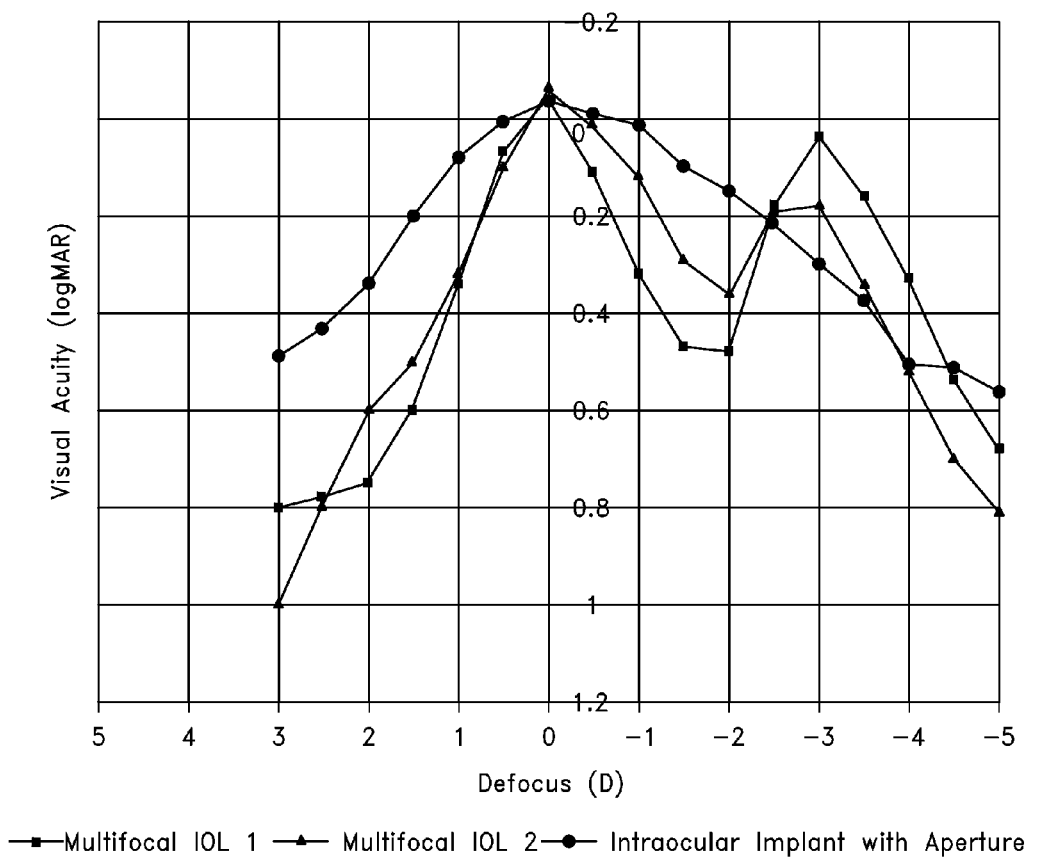
FIG. 59 is a plot of visual acuity as a function of defocus comparing two typical multifocal IOLs and an embodiment of an ophthalmic device with an aperture described herein.

With an aperture to increase depth-of-focus, however, the intermediate vision of presbyopic patient is improved significantly. Indeed, the defocus blur with the pin-hole aperture is less at intermediate distances than at near. This can be seen in FIG. 59 which is a plot of visual acuity as a function of defocus comparing an embodiment of an ophthalmic device with an aperture and with two commercially available multifocal IOLs. While greater visual acuity is obtained with the multifocal IOLs at very close distances (33 cm, −3 D), over the range of 1M (−1 D) to 40 cm (−2.5 D), the pin-hole aperture can outperform a multifocal optic in an intermediate range.

Visual acuity is measured in log MAR and is the log of the minimum angle of resolution or the smallest angular spacing that can be seen, and it is independent of viewing distance. A log MAR value of 0 means 20/20, 6/6, or a decimal acuity of 1 at distance, and equivalent to a near acuity of Jaeger 1 (J1). Defocus is measured in diopters, which are the reciprocal of the eye's focal length in meters. Thus, −1 D defocus means the eye is focused at 1/1=1 meter. The standard (US and Europe) reading distance is 40 cm, which is −2.5 D of defocus (1/0.4=2.5).

III. UV-Resistant Polymeric Mask Materials

Because the mask has a very high surface to volume ratio and is exposed to a great deal of sunlight following implantation, the mask preferably comprises a material which has good resistance to degradation, including from exposure to ultraviolet (UV) or other wavelengths of light. Polymers including a UV absorbing component, including those comprising UV absorbing additives or made with UV absorbing monomers (including co-monomers), may be used in forming masks as disclosed herein which are resistant to degradation by UV radiation. Examples of such polymers include, but are not limited to, those described in U.S. Pat. Nos. 4,985,559 and 4,528,311, the disclosures of which are hereby incorporated by reference in their entireties. In a preferred embodiment, the mask comprises a material which itself is resistant to degradation by UV radiation. In one embodiment, the mask comprises a polymeric material which is substantially reflective of or transparent to UV radiation. The lens body may include a UV absorbing component in addition to the mask being resistant to degradation by UV radiation or the mask may not be resistant to degradation by UV radiation since the UV absorbing component in the lens body may prevent degradation of the mask by UV radiation.

Alternatively, the mask may include a component which imparts a degradation resistive effect, or may be provided with a coating, preferably at least on the anterior surface, which imparts degradation resistance. Such components may be included, for example, by blending one or more degradation resistant polymers with one or more other polymers. Such blends may also comprise additives which provide desirable properties, such as UV absorbing materials. In one embodiment, blends preferably comprise a total of about 1-20 wt. %, including about 1-10 wt. %, 5-15 wt. %, and 10-20 wt. % of one or more degradation resistant polymers. In another embodiment, blends preferably comprise a total of about 80-100 wt. %, including about 80-90 wt. %, 85-95 wt. %, and 90-100 wt. % of one or more degradation resistant polymers. In another embodiment, the blend has more equivalent proportions of materials, comprising a total of about 40-60 wt. %, including about 50-60 wt. %, and 40-50 wt. % of one or more degradation resistant polymers. Masks may also include blends of different types of degradation resistant polymers, including those blends comprising one or more generally UV transparent or reflective polymers with one or more polymers incorporating UV absorption additives or monomers. These blends include those having a total of about 1-20 wt. %, including about 1-10 wt. %, 5-15 wt. %, and 10-20 wt. % of one or more generally UV transparent polymers, a total of about 80-100 wt. %, including about 80-90 wt. %, 85-95 wt. %, and 90-100 wt. % of one or more generally UV transparent polymers, and a total of about 40-60 wt. %, including about 50-60 wt. %, and 40-50 wt. % of one or more generally UV transparent polymers. The polymer or polymer blend may be mixed with other materials as discussed below, including, but not limited to, opacification agents, polyanionic compounds and/or wound healing modulator compounds. When mixed with these other materials, the amount of polymer or polymer blend in the material which makes up the mask is preferably about 50%-99% by weight, including about 60%-90% by weight, about 65-85% by weight, about 70-80% by weight, and about 90-99% by weight.

Preferred degradation resistant polymers include halogenated polymers. Preferred halogenated polymers include fluorinated polymers, that is, polymers having at least one carbon-fluorine bond, including highly fluorinated polymers. The term "highly fluorinated" as it is used herein, is a broad term used in its ordinary sense, and includes polymers having at least one carbon-fluorine bond (C—F bond) where the number of C—F bonds equals or exceeds the number of carbon-hydrogen bonds (C—H bonds). Highly fluorinated materials also include perfluorinated or fully fluorinated materials, materials which include other halogen substituents such as chlorine, and materials which include oxygen- or nitrogen-containing functional groups. For polymeric materials, the number of bonds may be counted by referring to the monomer(s) or repeating units which form the polymer, and in the case of a copolymer, by the relative amounts of each monomer (on a molar basis).

Preferred highly fluorinated polymers include, but are not limited to, polytetrafluoroethylene (PFTE or Teflon®), polyvinylidene fluoride (PVDF or Kynar®), poly-1,1,2-trifluoroethylene, and perfluoroalkoxyethylene (PFA). Other highly fluorinated polymers include, but are not limited to, homopolymers and copolymers including one or more of the following monomer units: tetrafluoroethylene —(CF2-CF2)-; vinylidene fluoride —(CF2-CH2)-; 1,1,2-trifluoroethylene —(CF2-CHF)—; hexafluoropropene —(CF(CF3)-CF2)-; vinyl fluoride —(CH2-CHF)— (homopolymer is not "highly fluorinated"); oxygen-containing monomers such as —(O—CF2)-, —(O—CF2-CF2)-, —(O—CF(CF3)-CF2)-; chlorine-containing monomers such as —(CF2-CFCl)—. Other fluorinated polymers, such as fluorinated polyimide and fluorinated acrylates, having sufficient degrees of fluorination are also contemplated as highly fluorinated polymers for use in masks according to preferred embodiments. The homopolymers and copolymers described herein are available commercially and/or methods for their preparation from commercially available materials are widely published and known to those in the polymer arts.

Although highly fluorinated polymers are preferred, polymers having one or more carbon-fluorine bonds but not falling within the definition of "highly fluorinated" polymers as discussed above, may also be used. Such polymers include co-polymers formed from one or more of the monomers in the preceding paragraph with ethylene, vinyl fluoride or other monomer to form a polymeric material having a greater number of C—H bonds than C—F bonds. Other fluorinated polymers, such as fluorinated polyimide, may also be used. Other materials that could be used in some applications, alone or in combination with a fluorinated or a highly fluorinated polymer, are described in U.S. Pat. No. 4,985,559 and in U.S. Pat. No. 4,528,311, both of which are hereby incorporated by reference herein in their entirety.

The preceding definition of highly fluorinated is best illustrated by means of a few examples. One preferred UV-resistant polymeric material is polyvinylidene fluoride (PVDF), having a structure represented by the formula: —(CF2-CH2)n-. Each repeating unit has two C—H bonds, and two C—F bonds. Because the number of C—F bonds equals or exceeds the number of C—H bonds, PVDF homopolymer is a "highly fluorinated" polymer. Another material is a tetrafluoroethylene/vinyl fluoride copolymer formed from these two monomers in a 2:1 molar ratio. Regardless of whether the copolymer formed is block, random or any other arrangement, from the 2:1 tetrafluoroethylene:vinyl fluoride composition one can presume a "repeating unit" comprising two tetrafluoroethylene units, each having four C—F bonds, and one vinyl fluoride unit having three C—H bonds and one C—F bond. The total bonds for two tetrafluoroethylenes and one vinyl fluoride are nine C—F bonds, and three C—H bonds. Because the number of C—F bonds equals or exceeds the number of C—H bonds, this copolymer is considered highly fluorinated.

Certain highly fluorinated polymers, such as PVDF, have one or more desirable characteristics, such as being relatively chemically inert and having a relatively high UV transparency as compared to their non-fluorinated or less highly fluorinated counterpart polymers. Although the applicant does not intend to be bound by theory, it is postulated that the electronegativity of fluorine may be responsible for many of the desirable properties of the materials having relatively large numbers of C—F bonds.

In preferred embodiments, at least a portion of the highly fluorinated polymer material forming the mask comprises an opacification agent which imparts a desired degree of opacity. In one embodiment, the opacification agent provides sufficient opacity to produce the depth of field improvements described herein, e.g., in combination with a transmissive aperture. In one embodiment, the opacification agent renders the material opaque. In another embodiment, the opacification agent prevents transmission of about 90 percent or more of incident light. In another embodiment, the opacification agent renders the material opaque. In another embodiment, the opacification agent prevents transmission of about 80 percent or more of incident light. Preferred opacification agents include, but are not limited to organic dyes and/or pigments, preferably black ones, such as azo dyes, hematoxylin black, and Sudan black; inorganic dyes and/or pigments, including metal oxides such as iron oxide black and ilminite, silicon carbide and carbon (e.g. carbon black, submicron powdered carbon). The foregoing materials may be used alone or in combination with one or more other materials. The opacification agent may be applied to one or more surfaces of the mask on all or some of the surface, or it may be mixed or combined with the polymeric material (e.g. blended during the polymer melt phase). Although any of the foregoing materials may be used, carbon has been found to be especially useful in that it does not fade over time as do many organic dyes, and that it also aids the UV stability of the material by absorbing UV radiation. In one embodiment, carbon may be mixed with polyvinylidene fluoride (PVDF) or other polymer composition comprising highly fluorinated polymer such that the carbon comprises about 2% to about 20% by weight of the resulting composition, including about 10% to about 15% by weight, including about 12%, about 13%, and about 14% by weight of the resulting composition.

Some opacification agents, such as pigments, which are added to blacken, darken or opacify portions of the mask may cause the mask to absorb incident radiation to a greater degree than mask material not including such agents. Because the matrix polymer that carries or includes the pigments may be subject to degradation from the absorbed radiation, it is preferred that the mask, which is thin and has a high surface area making it vulnerable to environmental degradation, be made of a material which is itself resistant to degradation such as from UV radiation, or that it be generally transparent to or non-absorbing of UV radiation. Use of a highly UV resistant and degradation resistant material, such as PVDF, which is highly transparent to UV radiation, allows for greater flexibility in choice of opacification agent because possible damage to the polymer caused by selection of a particular opacification agent is greatly reduced.

A number of variations of the foregoing embodiments of degradation resistant constructions are contemplated. In one variation, a mask is made almost exclusively of a material that is not subject to UV degradation. For example, the mask can be made of a metal, a highly fluorinated polymer, carbon (e.g., graphene, pure carbon), or another similar material. Construction of the mask with metal is discussed in more detail in U.S. application Ser. No. 11/000,562 filed Dec. 1, 2004 and entitled "Method of Making an Ocular Implant" and also in U.S. application Ser. No. 11/107,359 filed Apr. 14, 2005 with the title "Method of Making an Ocular Implant", both of which are incorporated herein in their entirety by reference. As used in this context, "exclusively" is a broad term that allows for the presence of some non-functional materials (e.g., impurities) and for an opacification agent, as discussed above. In other embodiments, the mask can include a combination of materials. For example, in one variation, the mask is formed primarily of any implantable material and is coated with a UV resistant material. In another variation, the mask includes one or more UV degradation inhibitors and/or one or more UV degradation resistant polymers in sufficient concentration such that the mask under normal use conditions will maintain sufficient functionality in terms of degradation to remain medically effective for at least about 5 years, preferably at least about 10 years, and in certain implementations at least about 20 years.

Figure 23:
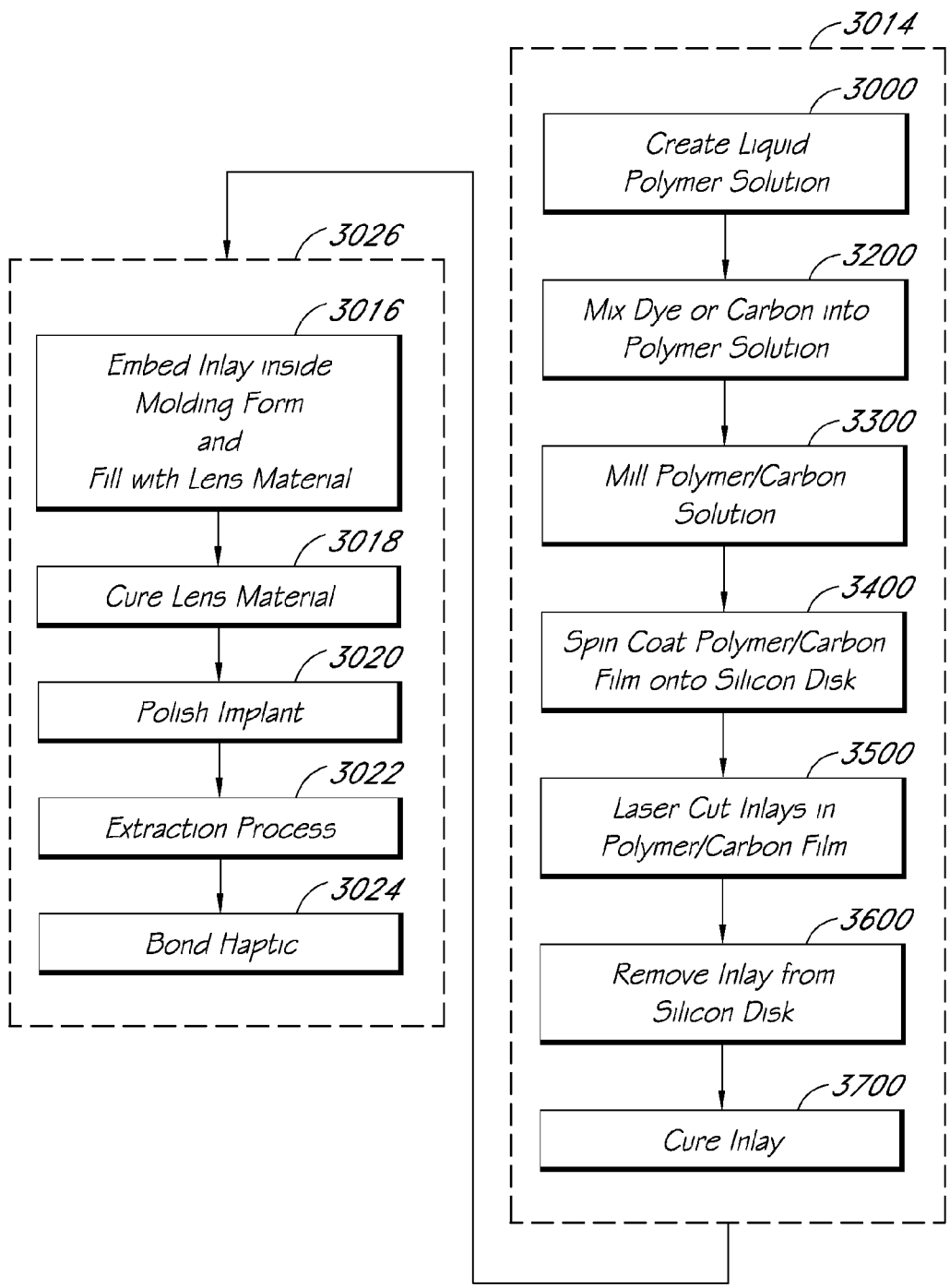
FIG. 23 is a flow chart illustrating one method for making a masked intraocular implant from a mask comprising a highly fluorinated polymer and an opacification agent.

FIG. 23 is a flow chart illustrating methods for making a masked intraocular implant from a mask comprising a highly fluorinated polymer and an opacification agent. The method of FIG. 23 includes a first method 3014 of making a mask of highly fluorinated polymer and opacification agent and a second method 3026 of making an intraocular implant with the mask made from the first method 3014.

At step 3000, a liquid form of a polymer is created by dissolving polyvinylidene fluoride (PVDF) pellets into a solvent such as dimethyl acetamide (DMAC or DMA) using heat until the PVDF has completely dissolved. In one embodiment, the solution may be mixed for a minimum of 12 hours to ensure that the PVDF has completely dissolved. At step 3200, the PVDF/DMAC solution is mixed with an opacification agent, such as a dye or carbon black, using a high speed shear mixer. In one embodiment, the carbon black comprises 13% by weight of the resulting composition while the PVDF comprises 87% by weight of the resulting composition. At step 3300, the PVDF/carbon black solution is optionally milled in a high speed mill, for example an Eiger high speed mill, to break up any large carbon agglomerates in the solution. The PVDF/carbon black solution may be run through the mill a second time to further break up any carbon agglomerates. At step 3400, the resulting solution is applied to a silicon wafer to create a polymer film on the silicon disk. Here, approximately 55 g of the PVDF/carbon black solution is poured into a dispensing barrel for application on a silicon wafer. The silicon disk is placed on the spinner of a spin casting machine and the dispensing barrel is used to apply a bead of PVDF/carbon black solution to the silicon wafer in a circular pattern, leaving the center 1" diameter of the disk empty. The spinner cycle is actuated to disperse the PVDF/carbon black solution over the disk, forming a uniform 10 micron thick film. A polymer film may also be deposited, spray coated, etc. to a silicon wafer. The coated silicon disk is then placed on a hot-plate to evaporate the DMAC. At step 3500, the coated silicon wafer is placed under an excimer laser. A laser cutting mask is mounted in the laser and the laser is actuated. Using the laser cutting mask, approximately 150 mask patterns are laser machined into the PVDF/carbon black film. The mask patterns may also be formed using a punch technique, electron beam, etch, etc. The mask patterns are arranged such that the material extending approximately 5 mm from the edge of the silicon disk is not used. During the laser machining, the silicon disk may be bathed in nitrogen gas in order to cool the surface. At step 3600, the laser machined masks are removed from the silicon disk using a razor blade. An optional step may include placing the laser-machined mask into a forming mold. The mold can be any shape desired, such as a flat mold, a convex mold, a concave mold, or a mold with a more complex shape. The mask may be placed in the bottom half of the forming mold in one technique. The top half of the forming mold can be placed on top of the mask and the molds can be placed in an oven at about 160° C. The molds are then heated and baked to form the masks. The molds are allowed to bake for approximately two hours at approximately 160° C. After two hours the oven temperature is reduced to about 30° C. and the masks are baked for approximately two hours or until the oven temperature has dropped to below around 40° C.

At step 3016, the inlay (e.g. mask) made in the first method 3014 is placed in a mold form. In one embodiment, silicone or other lens material is injected into the mold form and around the inlay. At step 3018, the silicone is cured to form an implant body. At step 3020, the intraocular implant is polished, and at step 3022, the implant body is extracted from the mold form. At step 3024, one or more haptics may be attached (e.g. bonded) to the implant body to form an intraocular implant. Step 3024 may be included for a three piece IOL design, but may not be needed for other designs. In certain embodiments, the one or more haptics are formed with the implant body during the injection process. For example, the implant body may be lathed and the haptics milled from a single piece. The intraocular implant can be subsequently inspected (e.g. cosmetic, diopter, resolution).

IV. Masks Configured to Reduce Visible Diffraction Patterns

Many of the foregoing masks can be used to improve the depth of focus of a patient. Various additional mask embodiments are discussed below. Some of the embodiments described below include light transmission holes through the mask annular region to change the amount of light blocked by the annular region. Light transmission holes through the mask can improve a patient's dim or low light vision. In certain arrangements of light transmission holes, the light transmission holes may generate diffraction patterns that interfere with the vision improving effect of the masks described herein. Accordingly, certain masks are described herein that include light transmission holes that do not generate diffraction patterns or otherwise interfere with the vision enhancing effects of the mask embodiments.

Figure 18A:
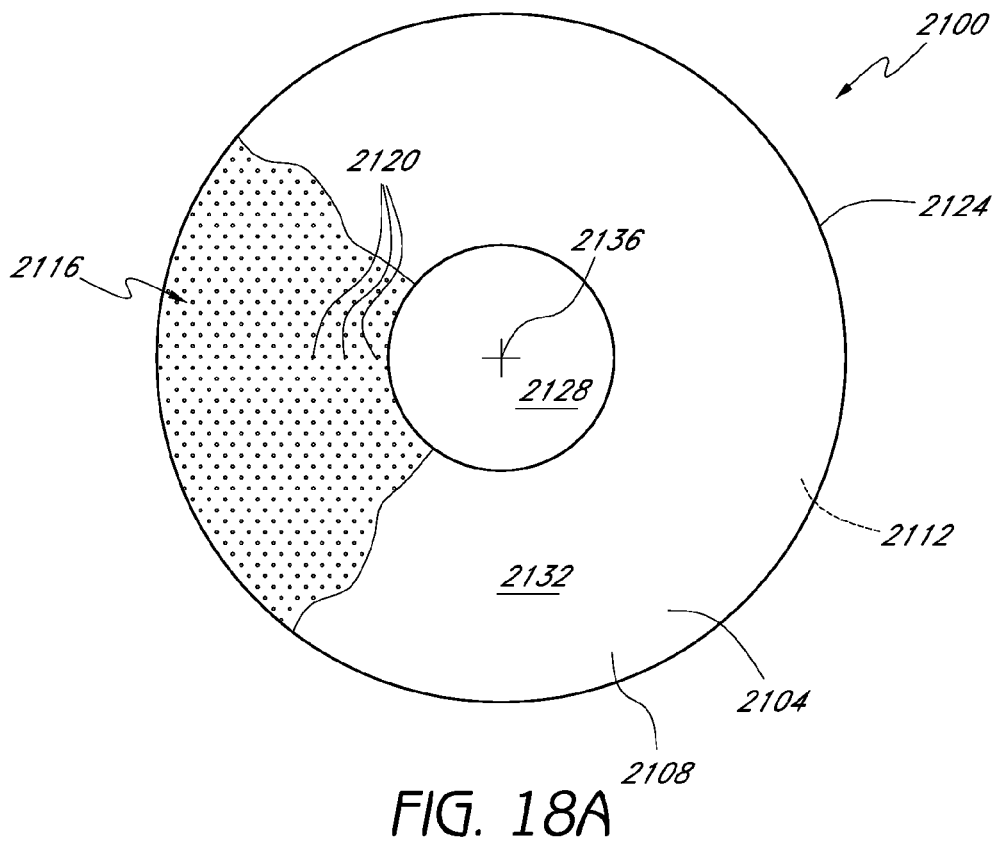
FIG. 18A is a top view of another embodiment of a mask configured to increase depth of focus.
Figure 18B:
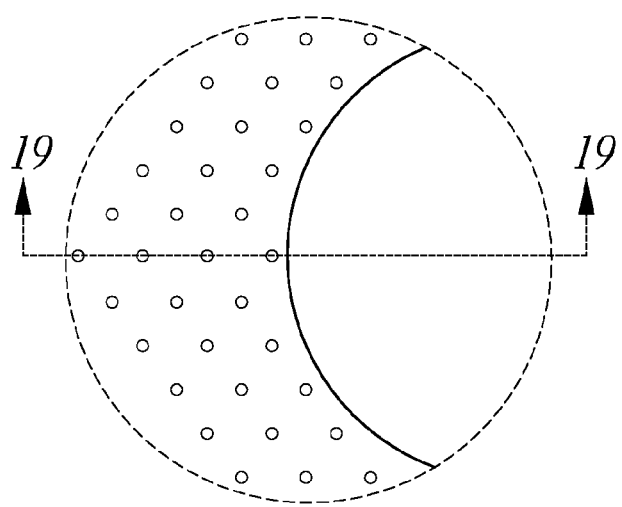
FIG. 18B is an enlarged view of a portion of the view of FIG. 18A.
Figure 19:
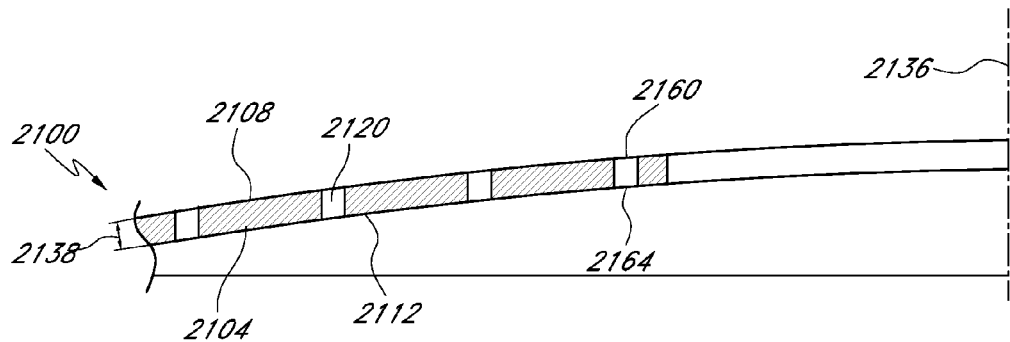
FIG. 19 is a cross-sectional view of the mask of FIG. 18B taken along the section plane 19-19.

FIGS. 18-19 show one embodiment of a mask 2100 configured to increase depth of focus of an eye of a patient with presbyopia. The mask 2100 is similar to the masks hereinbefore described, except as described differently below. The mask 2100 can be made of the materials discussed herein, including those discussed above. Also, the mask 2100 can be formed by any suitable process. The mask 2100 is configured to be applied to an IOL.

In one embodiment, the mask 2100 includes a body 2104 that has an anterior surface 2108 and a posterior surface 2112. The body 2104 may be formed of any suitable material, including at least one of an open cell foam material, an expanded solid material, and a substantially opaque material. In one embodiment, the material used to form the body 2104 has relatively high water content. In other embodiments, the materials that can be used to form the body 2104 include polymers (e.g. PMMA, PVDF, polypropylene, polycarbonate, PEEK, polyethylene, acrylic copolymers (e.g., hydrophobic or hydrophilic), polystyrene, PVC, polysulfone), hydrogels, silicone, metals, metal alloys, or carbon (e.g., graphene, pure carbon).

Figure 20A:
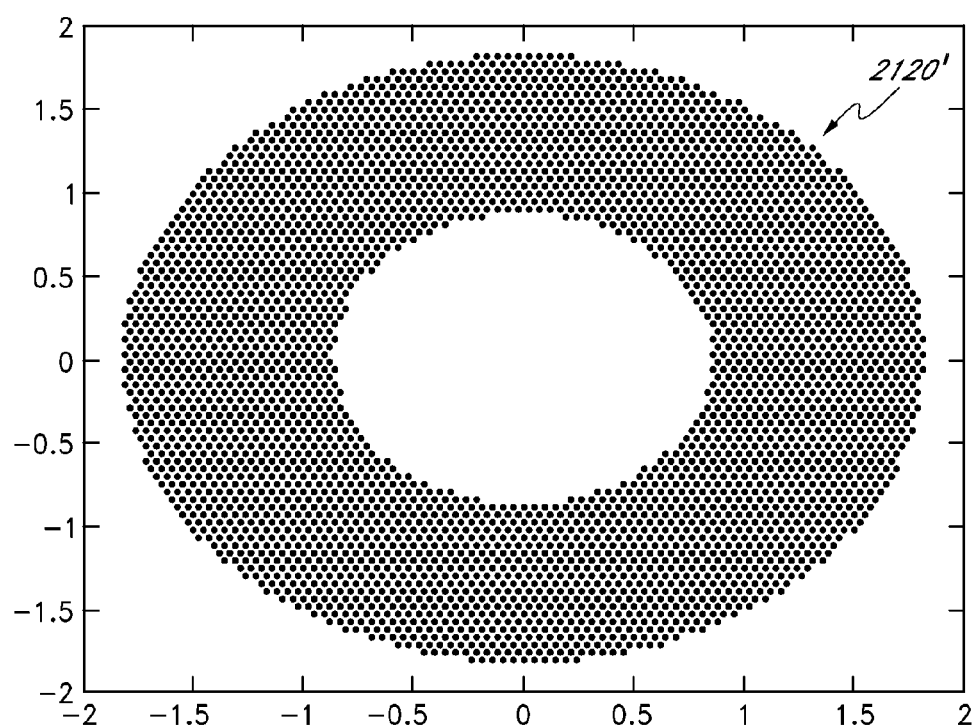
FIG. 20A is a graphical representation of one arrangement of holes of a plurality of holes that may be formed on the mask of FIG. 18A.

In one embodiment, the mask 2100 includes a light transmission hole arrangement 2116. The light transmission hole arrangement 2116 may comprise a plurality of holes 2120. The holes 2120 are shown on only a portion of the mask 2100, but the holes 2120 preferably are located throughout the body 2104 in one embodiment. In one embodiment, the holes 2120 are arranged in a hex pattern, which is illustrated by a plurality of locations 2120' in FIG. 20A. As discussed below, a plurality of locations may be defined and later used in the later formation of a plurality of holes 2120 on the mask 2100. The mask 2100 has an outer periphery 2124 that defines an outer edge of the body 2104. In some embodiments, the mask 2100 includes an aperture 2128 at least partially surrounded by the outer periphery 2124 and a non-transmissive portion 2132 located between the outer periphery 2124 and the aperture 2128.

Preferably the mask 2100 is symmetrical, e.g., symmetrical about a mask axis 2136. In one embodiment, the outer periphery 2124 of the mask 2100 is circular. The mask in general has a diameter within the range of from about 3 mm to about 8 mm, often within the range of from about 3.5 mm to about 6 mm, and less than about 6 mm in one embodiment. In another embodiment, the mask is circular and has a diameter in the range of 4 to 6 mm. In another embodiment, the mask 2100 is circular and has a diameter of less than 4 mm. The outer periphery 2124 has a diameter of about 3.8 mm in another embodiment. In some embodiments, masks that are asymmetrical or that are not symmetrical about a mask axis provide benefits, such as enabling a mask to be located or maintained in a selected position with respect to the anatomy of the eye.

The body 2104 of the mask 2100 may be configured to be coupled with a particular intraocular lens design, either of reduced thickness design or of conventional design. For example, where the mask 2100 is to be coupled with a particular IOL that has curvature, the body 2104 may be provided with a corresponding amount of curvature along the mask axis 2136 that corresponds to the curvature. Likewise, the body 2104 may be provided with corresponding shape to accommodate IOL transition zones.

In some embodiments, the mask 2100 has a desired amount of optical power. Optical power may be provided by configuring the at least one of the anterior and posterior surfaces 2108, 2112 with curvature. In one embodiment, the anterior and posterior surfaces 2108, 2112 are provided with different amounts of curvature. In this embodiment, the mask 2100 has varying thickness from the outer periphery 2124 to the aperture 2128.

In one embodiment, one of the anterior surface 2108 and the posterior surface 2112 of the body 2104 is substantially planar. In one planar embodiment, very little or no uniform curvature can be measured across the planar surface. In another embodiment, both of the anterior and posterior surfaces 2108, 2112 are substantially planar. In general, the thickness of the body 2104 of the mask 2100 may be within the range of from greater than zero to about 0.5 mm. In another embodiment, the thickness 2138 of the mask 2100 is about 0.25 mm. [0201] A substantially planar mask has several advantages over a non-planar mask. For example, a substantially planar mask can be fabricated more easily than one that has to be formed to a particular curvature. In particular, the process steps involved in inducing curvature in the mask 2100 can be eliminated.

The aperture 2128 is configured to transmit substantially all incident light along the mask axis 2136. The non-transmissive portion 2132 surrounds at least a portion of the aperture 2128 and substantially prevents transmission of incident light thereon. As discussed in connection with the above masks, the aperture 2128 may be a through-hole in the body 2104 or a substantially light transmissive (e.g., transparent) portion thereof. The aperture 2128 of the mask 2100 generally is defined within the outer periphery 2124 of the mask 2100. The aperture 2128 may take any of suitable configurations, such as those described above.

In one embodiment, the aperture 2128 is substantially circular and is substantially centered in the mask 2100. The size of the aperture 2128 may be any size that is effective to increase the depth of focus of an eye of a patient suffering from presbyopia. In particular, the size of the aperture 2128 is dependent on the location of the mask within the eye (e.g., distance from the retina). For example, in the intraocular space of the eye, the aperture 2128 can be circular, having a diameter of less than about 2 mm in one embodiment. In another embodiment, the diameter of the aperture is between about 1.1 mm and about 1.6 mm. In another embodiment, the aperture 2128 is circular and has a diameter of about 1.6 mm or less. In a further embodiment, the diameter of the aperture is about mm. Most apertures will have a diameter within the range of from about 0.85 mm to about 2.2 mm, and often within the range of from about 1.1 mm to about 1.7 mm.

In certain embodiments, the aperture 2128 includes an optical power and/or refractive properties. For example, the aperture 2128 can include an optic and can have an optical power (e.g. positive or negative optical power). In certain embodiments, the aperture 2128 can correct for refractive errors of an eye.

The non-transmissive portion 2132 is configured to prevent transmission of radiant energy through the mask 2100. For example, in one embodiment, the non-transmissive portion 2132 prevents transmission of substantially all of at least a portion of the spectrum of the incident radiant energy. In one embodiment, the non-transmissive portion 2132 is configured to prevent transmission of substantially all visible light, e.g., radiant energy in the electromagnetic spectrum that is visible to the human eye. The non-transmissive portion 2132 may substantially prevent transmission of radiant energy outside the range visible to humans in some embodiments.

As discussed above, preventing transmission of light through the non-transmissive portion 2132 decreases the amount of light that reaches the retina and the fovea that would not converge at the retina and fovea to form a sharp image. As discussed above, the size of the aperture 2128 is such that the light transmitted therethrough generally converges at the retina or fovea. Accordingly, a much sharper image is presented to the eye than would otherwise be the case without the mask 2100.

In one embodiment, the non-transmissive portion 2132 prevents transmission of at least about 90 percent of incident light. In another embodiment, the non-transmissive portion 2132 prevents transmission of at least about 95 percent of all incident light. The non-transmissive portion 2132 of the mask 2100 may be configured to be substantially opaque to prevent the transmission of light. As used herein the term "opaque" is intended to indicate a transmission of no more than about 2% of incident visible light. In one embodiment, at least a portion of the body 2104 is configured to be opaque to more than 99 percent of the light incident thereon.

As discussed above, the non-transmissive portion 2132 may be configured to prevent transmission of light without absorbing the incident light. For example, the mask 2100 could be made reflective or could be made to interact with the light in a more complex manner, as discussed in U.S. Pat. No. 6,554,424, issued Apr. 29, 2003, which is hereby incorporated by reference herein in its entirety.

As discussed above, the mask 2100 also has light transmission holes that in some embodiments comprises the plurality of holes 2120. The presence of the plurality of holes 2120 (or other light transmission structures) may affect the transmission of light through the non-transmissive portion 2132 by potentially allowing more light to pass through the mask 2100. In one embodiment, the non-transmissive portion 2132 is configured to absorb about 98 percent or more of the incident light from passing through the mask 2100 without holes 2120 being present. The presence of the plurality of holes 2120 allows more light to pass through the non-transmissive portion 2132 such that only about 95 percent of the light incident on the non-transmissive portion 2132 is prevented from passing through the non-transmissive portion 2132. The holes 2120 may reduce the benefit of the aperture 2128 on the depth of focus of the eye by allowing more light to pass through the non-transmissive portion to the retina.

As discussed above, the holes 2120 of the mask 2100 shown in FIG. 18A may be located anywhere on the mask 2100. Other mask embodiments described herein below locate substantially all of the light transmission holes are in one or more regions of a mask.

The holes 2120 of FIG. 18A extend at least partially between the anterior surface 2108 and the posterior surface 2112 of the mask 2100. In one embodiment, each of the holes 2120 includes a hole entrance 2160 and a hole exit 2164. The hole entrance 2160 is located adjacent to the anterior surface 2108 of the mask 2100. The hole exit 2164 is located adjacent to the posterior surface 2112 of the mask 2100. In one embodiment, each of the holes 2120 extends the entire distance between the anterior surface 2108 and the posterior surface 2112 of the mask 2100.

In one embodiment, the holes 2120 have a diameter in the range of about 0.002 mm to about 0.050 mm. In certain embodiments, the holes 2120 have a diameter of about 0.005 mm or more. In another embodiment, the holes have a diameter of about 0.020 mm. In another embodiment, the holes have a diameter of about 0.025 mm. In another embodiment, the holes have a diameter of about 0.027 mm. In another embodiment, the holes 2120 have a diameter in the range of about 0.020 mm to about 0.029 mm. In one embodiment, the number of holes in the plurality of holes 2120 is selected such that the sum of the surface areas of the hole entrances 2140 of all the holes 2100 comprises about 5 percent or more of surface area of the anterior surface 2108 of the mask 2100. In another embodiment, the number of holes 2120 is selected such that the sum of the surface areas of the hole exits 2164 of all the holes 2120 comprises about 5 percent or more of surface area of the posterior surface 2112 of the mask 2100. In another embodiment, the number of holes 2120 is selected such that the sum of the surface areas of the hole exits 2164 of all the holes 2120 comprises about 5 percent or more of surface area of the posterior surface 2112 of the mask 2112 and the sum of the surface areas of the hole entrances 2140 of all the holes 2120 comprises about 5 percent or more of surface area of the anterior surface 2108 of the mask 2100. In another embodiment, the plurality of holes 2120 may comprise about 1600 microperforations. In another embodiment, the plurality of holes 2120 comprises about 8400 microperforations.

Each of the holes 2120 may have a relatively constant cross-sectional area. In one embodiment, the cross-sectional shape of each of the holes 2120 is substantially circular. Each of the holes 2120 may comprise a cylinder extending between the anterior surface 2108 and the posterior surface 2112.

The relative position of the holes 2120 is of interest in some embodiments. As discussed above, the holes 2120 of the mask 2100 are hex-packed, e.g., arranged in a hex pattern. In particular, in this embodiment, each of the holes 2120 is separated from the adjacent holes 2120 by a substantially constant distance, sometimes referred to herein as a hole pitch. In one embodiment, the hole pitch is about 0.045 mm.

In a hex pattern, the angles between lines of symmetry are approximately 43 degrees. The spacing between any two neighboring holes is generally within the range of from about 30 microns to about 100 microns, and, in one embodiment, is approximately 43 microns. The hole diameter is generally within the range of from about 2 microns to about 100 microns, and in one embodiment, is approximately 20 microns. The light transmission is a function of the sum of hole areas as will be understood by those of skill in the art in view of the disclosure herein.

Negative visual effects may arise due to the presence of the light transmission hole arrangement 2116. For example, in some cases, a hex packed arrangement of the holes 2120 can generate diffraction patterns visible to the patient. For example, patients might observe a plurality of spots, e.g., six spots, surrounding a central light with holes 2120 having a hex patterned.

A variety of techniques are possible that produce advantageous arrangements of light transmission holes such that diffraction patterns and other deleterious visual effects do not substantially inhibit other visual benefits of a mask. In one embodiment, where diffraction effects would be observable, the light transmission holes are arranged to spread the diffracted light out uniformly across the image to eliminate observable spots. In another embodiment, the light transmission holes employ a pattern that substantially eliminates diffraction patterns or pushes the patterns to the periphery of the image.

Figure 20B:
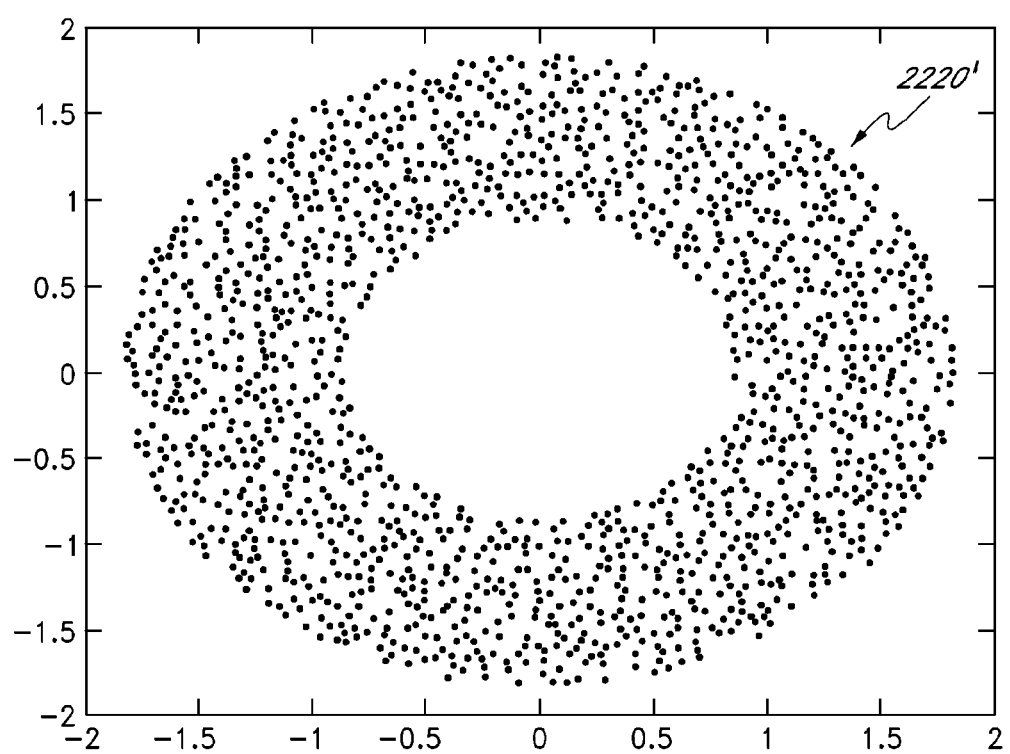
FIG. 20B is a graphical representation of another arrangement of holes of a plurality of holes that may be formed on the mask of FIG. 18A.
Figure 20C:
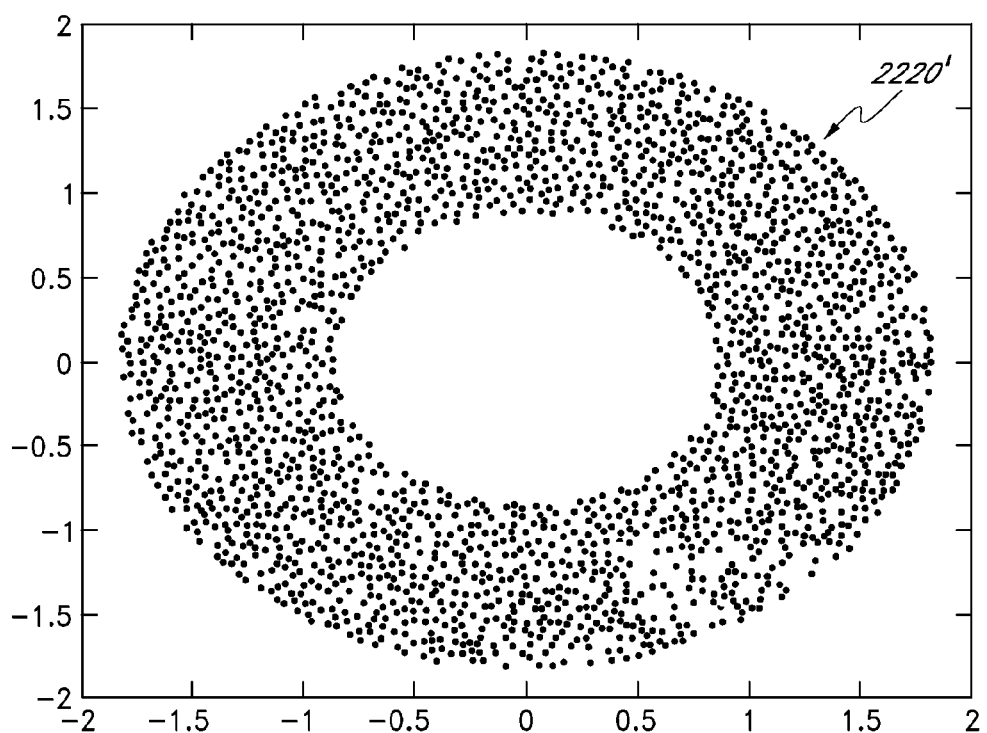
FIG. 20C is a graphical representation of another arrangement of holes of a plurality of holes that may be formed on the mask of FIG. 18A.

FIGS. 20B-20C show two embodiments of patterns of holes 2220' that may be applied to a mask that is otherwise substantially similar to the mask 2100. The holes 2220' of the hole patterns of FIGS. 20B-20C are spaced from each other by a random hole spacing or hole pitch. In other embodiments discussed below, holes are spaced from each other by a non-uniform amount, not a random amount. In one embodiment, the holes 2220' have a substantially uniform shape (cylindrical shafts having a substantially constant cross-sectional area). FIG. 20C illustrates a plurality of holes 2220' separated by a random spacing, wherein the density of the holes is greater than that of FIG. 20B. Generally, the higher the percentage of the mask body that has holes the more the mask will allow light to transmit through the mask. One way to provide a higher percentage of hole area is to increase the density of the holes. Increased hole density can also permit smaller holes to achieve the same light transmission as is achieved by less dense, larger holes.

Figure 21A:
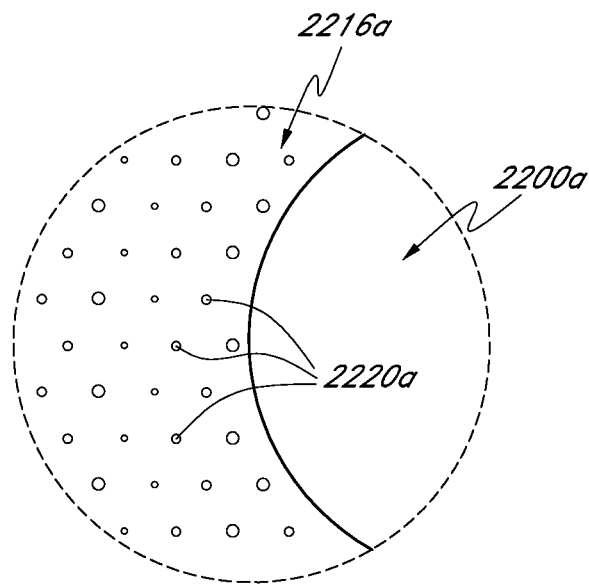
FIG. 21A is an enlarged view similar to that of FIG. 18A showing a variation of a mask having non-uniform size.

FIG. 21A shows a portion of another mask 2200a that is substantially similar to the mask 2100, except described differently below. The mask 2200a can be made of the materials discussed herein, including those discussed above. The mask 2200a can be formed by any suitable process, such as those discussed herein and with variations of such processes. The mask 2200a has a light transmission hole arrangement 2216a that includes a plurality of holes 2220a. A substantial number of the holes 2220a have a non-uniform size. The holes 2220a may be uniform in cross-sectional shape. The cross-sectional shape of the holes 2220a is substantially circular in one embodiment. The holes 2220a may be circular in shape and have the same diameter from a hole entrance to a hole exit, but are otherwise non-uniform in at least one aspect, e.g., in size. It may be preferable to vary the size of a substantial number of the holes by a random amount. In another embodiment, the holes 2220a are non-uniform (e.g., random) in size and are separated by a non-uniform (e.g., a random) spacing.

Figure 21B:
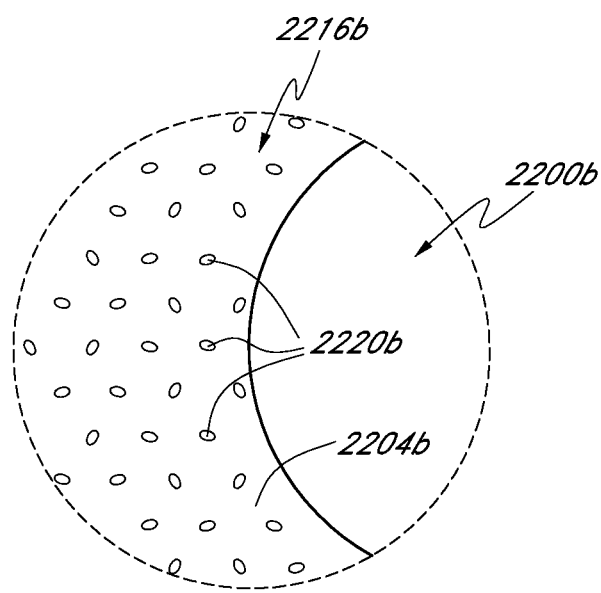
FIG. 21B is an enlarged view similar to that of FIG. 18A showing a variation of a mask having a non-uniform facet orientation.

FIG. 21B illustrates another embodiment of a mask 2200b that is substantially similar to the mask 2100, except as described differently below. The mask 2200b can be made of the materials discussed herein. Also, the mask 2200b can be formed by any suitable process, such as those discussed herein and with variations of such processes. The mask 2200b includes a body 2204b. The mask 2200b has a light transmission hole arrangement 2216b that includes a plurality of holes 2220b with a non-uniform facet orientation. In particular, each of the holes 2220b has a hole entrance that may be located at an anterior surface of the mask 2200b. A facet of the hole entrance is defined by a portion of the body 2204b of the mask 2200b surrounding the hole entrance. The facet is the shape of the hole entrance at the anterior surface. In one embodiment, most or all the facets have an elongate shape, e.g., an oblong shape, with a long axis and a short axis that is perpendicular to the long axis. The facets may be substantially uniform in shape. In one embodiment, the orientation of facets is not uniform. For example, a substantial number of the facets may have a non-uniform orientation. In one arrangement, a substantial number of the facets have a random orientation. In some embodiments, the facets are non-uniform (e.g., random) in shape and are non-uniform (e.g., random) in orientation.

Other embodiments may be provided that vary at least one aspect, including one or more of the foregoing aspects, of a plurality of holes to reduce the tendency of the holes to produce visible diffraction patterns or patterns that otherwise reduce the vision improvement that may be provided by a mask with an aperture, such as any of those described above.

For example, in one embodiment, the hole size, shape, and orientation of at least a substantial number of the holes may be varied randomly or may be otherwise non-uniform. The mask may also be characterized in that at least one of the hole size, shape, orientation, and spacing of a plurality of holes is varied to reduce the tendency of the holes to produce visible diffraction patterns. In certain embodiments, the tendency of the holes to produce visible diffraction patterns is reduced by having a plurality of the holes having a first hole size, shape, or spacing and at least another plurality of the holes with a second hole size, shape, or spacing different from the first hole size, shape, or spacing. In other embodiments, the mask is characterized in that at least one of the hole size, shape, orientation, and spacing of a substantial number of the plurality of holes is different than at least one of the hole size, shape, orientation, and spacing of at least another substantial number of the plurality of holes to reduce the tendency of the holes to produce visible diffraction patterns. In further embodiments, the holes are positioned at irregular locations. For example, the holes are positioned at irregular locations to minimize the generation of visible artifacts due to the transmission of light through the holes.

Figure 22:
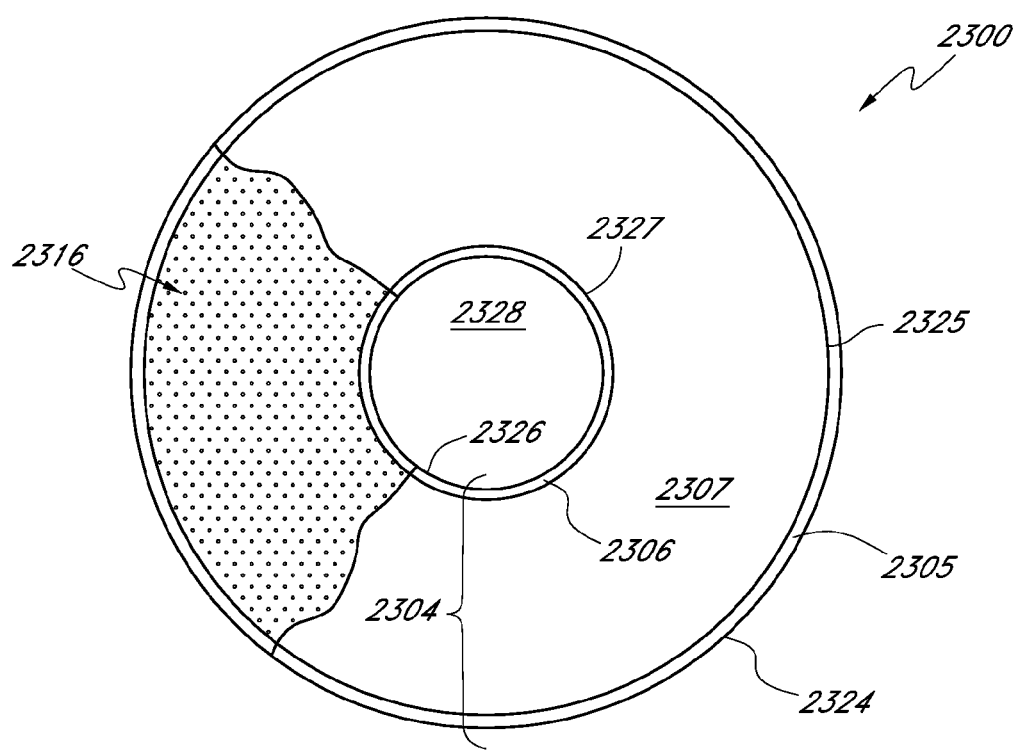
FIG. 22 is a top view of another embodiment of a mask having a hole region and a peripheral region.

FIG. 22 shows another embodiment of a mask 2300 that is substantially similar to any of the masks hereinbefore described, except as described differently below. The mask 2300 can be made of the materials discussed herein. Also, the mask 2300 can be formed by any suitable process, such as those discussed herein and with variations of such processes. The mask 2300 includes a body 2304. The body 2304 has an outer peripheral region 2305, an inner peripheral region 2306, and a hole region 2307. The hole region 2307 is located between the outer peripheral region 2305 and the inner peripheral region 2306. The body 2304 may also include an aperture region 2328, where the aperture (discussed below) is not a through hole. The mask 2300 also includes a light transmission hole arrangement 2316. In one embodiment, the light transmission hole arrangement includes a plurality of holes. At least a substantial portion of the holes (e.g., all of the holes) are located in the hole region 2307. As above, only a portion of the light transmission hole arrangement 2316 is shown for simplicity. But it should be understood that the hole arrangement may be located throughout the hole region 2307.

The outer peripheral region 2305 may extend from an outer periphery 2324 of the mask 2300 to a selected outer circumference 2325 of the mask 2300. The selected outer circumference 2325 of the mask 2300 is located a selected radial distance from the outer periphery 2324 of the mask 2300. In one embodiment, the selected outer circumference 2325 of the mask 2300 is located about 0.05 mm from the outer periphery 2324 of the mask 2300.

The inner peripheral region 2306 may extend from an inner location, e.g., an inner periphery 2326 adjacent an aperture 2328 of the mask 2300 to a selected inner circumference 2327 of the mask 2300. The selected inner circumference 2327 of the mask 2300 is located a selected radial distance from the inner periphery 2326 of the mask 2300. In one embodiment, the selected inner circumference 2327 of the mask 2300 is located about 0.05 mm from the inner periphery 2326.

The mask 2300 may be the product of a process that involves random selection of a plurality of locations and formation of holes on the mask 2300 corresponding to the locations. As discussed further below, the method can also involve determining whether the selected locations satisfy one or more criteria. For example, one criterion prohibits all, at least a majority, or at least a substantial portion of the holes from being formed at locations that correspond to the inner or outer peripheral regions 2305, 2306. Another criterion prohibits all, at least a majority, or at least a substantial portion of the holes from being formed too close to each other. For example, such a criterion could be used to assure that a wall thickness, e.g., the shortest distance between adjacent holes, is not less than a predetermined amount. In one embodiment, the wall thickness is prevented from being less than about 20 microns.

In a variation of the embodiment of FIG. 22, the outer peripheral region 2305 is eliminated and the hole region 2307 extends from the inner peripheral region 2306 to an outer periphery 2324. In another variation of the embodiment of FIG. 50, the inner peripheral region 2306 is eliminated and the hole region 2307 extends from the outer peripheral region 2305 to an inner periphery 2326.

In any of the foregoing mask embodiments, the body of the mask may be formed of a material selected to substantially prevent negative optic effects, such as diffraction, as discussed above. In various embodiments, the masks are formed of an open cell foam material, silicone, thermoset and thermoeleastic polymers such as PVDF, PMMA, metal, Teflon, or carbon. In another embodiment, the masks are formed of an expanded solid material.

As discussed above in connection with FIGS. 20B and 20C, various random patterns of holes may advantageously be provided. In some embodiments, it may be sufficient to provide regular patterns that are non-uniform in some aspect. Non-uniform aspects to the holes may be provided by any suitable technique.

In a first step of one technique, a plurality of locations 2220' is generated. The locations 2220' are a series of coordinates that may comprise a non-uniform pattern or a regular pattern. The locations 2220' may be randomly generated or may be related by a mathematical relationship (e.g., separated by a fixed spacing or by an amount that can be mathematically defined). In one embodiment, the locations are selected to be separated by a constant pitch or spacing and may be hex packed.

In a second step, a subset of the locations among the plurality of locations 2220' is modified to maintain a performance characteristic of the mask. The performance characteristic may be any performance characteristic of the mask. For example, the performance characteristic may relate to the structural integrity of the mask. Where the plurality of locations 2220' is selected at random, the process of modifying the subset of locations may make the resulting pattern of holes in the mask a "pseudo-random" pattern.

Where a hex packed pattern of locations (such as the locations 2120' of FIG. 20A) is selected in the first step, the subset of locations may be moved with respect to their initial positions as selected in the first step. In one embodiment, each of the locations in the subset of locations is moved by an amount equal to a fraction of the hole spacing. For example, each of the locations in the subset of locations may be moved by an amount equal to one-quarter of the hole spacing. Where the subset of locations is moved by a constant amount, the locations that are moved preferably are randomly or pseudo-randomly selected. In another embodiment, the subset of location is moved by a random or a pseudo-random amount.

In certain embodiments, an outer peripheral region is defined that extends between the outer periphery of the mask and a selected radial distance of about 0.05 mm from the outer periphery. In another embodiment, an inner peripheral region is defined that extends between an aperture of the mask and a selected radial distance of about 0.05 mm from the aperture. In another embodiment, an outer peripheral region is defined that extends between the outer periphery of the mask and a selected radial distance and an inner peripheral region is defined that extends between the aperture of the mask and a selected radial distance from the aperture. In one technique, the subset of location is modified by excluding those locations that would correspond to holes formed in the inner peripheral region or the outer peripheral region. By excluding locations in at least one of the outer peripheral region and the inner peripheral region, the strength of the mask in these regions is increased. Several benefits are provided by stronger inner and outer peripheral regions. For example, the mask may be easier to handle during manufacturing or when being rolled without causing damage to the mask. In other embodiments, the mask does not include an outer peripheral region and/or inner peripheral region that do not have holes (e.g., holes may extend to the inner periphery and/or the outer periphery).

In another embodiment, the subset of locations is modified by comparing the separation of the holes with minimum and or maximum limits. For example, it may be desirable to assure that no two locations are closer than a minimum value. In some embodiments this is important to assure that the wall thickness, which corresponds to the separation between adjacent holes, is no less than a minimum amount. As discussed above, the minimum value of separation is about 20 microns in one embodiment, thereby providing a wall thickness of no less than about 20 microns.

In another embodiment, the subset of locations is modified and/or the pattern of location is augmented to maintain an optical characteristic of the mask. For example, the optical characteristic may be opacity and the subset of locations may be modified to maintain the opacity of a non-transmissive portion of a mask. In another embodiment, the subset of locations may be modified by equalizing the density of holes in a first region of the body compared with the density of holes in a second region of the body. For example, the locations corresponding to the first and second regions of the non-transmissive portion of the mask may be identified. In one embodiment, the first region and the second region are arcuate regions (e.g., wedges) of substantially equal area. A first areal density of locations (e.g., locations per square inch) is calculated for the locations corresponding to the first region and a second areal density of locations is calculated for the locations corresponding to the second region. In one embodiment, at least one location is added to either the first or the second region based on the comparison of the first and second areal densities. In another embodiment, at least one location is removed based on the comparison of the first and second areal densities.

In a third step, a hole is formed in a body of a mask at locations corresponding to the pattern of locations as modified, augmented, or modified and augmented. The holes are configured to allow at least some light transmission through the mask without producing visible diffraction patterns.

V. Additional Mask Configurations

Figure 24A:
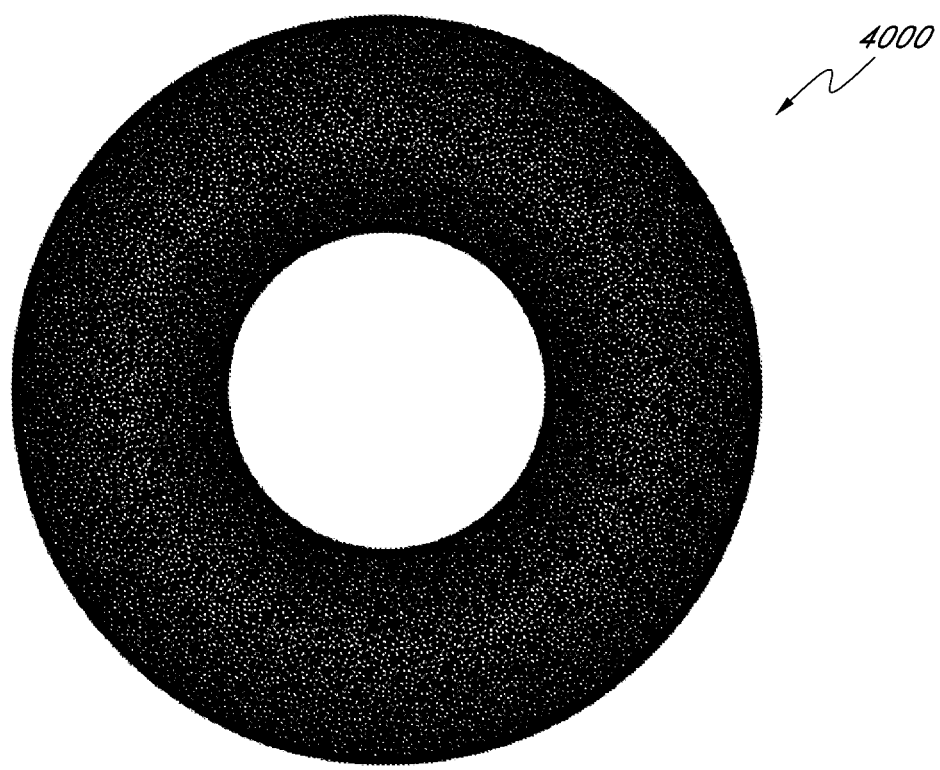
FIG. 24A is a top plan view of an embodiment of a mask configured to increase depth of focus as described herein.

A mask can have a variety of other configurations including configurations that include features described above. For example, the density of light transmission holes (e.g. area of holes per area of mask) can be different in different areas of the mask. In certain embodiments, the density of holes increases radially out from the inner periphery to the outer periphery of the mask. In certain other embodiments, the density of holes decreases radially out from the inner periphery to the outer periphery of the mask. Other variations are also possible. For example, a center annular region of the mask 4000 can have a higher density of holes than an inner annular region and an outer annular region, as illustrated in FIG. 24A. In another example, the center annular region of a mask has a lower density of holes than an inner annular region and an outer annular region. The density of holes is the percentage of surface area of the mask that has holes. A density of holes can be created by, for example, relatively few holes with relatively large area or relatively many holes with relatively small area. As described above, the holes can be arranged to reduce visible diffraction patterns.

The embodiment of the mask 4000 illustrated in FIG. 24A has an irregular hole pattern as described in Section IV. The mask 4000 includes an inner peripheral region neighboring the inner periphery of the mask 4000, an outer peripheral region neighboring the outer periphery of the mask 4000, and ten annular bands between the inner periphery region and the outer periphery region. The first band of the ten annular bands neighbors the inner periphery region, the second band neighbors the first band, and so forth. The tenth band neighbors the outer periphery region. Each band includes 840 holes, and the inner periphery region and outer periphery region includes no holes and are 50 microns wide. Each of the bands has a band width, a percentage of light transmission through the band, and a hole diameter for the holes in the band, as illustrated in Table III. The holes in the ten bands provide an average light transmission of 5%. The number and the properties of the bands and the number and properties of the holes in each band can be varied. For example, the bands can be configured to create a light transmission profile as described above. In certain embodiments, the mask 4000 has no inner periphery region and/or outer periphery region.

TABLE III

Properties of the example mask illustrated in FIG. 24A.

| Band No. | Hole Diameter (microns) | % Transmission | Band Width (microns) |
| --- | --- | --- | --- |
| 1 | 5.45 | 2.3 | 146 |
| 2 | 7.45 | 4.3 | 127 |
| 3 | 9.45 | 6.9 | 114 |
| 4 | 11.45 | 10.2 | 105 |
| 5 | 10.45 | 8.5 | 97 |
| 6 | 9.45 | 6.9 | 91 |
| 7 | 8.45 | 5.6 | 86 |
| 8 | 7.45 | 4.3 | 81 |
| 9 | 6.45 | 3.2 | 78 |
| 10 | 5.45 | 2.3 | 74 |

The transition of the density of holes between the center annular region to the inner and/or outer annular regions can be a gradual radial transition or can be a transition with one or more steps. The change in the density of holes from one region to another can be done by having the number of holes remain constant while the hole size is varied, by having the hole size remain constant while the number of holes is varied, or a combination of varying the number of holes and the hole size. Additional details regarding transition of the density of holes between the center annular region to the inner and/or outer annular regions are described in the concurrently filed international patent application, the entirety of which is hereby incorporated by reference, titled "CORNEAL INLAY WITH NUTRIENT TRANSPORT STRUCTURES," International Patent Application No. PCT/US2010/045541 filed the same day as the present application, which claims the benefit of U.S. Provisional Application No. 61/233,802, by Bruce Christie, Edward W. Peterson, and Corina van de Pol.

Advantageously, by having at least some light transmission through the mask, patient dim light vision can be improved over having substantially no light transmission through the mask. Embodiments include total area density of holes of the mask of greater than 1%, less than 10%, between 1% and 10%, between 2% and 5%. Embodiments include light transmittance through the mask of greater than 1%, less than 10%, between 1% and 10%, between 2% and 5%. In certain embodiments, the center annular region of the mask has an average light transmittance of between 2% and 5% and the inner annular region and the outer annular region have an average light transmittance of between 1 and 2%. In certain embodiments, the inner annular region is the annular region between the inner periphery of the mask to about one-third the radial distance from the inner periphery to the outer periphery of the mask. In certain embodiments, the outer annular region is the annular region between the outer periphery of the mask to about one-third the radial distance from the outer periphery to the inner periphery of the mask. In certain embodiments, the center annular region is the annular region between the inner annular region and the outer annular region.

Advantageously, if the mask is in a position between the posterior and anterior surfaces of a lens body, the holes through the mask can help to prevent delamination of the interface between the mask and the lens body. Delamination can occur during manipulation of the intraocular implant such as when the intraocular implant is folded or rolled and placed into a tube to be implanted into the patient. The lens body can extend through the holes, thereby creating a bond (e.g. material "bridge") between the lens body on either side of the mask. Delamination can also be reduced by matching mechanical properties (e.g. elastic modulus) of the mask to the lens body. Another method to reduce delamination is to create a bond between the lens body and the mask. For example, the lens body and the mask can have cross-linking bonds or van der Waals forces between them.

The holes in the mask serve at least two purposes: the holes provide some light transmission and the holes create areas where the material of the implant body can extend through to create a material "bridge" that holds the mask in place. In certain embodiments, the mask includes holes greater than about 7 microns in diameter (e.g., greater than a cross-sectional area of about 35 $\mu m^2$), and preferably greater than about 10 microns in diameter (e.g., greater than a cross-sectional area of about 75 $\mu m^2$). In certain embodiments, the mask includes holes greater than about 7 microns in diameter (e.g., greater than a cross-sectional area of about 35 $\mu m^2$) and less than about 20 microns in diameter (e.g., less than a cross-sectional area of about 320 $\mu m^2$). In further embodiments, the mask includes holes less than about 50 microns in diameter (e.g., less than a cross-sectional area of about 2000 $\mu m^2$·Holes with diameters less than 7 microns may not be large enough for lens material such as silicone or acrylic to enter and migrate to form a bridge. Although, the viscosity of the lens material will affect whether the material will be able to migrate into the hole to form the bridge and a minimum cross-sectional area of the hole may be dependent on the material of the implant body. If the material of the implant body does not migrate into a hole, that hole may create a bubble that could interfere with the visual performance of the implant.

The total amount of light that passes through the mask can be desirable to be minimized to maximize near image contrast. Delamination can be prevented with a relatively small total area of the mask having holes for "bridges". For example, an area of about 3% of the mask can include holes which can balance maximizing mechanical strength and minimizing optical effects of the holes. In certain embodiments, the anterior surface of the mask has a mask surface area, and the light transmission structures (e.g., holes) in the mask have a total area on the anterior surface of the mask of about 1% to about 5% of the mask surface area. To limit the impact of diffraction of light passing through the holes of the mask, the holes can be made as small as possible. The Airy disc from each hole is larger the smaller the hole size, so the composite diffraction pattern produced by the pattern of holes becomes larger as well. The composite diffraction pattern spreads light over a larger portion of the retina, decreasing the local brightness of diffracted light and making diffraction artifacts less visible. Diffraction patterns produced by a pattern of holes also tends to have a chromatic component such that the diffraction halo tends to graduate in color radially. Varying the size of the holes produces this effect in multiple scales, which scrambles the color of the halo. This reduces color contrast in the halo, making it less noticeable.

Figure 24B:
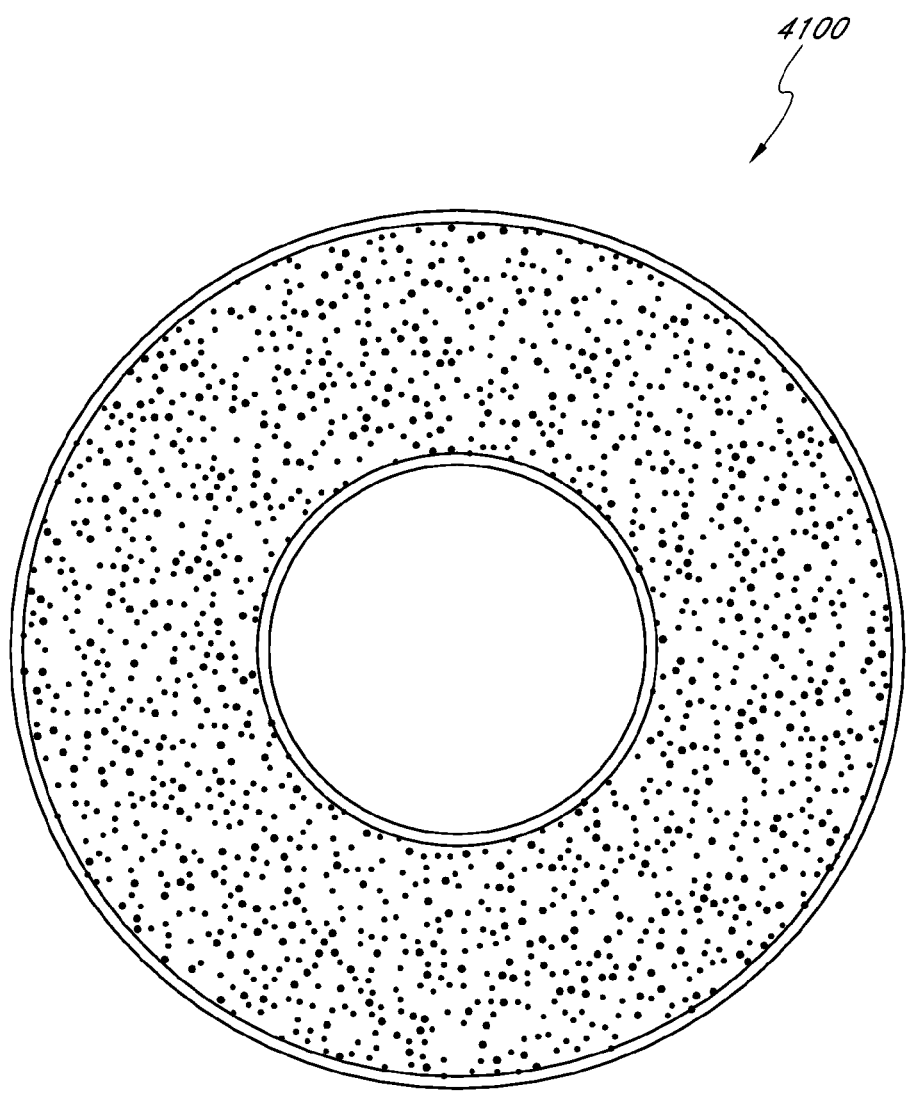
FIG. 24B is a front plan view of an embodiment of a mask configured to increase depth of focus as described herein.
Figure 24C:
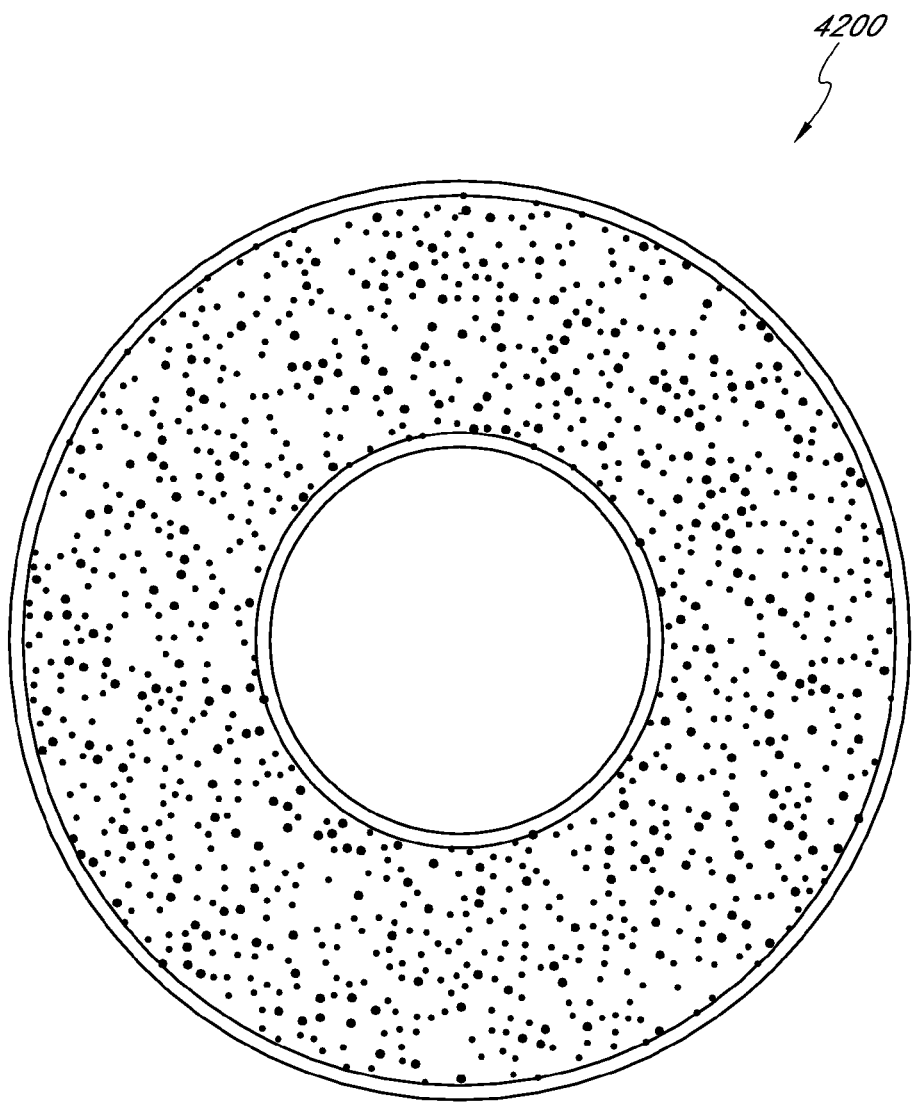
FIG. 24C is a front plan view of an embodiment of a mask configured to increase depth of focus as described herein.
Figure 24D:
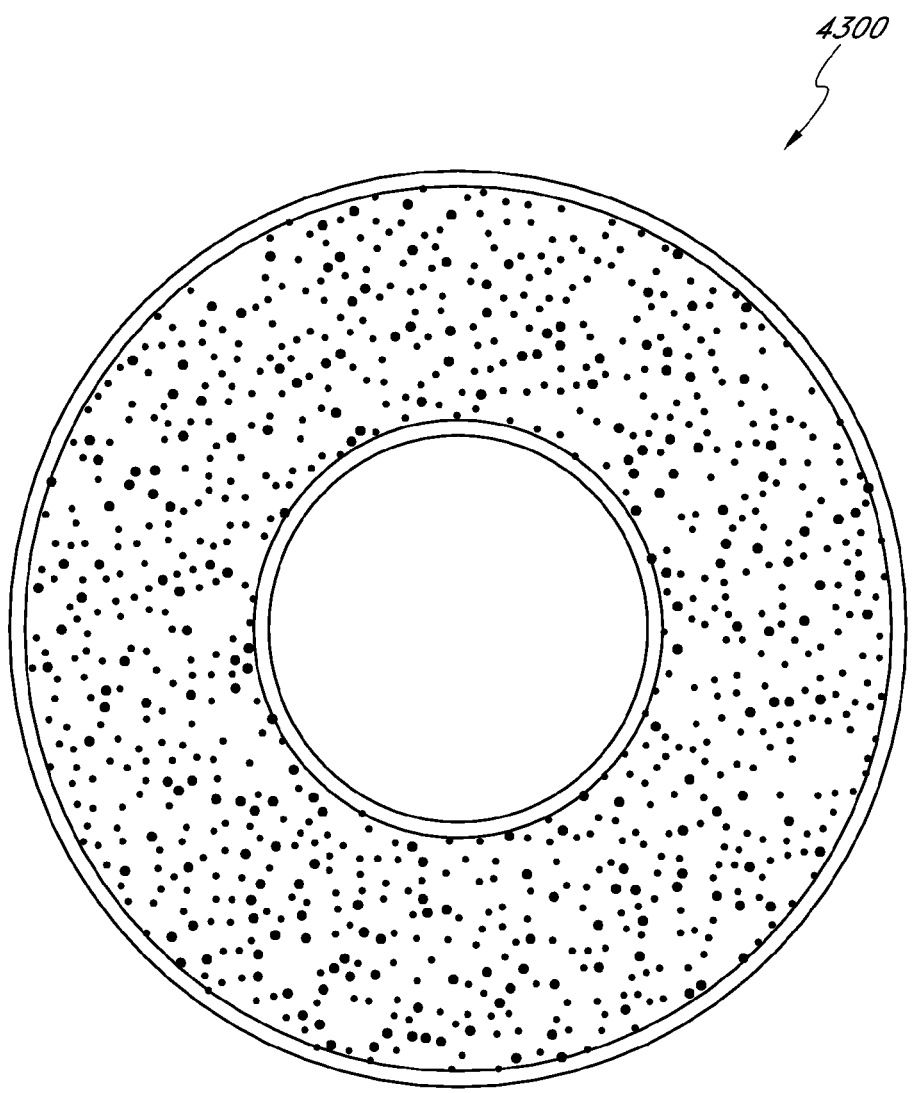
FIG. 24D is a front plan view of an embodiment of a mask configured to increase depth of focus as described herein.

In a certain embodiment, the mask includes randomly or pseudo-randomly placed holes across the mask. The mask 4100 illustrated in FIG. 24B has a light transmission of about 3.02%. The mask of FIG. 24B has holes with one of four hole diameters including 10 microns, 13 microns, 16 microns, and 19 microns. There is an equal number of holes with each hole diameter. An algorithm can be used to randomly or pseudo-randomly assign the variously sized holes to locations across the mask annulus. The rules for the randomization program can include (1) that there be no "collisions" of the holes (e.g., the holes have no contact with each other), (2) that no holes interfere with the inner and outer peripheral edges of the mask, and (3) that the holes are placed in such a way as to create substantial uniform density across the mask annulus. For example, the rules for the randomization program may include one or more of these rules. FIGS. 24C and 24D illustrate additional examples of hole positioning for masks 4200, 4300 using similar parameters as that were used for the mask of FIG. 24B.

The outer diameter of the outer periphery of the mask can be varied. In certain embodiments, the outer diameter is selected to selectively allow an amount of light to pass to the retina of the eye. The pupil of the eye changes size in different lighting condition. In low light situations, the pupil of the eye enlarges to let more light into the eye. The outer diameter can be selected so that light does not pass outside the outer periphery of the mask in relatively high light conditions, and so that at least some light can pass outside the outer periphery of the mask in relatively low light conditions. The pupil size of patients often can vary; therefore, the outer diameter of the mask can be selected for a specific patient pupil size. For example, for patients with relatively small pupils, dim light may present more of a vision issue than for patients with larger pupils. For smaller pupil patients, a mask with more light transmission and/or a smaller outer diameter will increase light reaching the retina and improve vision in dim light situations. Conversely, for larger pupil patients, less light transmission and/or a larger outer diameter mask may improve low-contrast near vision and block more unfocused light. The masked IOLs of the present application give the surgeon flexibility to prescribe the appropriate combination of masked IOL features for particular patients.

In certain embodiments, the center of the aperture of the mask is off-center to the center of the lens body. By having an aperture off-center to the optical center of the lens body, the intraocular lens can be rotated during the implantation procedure so that the optical center of the patient's eye can be aligned with the center of the aperture. The vision of the patient can be improved by aligning the optical center of the patient's eye with the aperture center.

VI. Methods of Making Ocular Implants

Intraocular implants (e.g., intraocular lenses) can be made or produced in a number of different ways. In certain embodiments, a rod can be formed with an optically transparent inner region along a length of the rod, an optically transparent outer region along the length of the rod and a substantially optically non-transparent middle region along the length of the rod between the inner region and the outer region. Cross-sectional sections along a plane substantially perpendicular to an axis parallel to the length of the rod can be sectioned out to form an implant body (e.g., lens body) with a mask through the implant body. In certain embodiments, a rod can be formed by forming an optically transparent rod. An opaque cylinder can be formed around the optically transparent rod. An optically transparent cylinder can then be formed around the opaque cylinder. In certain embodiments, the cylinders are formed by casting or molding.

In alternative embodiments, an implant body can be formed and then a mask can be attached to the posterior surface and/or anterior surface of the implant body. For example, the mask can be adhered with adhesive (e.g. glued), mechanically attached, snapped on, welded (e.g. tack welding, area welding), taped, press fit, thermal or hydration swell fit, held by surface tension, electric charge, magnetic attraction, polymerization, in-situ cross-linking (e.g. cross-linked by radiation), chemical means, etc. FIG. 25A illustrates an embodiment of an intraocular implant 8000 with a mask 8002 coupled to the anterior surface of the implant body 8004, and FIG. 25B illustrates another embodiment of an intraocular implant 8010 with a mask 8012 coupled to the posterior surface of the implant body 8014.

In certain embodiments, the implant body includes a structure to allow a mask to securely attach thereto. For example, the implant body can include clips or other structures to physically attach the mask. The implant body can include a recessed portion on the posterior or anterior surface. A mask that substantially fills the recessed portion can be placed in the recessed portion of the implant body. The inner periphery and/or the outer periphery of the recessed portion can include one or more protrusions. The inner periphery and/or the outer periphery can include one or more recesses. The mask can be attached to the implant body by inserting the mask into the recessed portion and the one or more protrusions can enter the one or more recesses to prevent the mask from separating from the implant body. In certain embodiments, the mask is attached to the implant body after the intraocular implant has been inserted into the patient. In other embodiments, the mask is attached to the implant body before the implant body has been inserted into the patient. For example, the mask can be attached to the implant body in a factory or in an operating room.

In further embodiments, an implant body can be formed around a mask. For example, an implant body can be injected molded around a mask. FIG. 25C illustrates one embodiment of an intraocular implant 8020 with a mask 8022 embedded within the implant body 8024. The mask 8032, 8042 can also be embedded near the anterior or posterior surface of the implant body 8034, 8044 of the intraocular implant 8030, 8040, as illustrated in FIGS. 25D and 25E, respectively. As illustrated in FIG. 25F, the mask 8052 can also be positioned near the transition zone 8056 of the implant body 8054. When the masked is positioned on the transition zone surface or within close proximity of the transition zone surface, the mask does not necessarily need to extend beyond the transition zone 8056 since light even at large angles that hits or passes through the transition zone surface would be blocked by the mask. The mask 8062 may also extend from the anterior surface to the posterior surface of the implant body 8064, as illustrated in FIG. 25G. Any of the locations or positions of the masks of FIGS. 25A-G can be applied to any of the implant bodies and intraocular implants described herein.

In certain embodiments, the intraocular implant includes one or more support members that extend from the mask to an outer surface of the implant body to aid in manufacturing intraocular implants with masks. The support members can suspend the mask in a mold cavity in desired alignment in relation to the mold cavity. A contact portion of the support member can physically contact a wall of the mold cavity to support the mask. For example, the support members can be removably coupled to mold to keep the mask stationary while the implant body is injected around the mask but can be removed after the implant body has been formed. The support member can be mechanically coupled to the mask, or the support member and mask can be a single piece (e.g., monolithic structure).

Figure 26A:
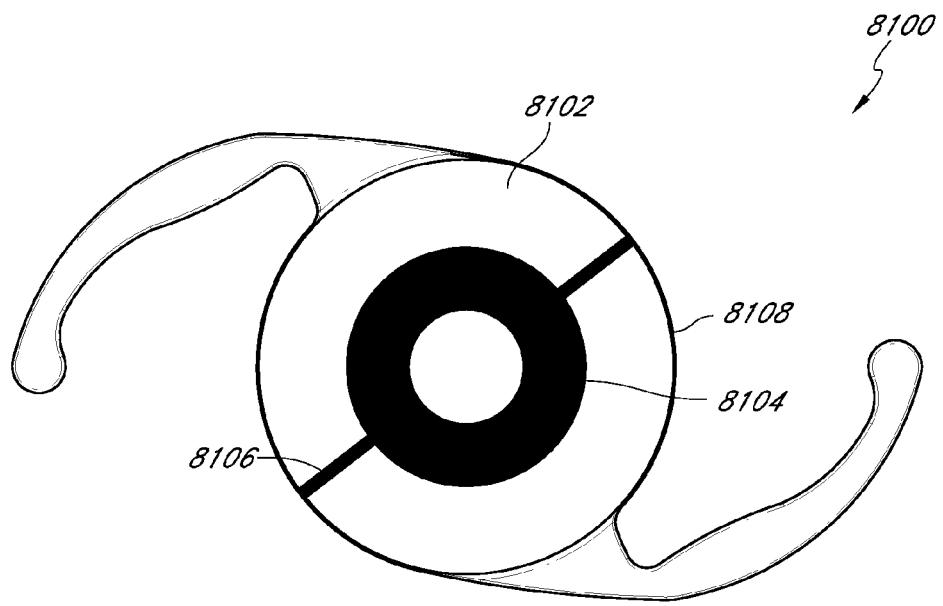
FIG. 26A is a front plan view of an embodiment of an intraocular implant with support members extending from the mask to a peripheral surface of the implant body as described herein.

FIG. 26A illustrates one embodiment of an intraocular implant 8100 with a mask 8104 that is within an implant body 8102. The intraocular implant 8100 includes one or more support members 8106 that are coupled to the mask 8104 and extend to at least the outer periphery 8106 of the implant body 8102. The support members 8106 may extend to the surface of the outer periphery 8106 or may extend beyond the surface of the outer periphery 8106.

Figure 26B:
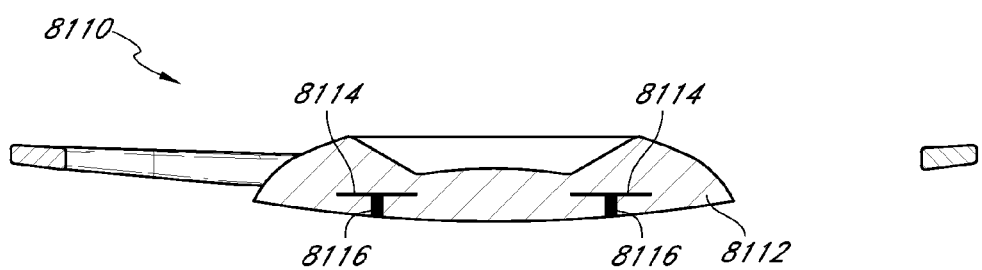
FIG. 26B is a cross-sectional view of an embodiment of an intraocular implant with support members extending from the mask to the posterior surface of the implant body as described herein.

FIG. 26B illustrates a second example of an intraocular implant 8110 that includes support members 8116. The support members 8116 are coupled to the mask 8114 and extend from the mask 8814 to at least the posterior surface 8113 of the implant body 8112. By positioning the support members 8116 between the mask 8114 and the posterior surface 8113, the support members 8816 can be hidden from line of sight of a patient.

Figure 26C:
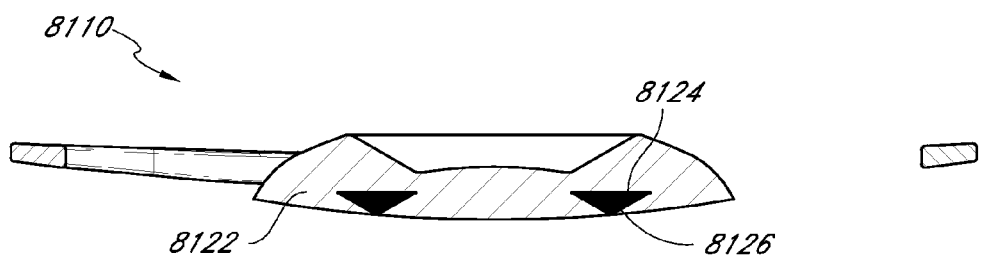
FIG. 26C is a cross-sectional view of an embodiment of an intraocular implant with a mask integrated with the support members as described herein.

FIG. 26C illustrates another example of support members 8126 that are hidden from a patient's line of sight. The mask 8124 and the support members 8126 are integrated into a toroid with a triangular or trapezoid cross-sectional shape. The portion of the toroid closer to the anterior surface of the implant body 8122 extends radially inwardly and outwardly further than the portion of the toroid closer to the posterior surface of the implant body 8122. A cross-section of the mask 8124 and support members 8126 appear as a posteriorly-pointing triangle or as an inverted pyramid. Advantageously, this embodiment minimizes unintended light blockage.

Figure 27A:
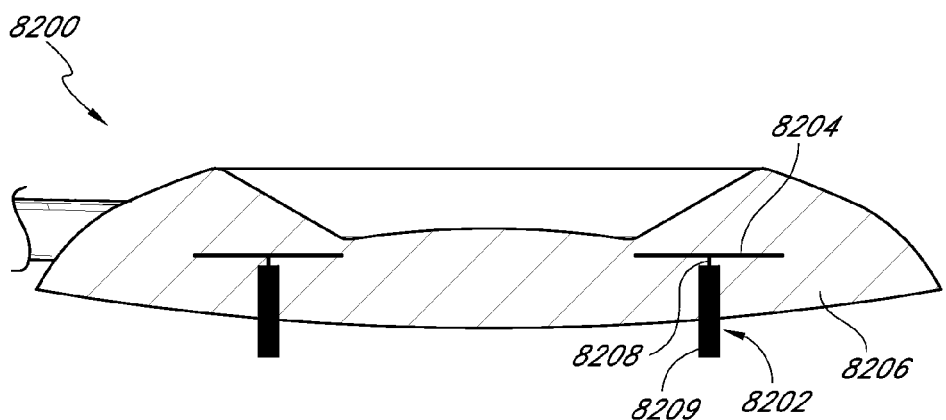
FIG. 27A is a cross-sectional view of an embodiment of an intraocular implant with tabs extending from the mask to the posterior surface of the implant body as described herein.
Figure 27B:
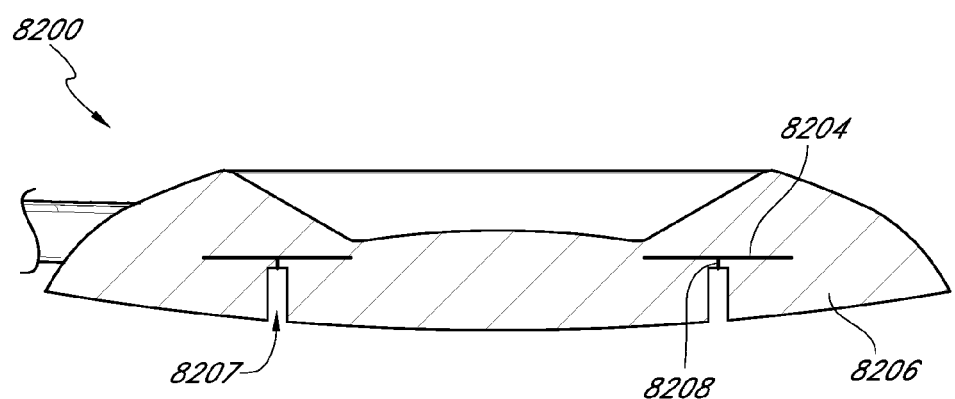
FIG. 27B is a cross-sectional view of the intraocular implant of FIG. 27A wherein a portion of the tabs have been removed.

The support structures may also include tabs that can be removed after the implant body has been formed around the mask. FIG. 27A illustrates an embodiment of an intraocular implant 8200 with support structures 8202 that include tabs. The support structures 8202 have a first portion 8208 that extends from the mask 8204 to a position within the implant body 8206 with a first cross-sectional area. The support structures 8202 also have a second portion 8209 that extends from the first portion to the surface of the implant body 8206 with a second cross-sectional area that is greater than the first cross-sectional area. After the implant body 8206 is formed around the mask 8204, the support structures 8202 can be broken off at or near the first portion 8208, as illustrated in FIG. 27B. Removal of the second portion 8209 can leave behind a cavity 8207 in the implant body 8206. The cavity 8207 can be left open or can be filled. For example, if increasing the biocompatibility of the implant 8200 is desired, the cavities 8207 can be filled so that the mask 8204 is physically or biologically isolated from the eye within or by the implant body 8206.

Figure 28B:
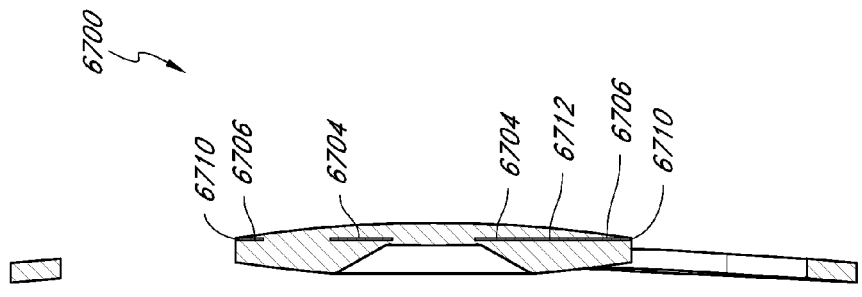
FIG. 28B is a cross-sectional view of the intraocular implant of FIG. 28A.
Figure 28A:
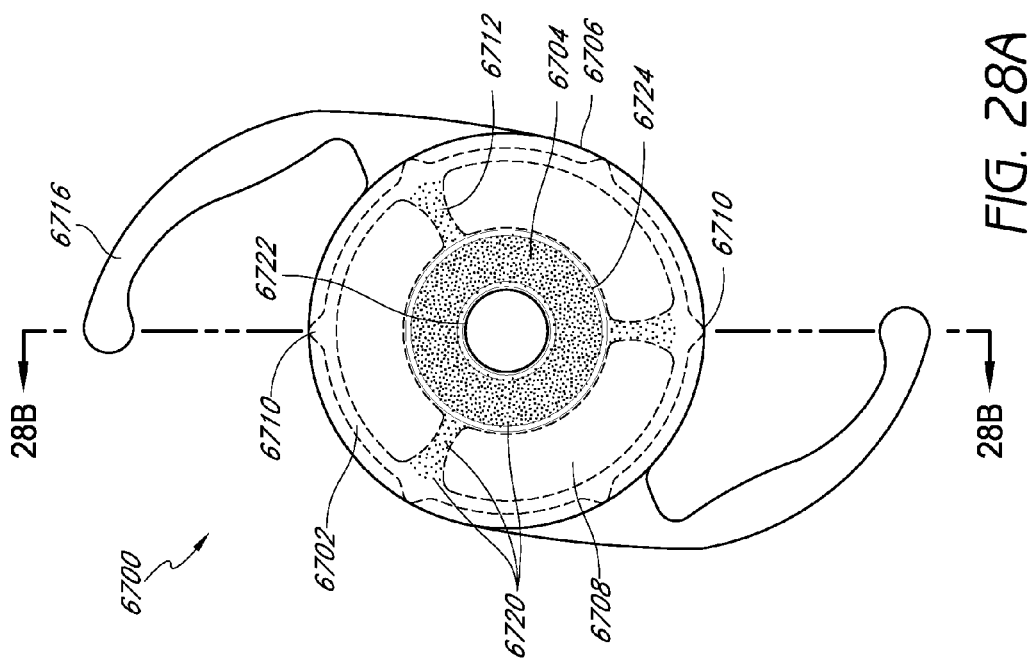
FIG. 28A is a front plan view of an embodiment of an intraocular implant with a support member as described herein.

FIG. 28A is a top view and FIG. 28B is a cross-sectional view of an embodiment of an intraocular implant 6700 with a support member 6702. The support member 6702 extends from the mask 6704 to the outer periphery 6706 of the implant body 6708. The support member 6702 can include one or more contact portions 6710 that can removably couple to the mold during injection of the implant body 6708 around the mask 6704. In certain embodiments, the implant body 6708 is injected around both the mask 6704 and the support member 6702. The support member 6702 can also include linking members 6712 that couple the contact portions 6710 and the mask 6704. The linking members 6712 have an anterior and/or posterior surface area that is minimized so that the linking member 6712 substantially does not block light that passes through the implant body 6708 outside the outer periphery of the mask 6704.

The support structure 6702 can include more mass near the outer periphery of the implant body 6708 where the support structure 6702 would less likely interfere with the patient's vision. For example, the support structure 6702 can have an annulus or ring near the outer periphery of the implant body 6708 that provides additional support and further restricts movement of the mask 6704 and portions of the support structure 6702 during molding process when material flows around the mask. The flow of material can produce forces on the mask 6704 and support structure 6702. In certain embodiments, the implant body 6708 and the haptics 6716 are a single piece (e.g., monolithic structure).

As illustrated in FIG. 28A, the mask 6704, linking members 6712, and/or support structure 6702 may include light transmission structures 6720 such as holes, as described herein. The mask 6704 may also include an inner peripheral region 6722 neighboring the inner diameter and an outer peripheral region 6724 neighboring the outer diameter that substantially does not have light transmission structures 6720, as described above. The light transmission structures 6720 can be applied to any of the embodiments of described herein and the different configurations of light transmission structures described herein such as varying hole spacing, size, shape and/or orientation can be applied to this embodiment or any embodiment that includes a mask.

FIG. 29A is a top view and FIG. 29B is a cross-sectional view of an embodiment of an intraocular implant 6800 similar to the intraocular implant 6700 of FIGS. 28A and 28B with a different optical power. The intraocular implants features described herein can be combined with a variety of optical power implant bodies.

Figure 30B:
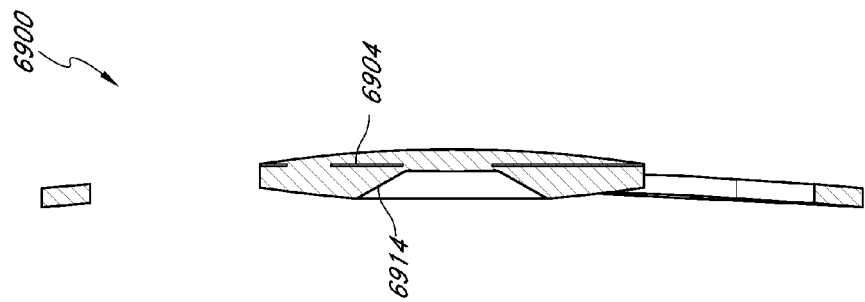
FIG. 30B is a cross-sectional view of the intraocular implant of FIG. 30A.
Figure 30A:
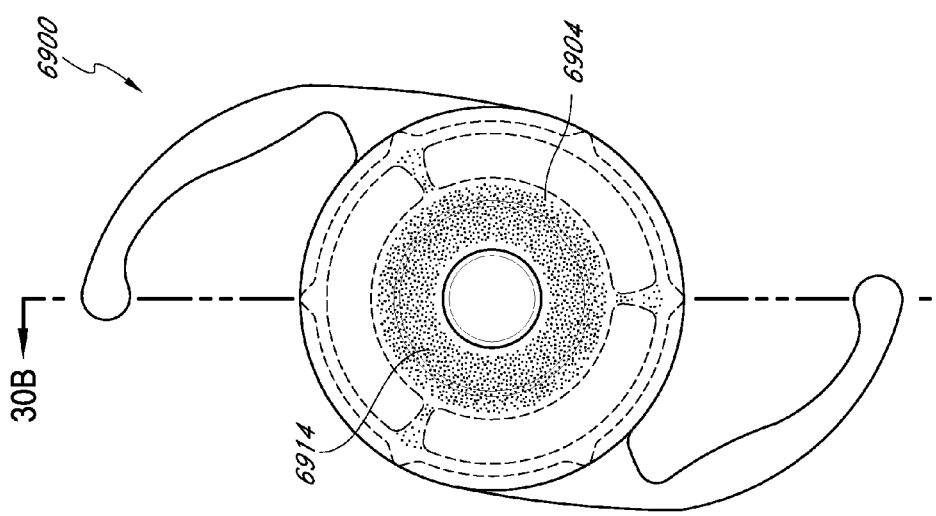
FIG. 30A is a front plan view of an embodiment of an intraocular lens with a mask that extends radially beyond the outer periphery of the transition zone as described herein.
Figure 31B:
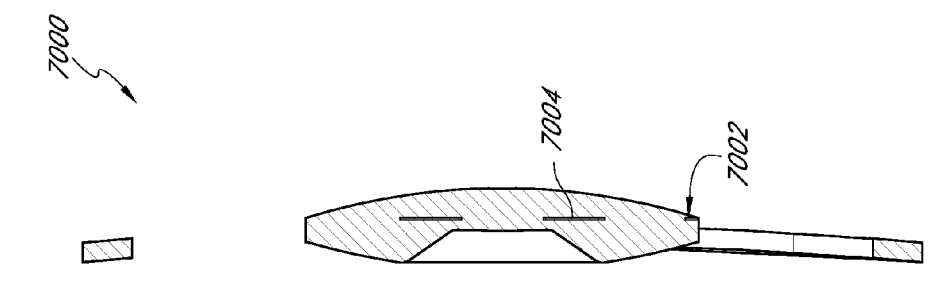
FIG. 31B is a cross-sectional view of the intraocular implant of FIG. 31 A.
Figure 31A:
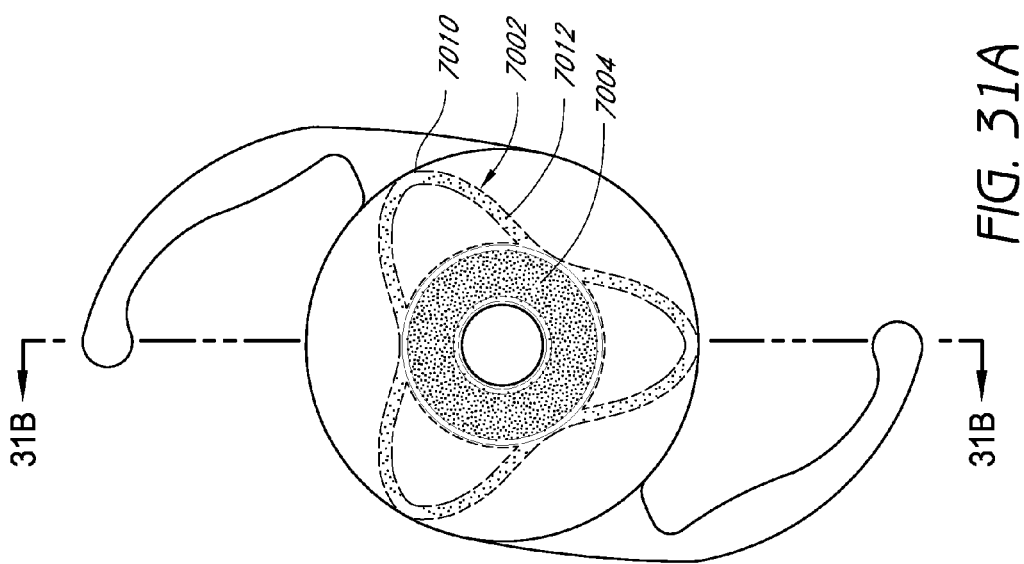
FIG. 31A is a front plan view of another embodiment of an intraocular implant with a support member as described herein.
Figure 33B:
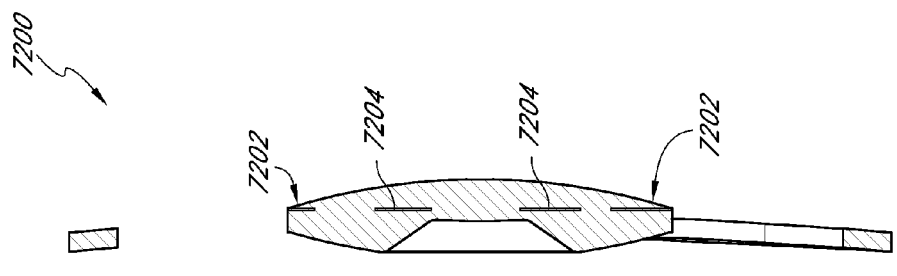
FIG. 33B is a cross-sectional view of the intraocular implant of FIG. 33A.
Figure 33A:
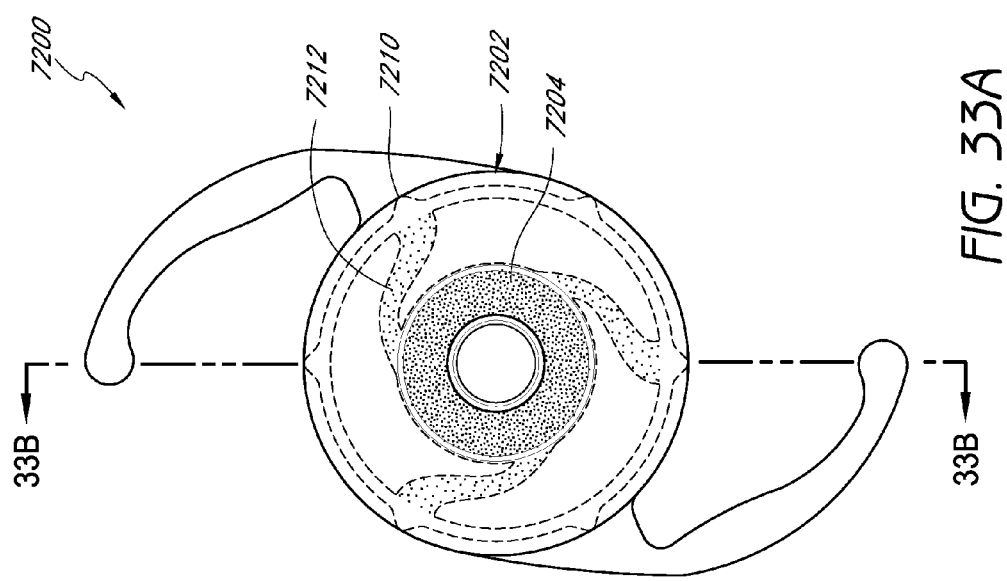
FIG. 33A is a front plan view of a further embodiment of an intraocular implant with a support member as described herein.
Figure 34B:
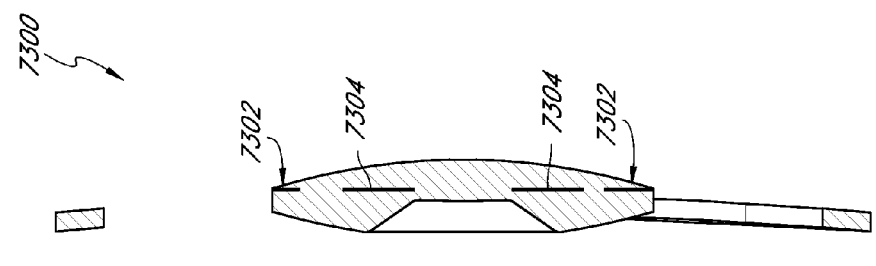
FIG. 34B is a cross-sectional view of the intraocular implant of FIG. 34A.
Figure 34A:
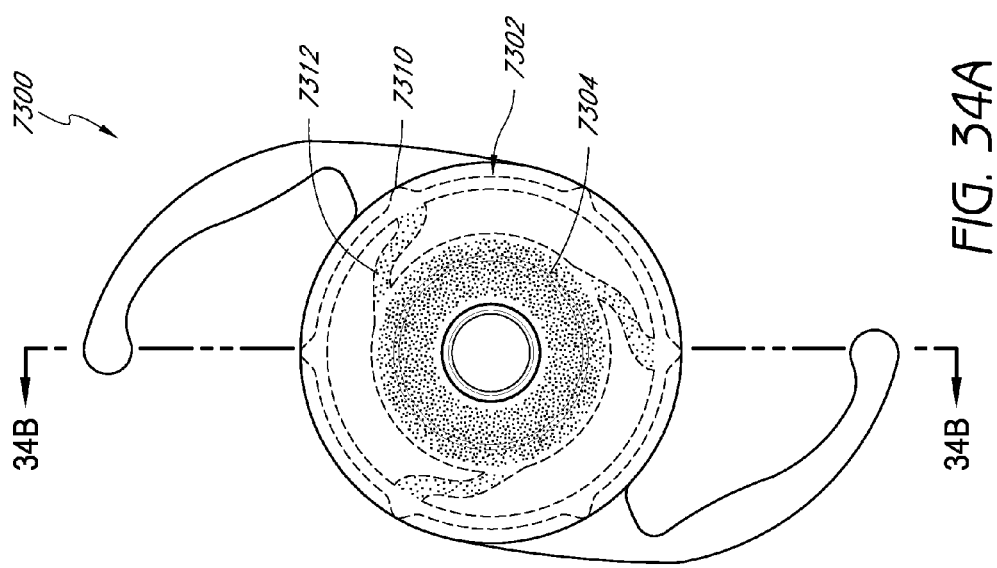
FIG. 34A is a front plan view of a further embodiment of an intraocular implant with a mask that extends radially beyond the outer periphery of the transition zone as described herein.

FIG. 30A is a top view and FIG. 30B is a cross-sectional view of another embodiment of an intraocular implant 6900 similar to the intraocular implant 6700 of FIGS. 28A and 28B. The outer periphery of the mask 6904 extends beyond the outer periphery of the transition zone (e.g., second portion) 6914 which can block light that pass through the transition zone 6914 at large incident angles (e.g., angle between the normal to the surface and the incident light) to the anterior surface of the implant body 6908.

FIGS. 31A-34B are additional embodiments of intraocular implants 7000, 7100, 7200, 7300 with various configurations of support members 7002, 7102, 7202, 7302. For example, the intraocular implants 7000, 7100 of FIGS.

31A-32B have support members 7002, 7102 that have linking members 7012, 7112 that loop from a first portion of the mask 7004, 7104 to a contact portion 7010, 7110 and back to a second portion of the mask 7004, 7104. The intraocular implants 7200, 7300 of FIGS. 33A-34B are similar to the intraocular implant 6700 of FIGS. 28A-B; however, the linking members 7212, 7312 do not connect the mask 7204, 7304 and the contact portions 7210, 7310 through a straight path. The linking members 7212, 7312 connect the mask 7204, 7304 and the contact portions 7210, 7310 through a curved or wavy path. The curved or wavy path can reduce visible effects of the linking members 7212, 7312 that a patient may observe.

The support members may be integrated with the haptic of intraocular implant. The haptic and support member may be coupled together or can be a single piece (e.g., monolithic structure). In certain embodiments, the mask, support member, and haptic are all coupled together. For example, the mask, support member, and haptic can be a single piece (e.g., monolithic structure). The mask, support member, and/or haptic may comprise the same material. Furthermore, the mask, support member, and/or haptic may comprise the same material of the implant body; however, the mask, support member, and/or haptic may include or incorporate a dye or other pigment to create opacity. Alternatively, the mask, support member, and/or haptic may comprise different materials than the implant body, but be materials that are compatible with the material of the implant body. FIG. 35A is a top view and FIG. 35B is a cross-sectional view of an embodiment of an intraocular implant 7400 with a support structure 7402 coupled to a mask 7404 and haptics 7416. The support structure 7402 extends away from the mask 7404 to an outer surface of the implant body 7408. The haptics 7416 extend away from the support structure 7402 and implant body 7408. The haptics 7416 can provide contact portions with the mold to retain the mask 7404 while the implant body 7408 is injected around the mask 7404. The mask 7404, support structure 7402, and haptics 7416 can be a single piece or coupled together such that they are configured to resist forces applied to the mask during formation of the implant body 7408. In certain embodiments, the haptic, support members, and mask may be substantially planar.

FIG. 36A is a top view and FIG. 36B is a cross-sectional view of an embodiment of an intraocular implant 7500 similar to the intraocular implant 7400 of FIGS. 35A-B. However, the mask 7504 is configured to be near the anterior surface 7518 of the implant body 7508 and follows the contours of the anterior surface 7518 of the implant body 7508. The closer the mask 7504 is to the anterior surface 7518 less light that pass through the transition zone 7914 on the anterior surface at large incident angles can pass through the posterior surface 7520 which can be observed as visible artifacts to a patient. For embodiments where the transition zone is on the posterior surface, the mask can be positioned to be near the posterior surface. The support member 7502 can also configured to be near the anterior surface 7518 of the implant body 7508.

In certain embodiments, the mask is printed onto an implant body. The mask can be printed on the posterior and/or the anterior surface of the implant body. The printed mask can either be adjacent the surface of the implant body or can penetrate into the implant body (stain, tattoo, etc.). Printing options can include offset printing, block printing, jet printing, etc. The mask can also be applied to the implant body by thermal transfer or hot stamping. The mask may also be laser etched onto the surface or within the implant body such as with a sub-surface laser engraving. The printed mask can be bonded or adhered to the implant body. In certain embodiments, the mask is printed onto the implant body after the implant body has been inserted into the patient. In other embodiments, the mask is printed onto the implant body before the implant body has been inserted into the patient. For example, the mask can be printed onto the implant body in a factory or in an operating room.

Figure 37A:
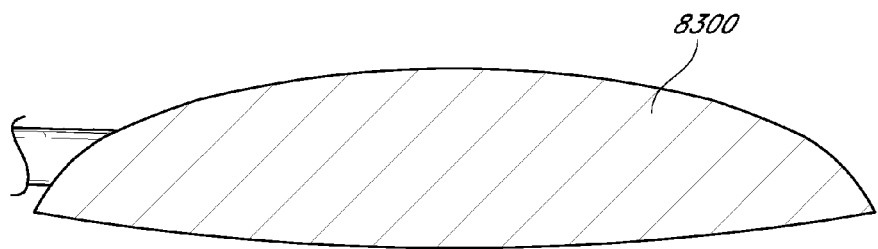
FIG. 37A is a cross-section view of an intraocular implant.
Figure 37B:
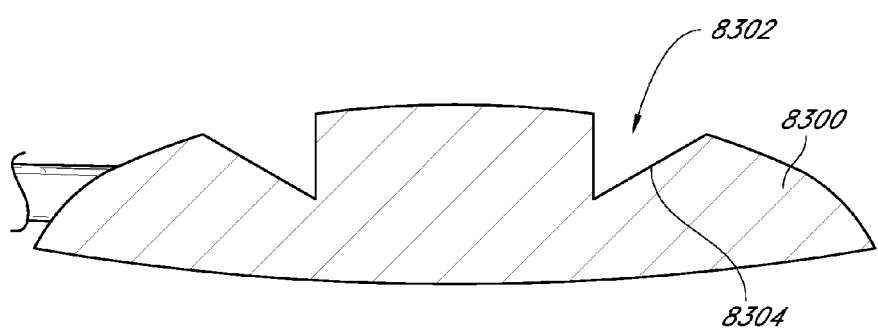
FIG. 37B is a cross-section view of the intraocular implant of FIG. 37A with a cavity formed into the implant body.
Figure 37C:
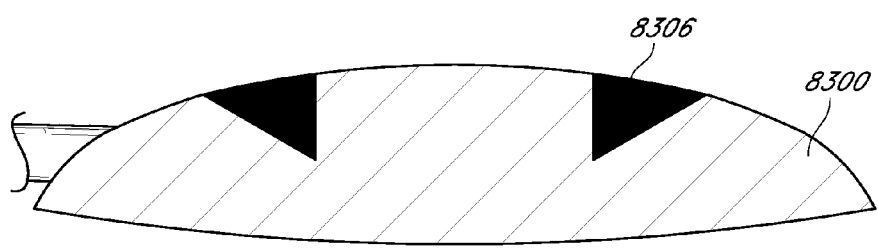
FIG. 37C is a cross-section view of the intraocular implant of FIG. 37B with the cavity at least partially filled with an opaque material.
Figure 37D:
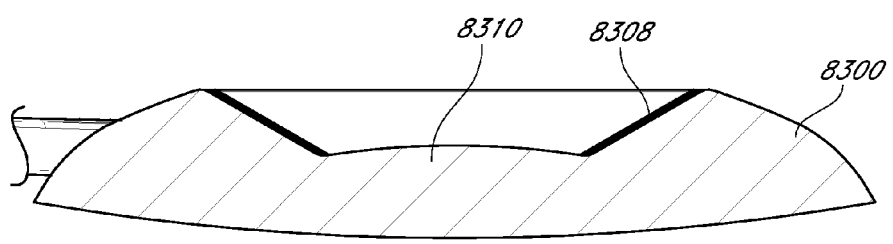
FIG. 37D is a cross-sectional view of the intraocular implant of FIG. 37C with a portion of the opaque material and central region removed.

FIGS. 37A-D illustrate another method of forming a mask 8308 on the anterior (or posterior) surface of an implant body 8300 with a transition zone 8304. FIG. 37A illustrates an implant body 8300 without a transition zone 8304 or mask 8308. A cavity 8302 such as an annulus can be formed (mechanically, chemically, etc.) into the anterior surface of the implant body 8300, as illustrated in FIG. 37B. The cavity 8302 can form the transition zone 8304. As illustrated in FIG. 37C, the cavity 8302 can be at least partially filled with an opaque material 8306 so that the transition zone 8304 is substantially covered. The central region 8310 can be formed (mechanically, chemically, etc.), as illustrated in FIG. 37D. Some of the opaque material 8306 can also be removed when the central region 8310 is formed while leaving a layer of opaque material 8306 substantially covering the transition zone 8304 to form a mask 8308.

Figure 38A:
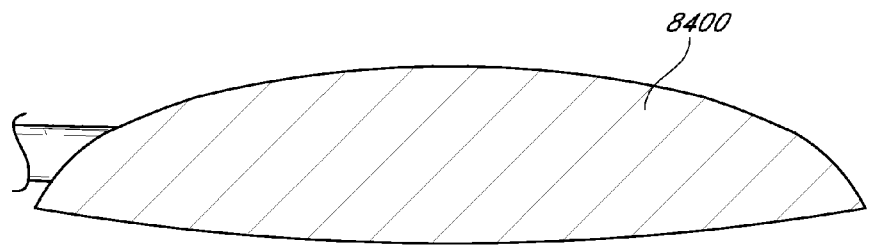
FIG. 38A is a cross-section view of an intraocular implant.
Figure 38B:
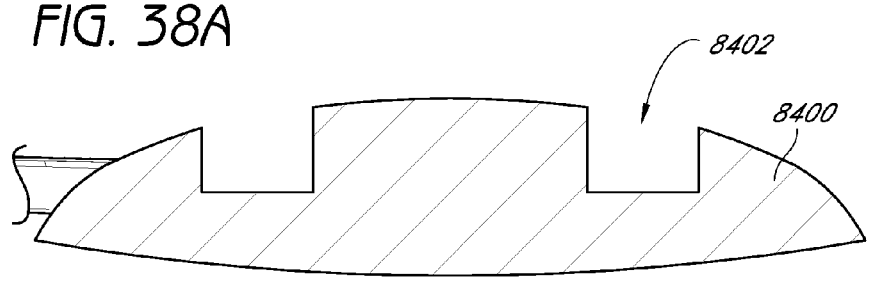
FIG. 38B is a cross-section view of the intraocular implant of FIG. 38A with a cavity formed into the implant body.
Figure 38C:
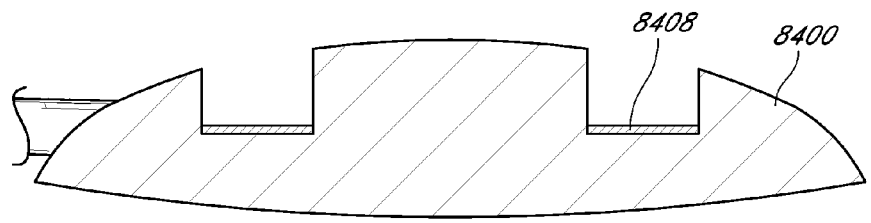
FIG. 38C is a cross-section view of the intraocular implant of FIG. 38B with mask positioned within the cavity.
Figure 38D:
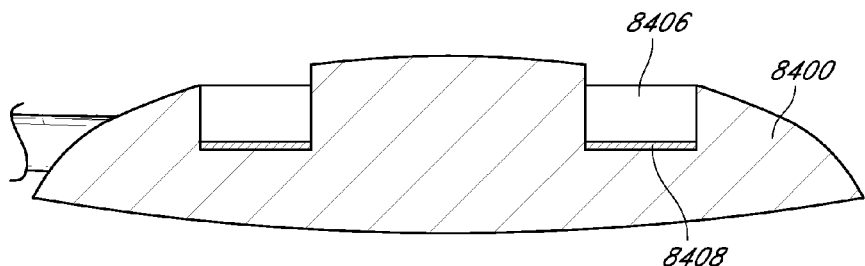
FIG. 38D is a cross-section view of the intraocular implant of FIG. 38C with the cavity at least partially filled with an implant body material.
Figure 38E:
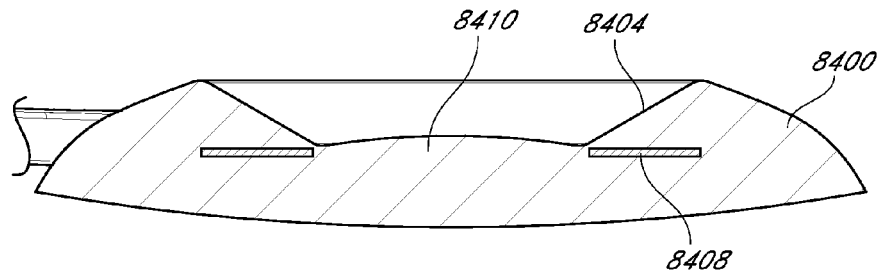
FIG. 38E is a cross-section view of the intraocular implant of FIG. 38D with a portion of the implant body removed.

FIGS. 38A-E illustrate method of forming a mask 8408 within the implant body 8400. FIG. 38A illustrates an implant body 8400, and FIG. 38B illustrates the implant body 8400 with a cavity 8402 formed into the anterior surface. A mask 8408 can be positioned within the cavity 8402, as illustrated in FIG. 38C, and the cavity 8402 can be at least partially filled with an implant body material 8406 to embed the mask 8408 into the implant body 8400, as illustrated in FIG. 38D. FIG. 38E illustrates the implant body 8400 with a portion the implant body material removed to form the central region 8410 and the transition zone 8404.

Figure 39A:
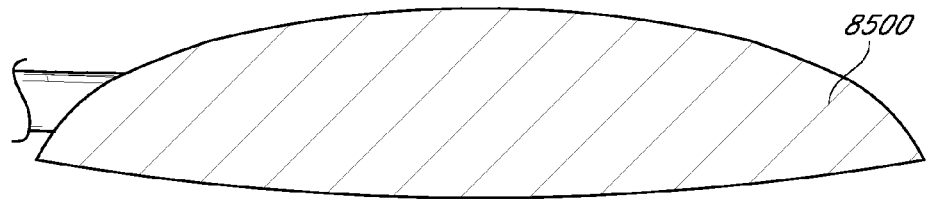
FIG. 39A is a cross-section view of an intraocular implant.
Figure 39B:
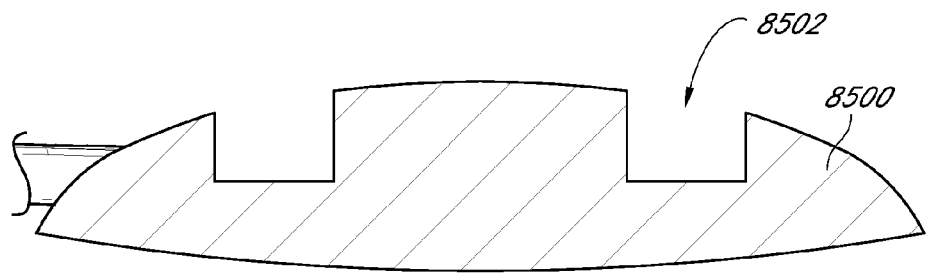
FIG. 39B is a cross-section view of the intraocular implant of FIG. 38A with a cavity formed into the implant body.
Figure 39C:
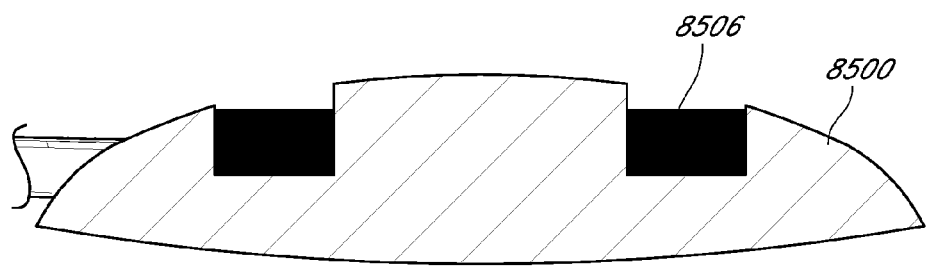
FIG. 39C is a cross-section view of the intraocular implant of FIG. 39B with the cavity at least partially filled with an opaque material.
Figure 39D:
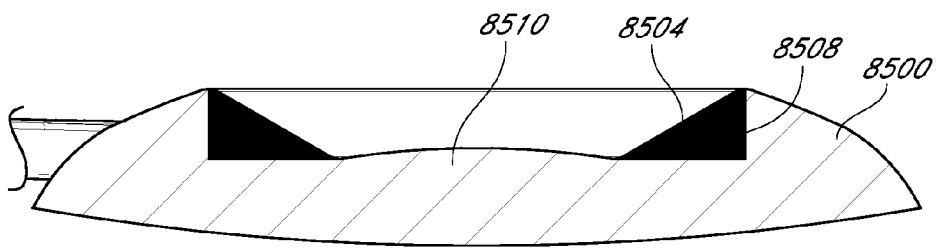
FIG. 39D is a cross-sectional view of the intraocular implant of FIG. 39C with a portion of the opaque material and central region removed.

FIGS. 39A-D illustrate another method of forming a mask 8508 on the anterior surface of an implant body 8500 with a transition zone 8504. FIG. 39A illustrates an implant body 8500 without a transition zone 8504 or mask 8508. A cavity 8502 such as an annulus can be formed into the anterior surface of the implant body 8500, as illustrated in FIG. 39B. As illustrated in FIG. 39C, the cavity 8502 can be at least partially filled with an opaque material 8506. The central region 8510 can be formed, as illustrated in FIG. 39D. Some of the opaque material 8506 can also be removed when the central region 8510 is formed, and the opaque material 8506 can form a transition zone 8504 and a mask 8508.

In certain embodiments, a mask is formed in or on the implant body by selectively making the material of the implant body opaque or reflective. For example, materials such as black silicone, carbon-powdered Teflon, PVDF with carbon, etc. can be used. Additional examples of materials that the mask can include are described in U.S. Patent Publication No. 2006/0265058. The implant body can be a material that changes from transparent to opaque (e.g., a photochromic material) or reflective upon being exposed to certain conditions. The molecular structure of the implant body material can be changed optically, chemically, electrically, etc. For example, structure of the implant body can be changed to create voids, regions of altered index, surface facets, etc. In certain embodiments, a dye in or on the implant body can be activated with light or electricity to change from being transparent to opaque or reflective. In certain embodiments, the mask is formed after the implant body has been inserted into the patient. In other embodiments, the mask is formed before the implant body has been inserted into the patient. For example, the mask can be formed in a factory or in an operating room.

In certain embodiments, the implant body has posterior and/or anterior surfaces with contours to create an optical power. The contours of the surfaces of the implant body can also be formed by a number of methods. For example, the implant body can be molded into a shape. In another example, the surfaces of the implant body can be milled to form the contours.

Haptics can be formed with the implant body or can be subsequently attached to the implant body. For example, haptics can be cast or molded onto the implant body in a single-piece configuration. In addition, haptics can be mechanically attached to the implant body. For example, holes can be drilled into the implant body and haptics can be inserted. Haptics can also be attached by using an adhesive or glue. In certain embodiments, the intraocular implant does not have an implant body. If the intraocular implant does not have an implant body, the haptics can be attached to the mask.

Figure 40:
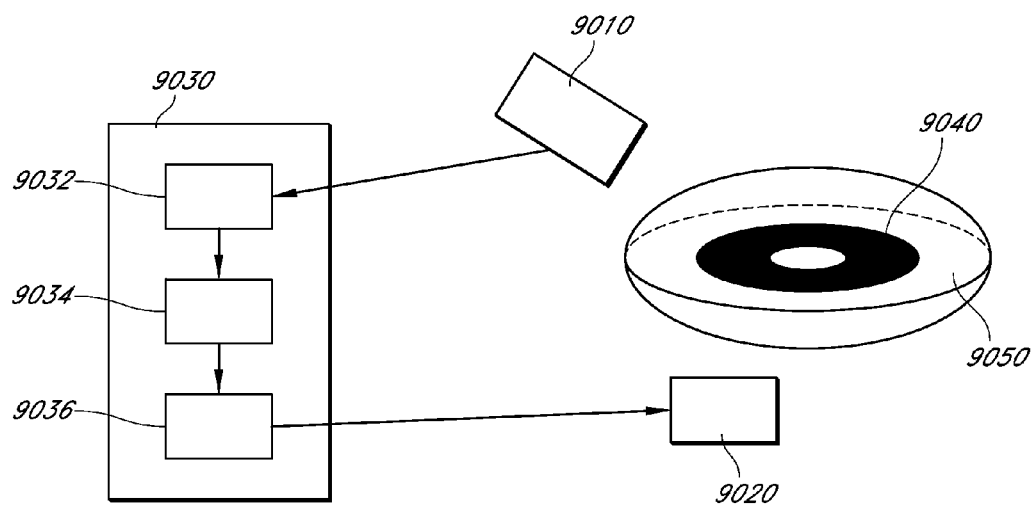
FIG. 40 is a schematic of an embodiment of a mask positioning system for positioning a mask within a mold cavity as described herein.

There are also a number of methods of positioning and adjusting the mask within a mold cavity of a mold. For example, a single mold can be used while the position of a mask within the mold cavity can be adjusted to accurately position mask relative to the mold cavity and eventually the implant body. FIG. 40 illustrates an embodiment of a mask positioning system 9000 that includes positioning sensors 9010, a mask positioning apparatus 9020, and a control system 9030. The control system 9030 can include sensor interface 9032 in electrical communication with a feedback control 9034 that is in electrical communication with a mask positioning interface 9036. The mask positioning apparatus 9020 can position the mask 9040 within the implant body 9050.

The positioning sensors 9010 can be used to measure the position of the mask within the mold cavity. For example, a Hal Effect sensor can detect magnetic fields, and the sensor's output voltage can vary in response to changes in a magnetic field. With a fixed magnetic field, the distance to the source of the field can be accurately calculated. Diamagnetic levitation and induction levitation are options that can be used with a magnetic mask. Cameras, ultrasonic detectors, capacitive proximity sensors, and laser interferometry can also be used to measure the position of the mask.

Figure 41:
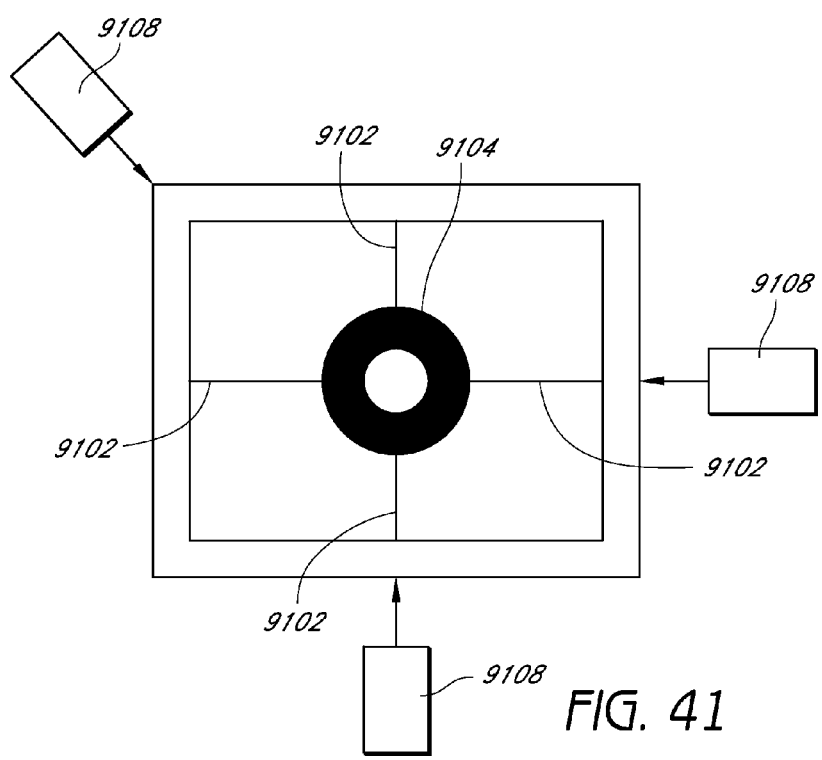
FIG. 41 is an illustration of an embodiment of a mask positioning apparatus that includes wires coupled to a mask and a frame as described herein.

A number of types of mask positioning apparatuses 9020 and methods can be used to move and position the mask within the mold cavity. For example, wires, such as nanowires, can be coupled to the mask and a frame such as a frame that surrounds the mask. FIG. 41 illustrates an embodiment of a mask positioning apparatus 9100 that includes four nanowires 9102 that are coupled to four areas on the mask 9104 at 0, 90, 180, and 270 degree positions on the mask 9104 to a surrounding frame 9106. The frame 9106 can then be moved to position the mask 9104 with, for example, mechanical actuators and/or servos 9108. Nanowires can be formed by electrodeposition. In certain embodiments, the mask and nanowires are electrodeposited to form a monolithic structure. Since the mask can have a low mass, small wires such as nanowires could be sufficient to move the mask around within a liquid polymer, and could be easily broken or sheared off from the implant body after the polymer has solidified or cured. One advantage of nanowires is that they are small and would minimize optical performance of the intraocular implant. In certain embodiments, the wires can also themselves provide the movement of the mask thereby eliminating the use of external actuators.

The wires could include a shape memory alloy such as nitinol which, when heated can deform to cause movement of the mask. Nitinol wires can be, for example, about 0.003 inches in diameter.

Figure 42:
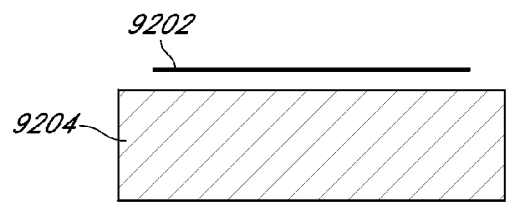
FIG. 42 is a side view of an embodiment of a mask levitated with a magnetic field as described herein.
Figure 43A:
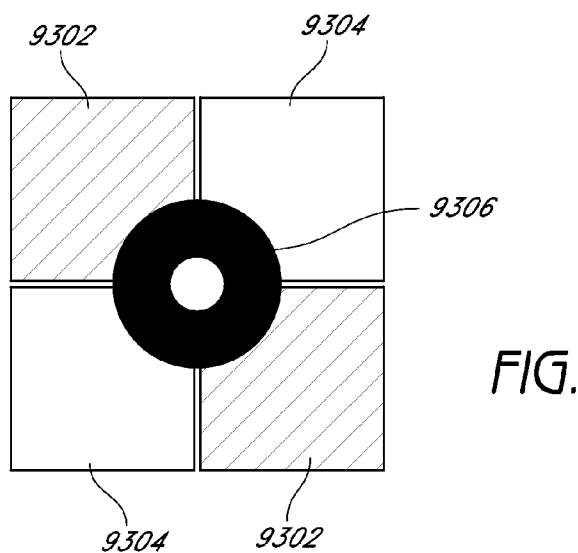
FIG. 43A is a top view of an embodiment of a mask levitated above of magnetic fields as described herein.
Figure 43B:
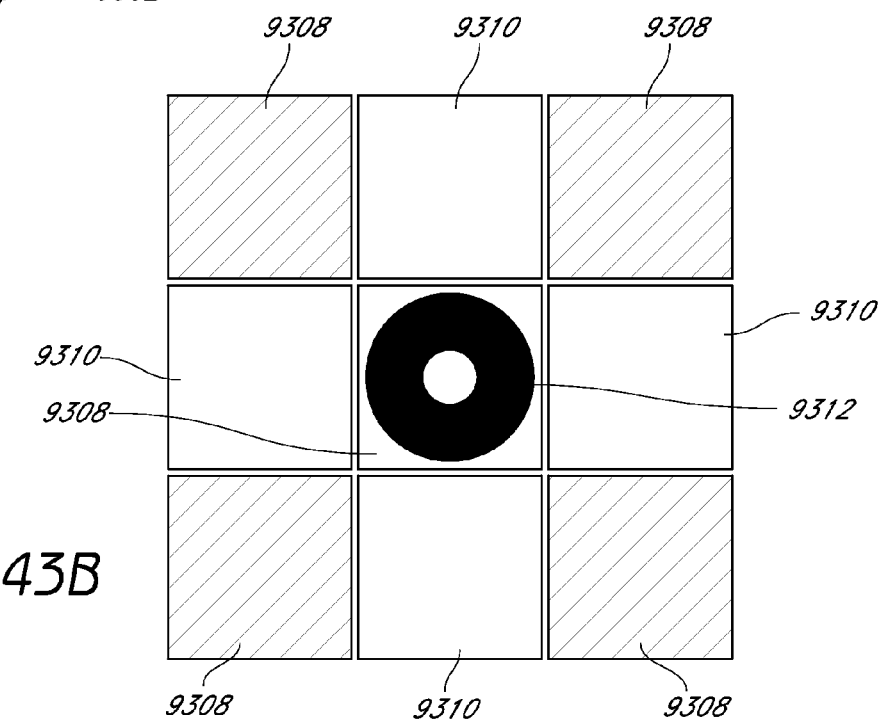
FIG. 43B is a top view of another embodiment of a mask levitated above of magnetic fields as described herein.

Diamagnetic levitation can also be used to position the mask. A diamagnetic substance is one whose atoms have no permanent magnetic dipole moment. When an external magnetic field is applied to a diamagnetic substance a weak magnetic dipole moment is induced in the direction opposite the applied field. Pyrolytic graphite is strongly diamagnetic, and pyrolytic graphite has a specific gravity around 2.1, so it is easily levitated. Diamagnetic levitation occurs by bringing a diamagnetic material in close proximity to material that produces a magnetic field. The diamagnetic material will repel the material producing the magnetic field. Most substances that are not magnetic are weakly diamagnetic. The repulsive force may not be strong enough to overcome the force of gravity. To cause diamagnetic levitation, both the diamagnetic material and magnetic material produce a combined repulsive force to overcome the force of gravity. The magnetic field can be from a permanent magnet or can be from an electromagnet. The mask 9202 can be a diamagnetic material that can be levitated with a magnetic field 9204, as illustrated in FIG. 42. The magnetic field can be manipulated to position the mask within a mold cavity. For example, the magnetic field can be configured to constrain the mask while also levitating it. Multiple magnetic field (e.g., magnets) can be used to control the properties and shape of the magnetic field. FIGS. 43A and 43B illustrate top views of examples of first magnetic fields 9302, 9308 and second magnetic fields 9304, 9310 that can constrain a mask 9306, 9312. The first magnetic fields 9302, 9308 have an opposite magnetic field as the second magnetic fields 9304, 9310. In certain embodiments, the mask includes a permanent magnetic field. If the mask has a permanent magnetic field, more force between the mask and the magnetic fields may be able to be produced.

Figure 44:
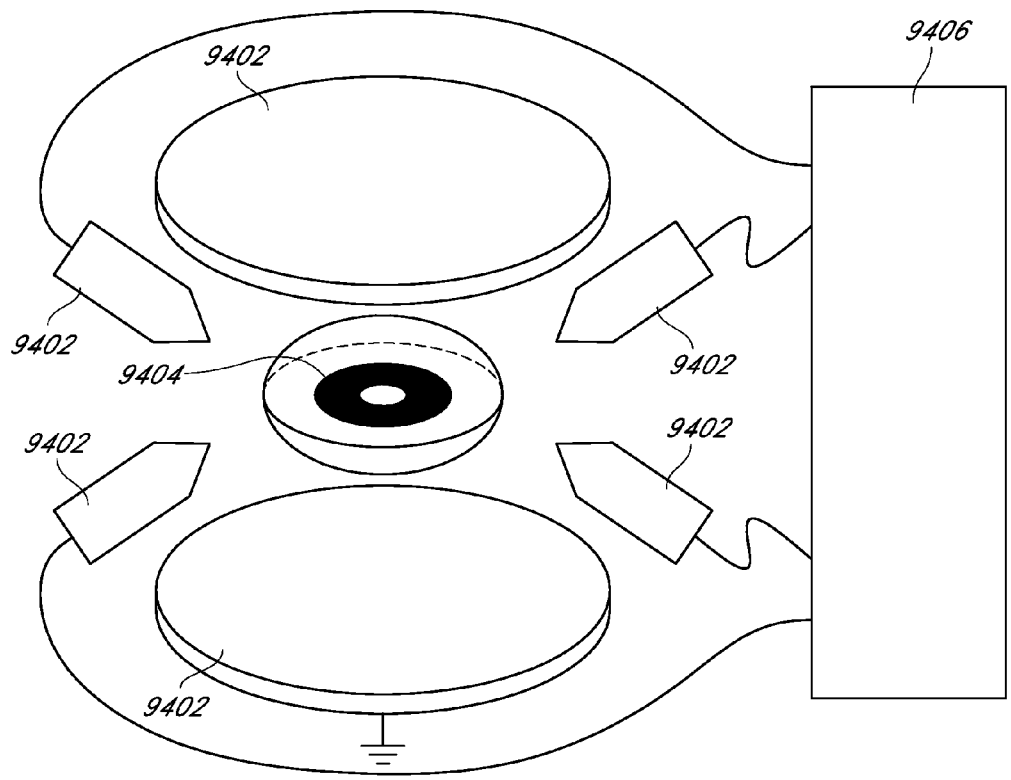
FIG. 44 is a schematic of an embodiment of using electrostatic levitation to position a mask as described herein.

A mask may also be levitated by using sonic levitation. Acoustic radiation pressure can produce intense sound wave in the liquid polymer to move the mask. Electrostatic levitation can also be used by applying an electrostatic field to the mask to counterbalance gravity. High voltage electrodes 9402 can be oriented around the mask 9404, as illustrated in FIG. 44. For example, two electrodes 9402 can be oriented on opposite sides of the mask 9404 on each of three axes that are perpendicular to each other for a total of six electrodes. The electrodes can be in electrical communication with a high voltage generator and controller 9406.

Figure 45:
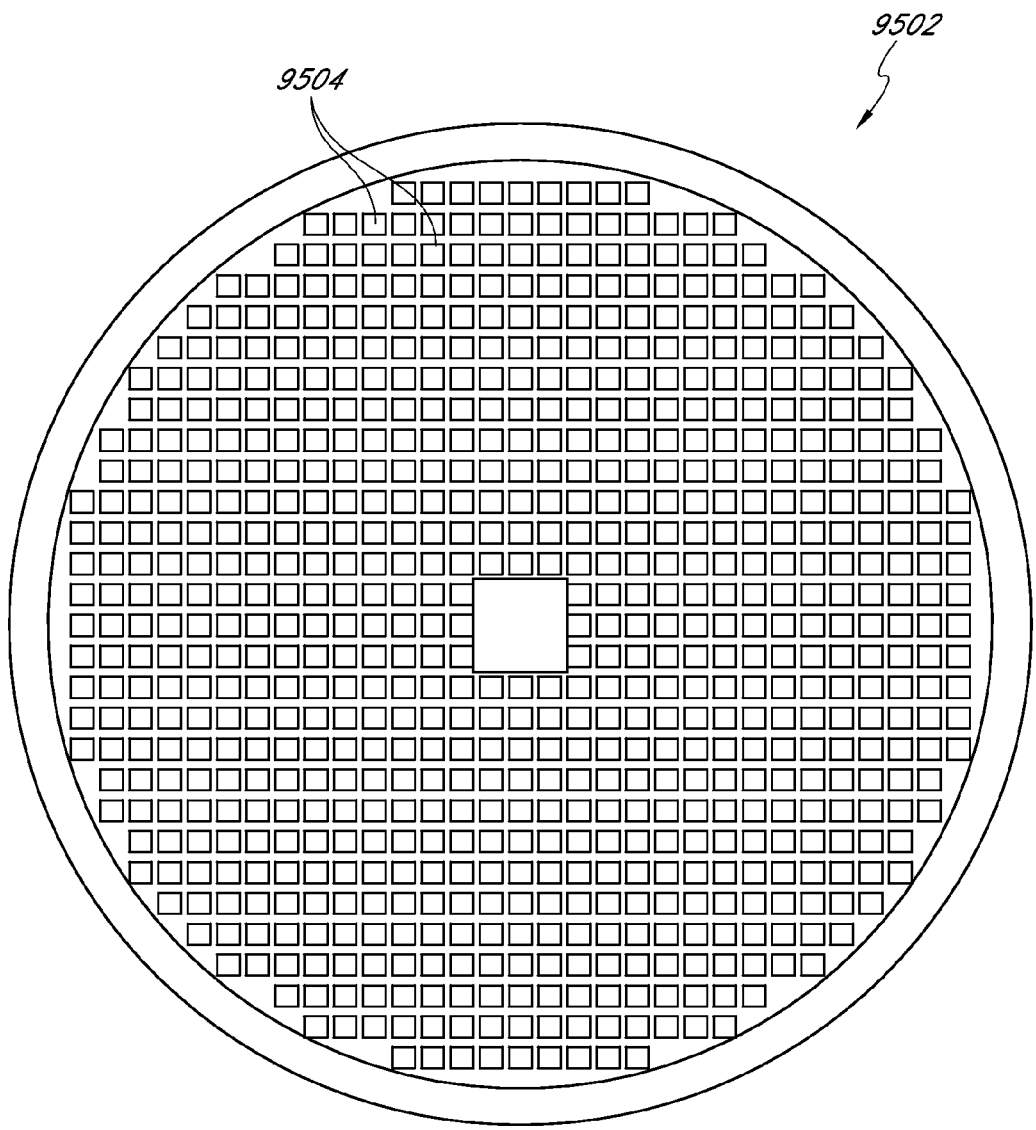
FIG. 45 is a top view of an embodiment of a bistable display that is capable of forming a mask as described herein.

The mask may be formed by a bistable display (e.g., Cholesteric Liquid Crystal Display (ChLCD)) that is capable of maintaining a state (e.g., opaque or transparent) without electrical power. FIG. 45 illustrates a bistable display 9502. Electrical power can be used to change the state of a pixel 9504 to either opaque or transparent. The pixels that are opaque can form the mask. Therefore, the inner diameter, outer diameter, and aperture of the mask can be adjusted.

VII. Intraocular Implants with Haptics

Anterior chamber intraocular lens have generally been made from polymethyl methacrylate (PMMA), which is a relatively hard thermoplastic. A certain amount of rigidity was believed necessary to maintain stability of the implant in the anterior chamber. For example, a stiffening element can be added to the haptic to achieve the desirable stability of the intraocular lens (see, e.g., U.S. Pat. No. 6,228,115 (Hoffmann, et al.)). However, the compressive forces of PMMA intraocular lenses is far in excess of what is required for stability. It is also possible to construct intraocular lenses from soft materials such as silicones, hydrogels and soft acrylics. With these softer materials, there is some question as to the stability of the implant in the anterior chamber; however, intraocular implants made from soft material are stable when certain compressive forces and contact areas are used.

For example, the commercially available Bausch & Lomb NuVita Model MA 20 exhibits a force response of approximately 2.7 mN at 1 mm of compression when measured according to the industry standard compression test, ISO/DIS 11979-3. The intraocular implant illustrated in FIGS. 46-47 can exhibit a force response of less than approximately 0.5 mN at 1 mm of compression when made from a soft acrylic material, which is similar to the commercially available Alcon Model SA30EL posterior chamber lens. The broad haptic contact areas found on posterior chamber IOLs such as the Alcon Model SA30EL are generally not suitable for implantation in the anterior chamber because such designs can cause translational movement of the haptic contact points relative to the anterior chamber tissue, resulting in chronic irritation and the formation of synechia. The formation of calluses around the haptics may also cause late-onset glaucoma. Advantageously, an intraocular implant having haptics that contact the anterior chamber angle at only four locations, and with a ratio of haptic spread to optic diameter of less than 1.5, and preferably around 1.3 for a 5.5 mm optic provides sufficient stability without excessive angle contact.

Figure 46:
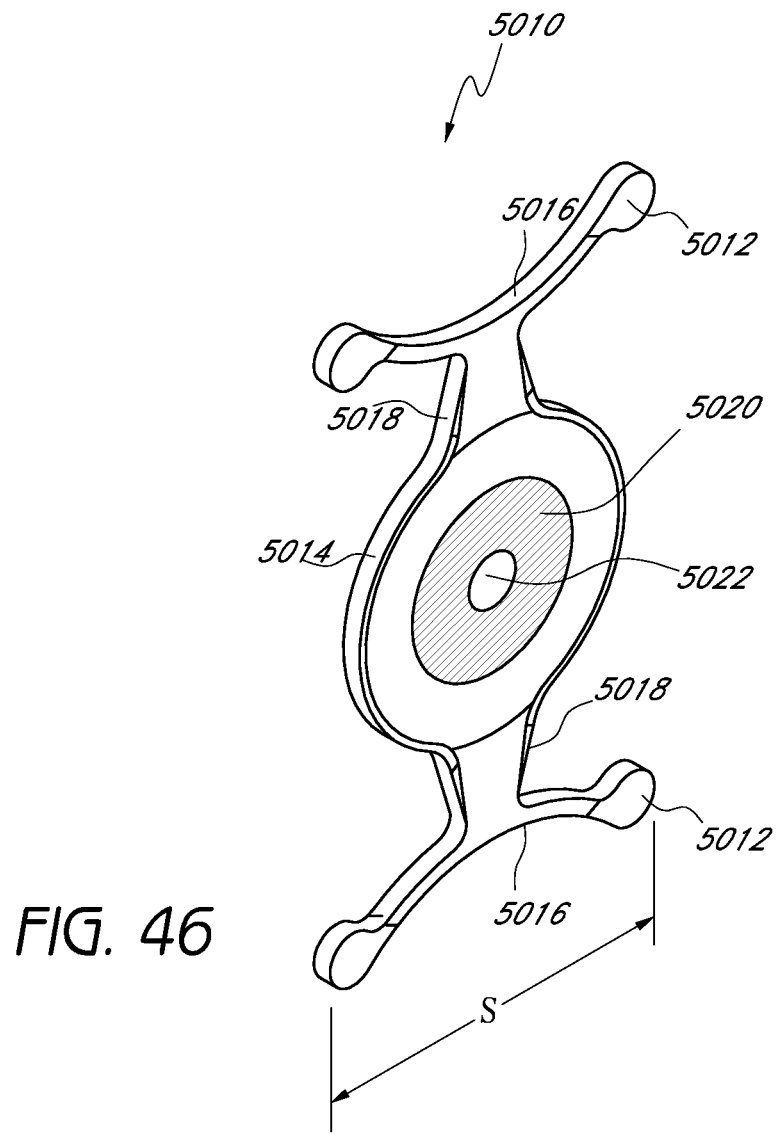
FIG. 46 is a top perspective view of an embodiment of a masked intraocular implant configured to increase depth of focus described herein.
Figure 47:
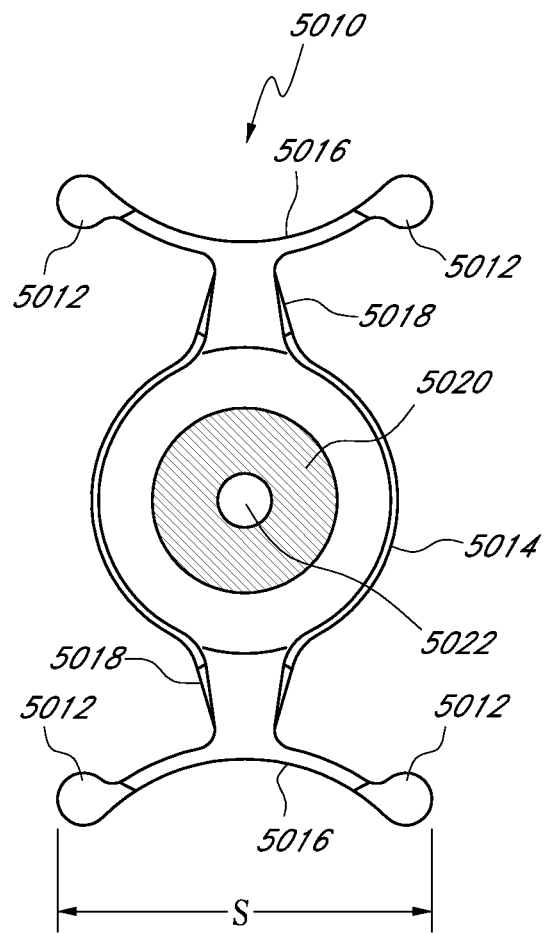
FIG. 47 is a top plan view of the intraocular implant of FIG. 46.

As illustrated in FIGS. 46 and 47, an intraocular implant 5010 can include an intraocular body 5014 with a mask 5020 in or on the implant body 5014. The implant body 5014 can include a lens body. For example, the lens body can include any lens body described herein. In addition, the intraocular implant 5010 can be implanted in phakic or aphakic patients.

In certain embodiments, the intraocular implant 5010 includes a mask 5020 embedded in or carried by a single piece comprising a soft acrylic, such as those described in U.S. Pat. Nos. 5,290,892, 5,403,901, 5,433,746, 5,674,960, 5,861,031 and 5,693,095, the disclosures of which are hereby incorporated by reference in their entirety. Such a material allows the intraocular implant 5010 to be rolled or folded so as to fit through a 3.5 mm or less surgical incision and implanted in the anterior chamber of an eye. The intraocular implant 5010 may also be made from a soft silicone or hydrogel material. In certain embodiments, the intraocular implant 5010 includes two opposing pairs of footplates 5012 joined to the implant body 5014 by haptics 5016 and ramps 5018. The implant body 5014 may have any suitable diameter, but is preferably between 5.0 mm and 6.0 mm. The footplates 5012 are separated by the haptic 5016 by a distance S, that is preferably less than 1.5 times the diameter of implant body 5014, and most preferably around 1.3 times the diameter of implant body 5014. The footplates 5012 and haptics 5016 preferably are between 0.20 and 0.30 mm thick, which provides sufficient compressive force, while minimizing axial vaulting of intraocular implant 5010 to less than 1.5 mm and preferably less than 1.0 mm when the footplates 5012 and haptics 5016 are compressed 1 mm. As discussed above, the compressive force of the haptics 5016 and footplates 5012 can be sufficient for the stability of intraocular implant 5010, but not so large to cause irritation or pupil ovaling. Preferably, the intraocular implant 5010 exhibits a force response of approximately less than 0.5 mN, and more preferably, approximately less than 0.3 mN, when the intraocular implant 5010 is compressed 1 mm according to industry standard test ISO/DIS 11979-3.

Figure 48A:
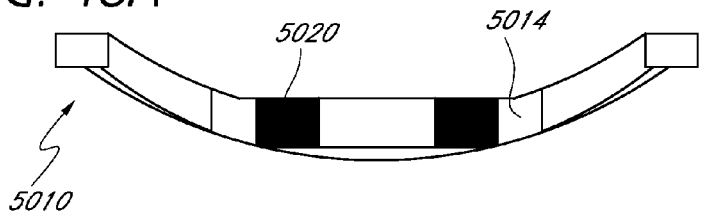
FIG. 48A is a side elevational view of an embodiment of an intraocular implant with a mask through the intraocular implant of FIG. 46.

The mask 5020 has an aperture 5022 to improve the depth of focus of a human eye. In certain embodiments, the aperture 5022 is a pin-hole aperture. The mask 5020 can extend through the entire anterior-posterior dimension of the implant body 5014, as illustrated in FIG. 48A. Preferably, the mask will be no more than about 85% or 95% of the anterior-posterior thickness of the finished lens, so that the material of the lens body will overlay and encapsulate the mask to provide a continuous outer surface.

The implant of FIG. 46, and other implants described below can be manufactured by lamination, or other techniques known in the art. For example, the mask may be placed into a mold cavity followed by introduction of monomer, polymer or other lens precursor material which is caused to change from a flowable state to a solid state to encapsulate the mask.

Figure 48B:
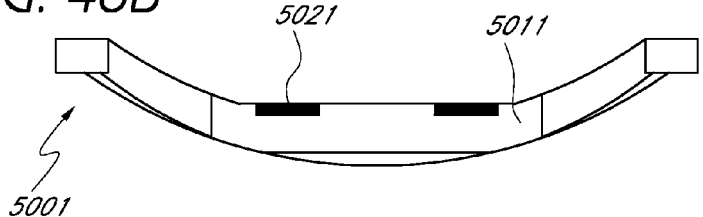
FIG. 48B is a side elevational view of an embodiment of an intraocular implant with a mask on the posterior surface of the intraocular implant.
Figure 48C:
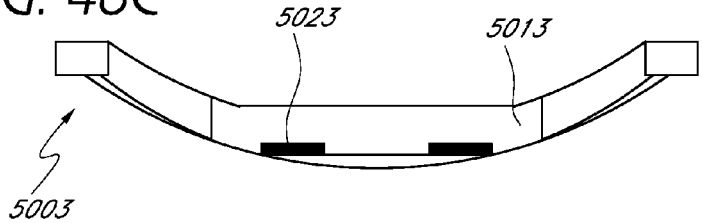
FIG. 48C is a side elevational view of an embodiment of an intraocular implant with a mask on the anterior surface of the intraocular implant.
Figure 48D:
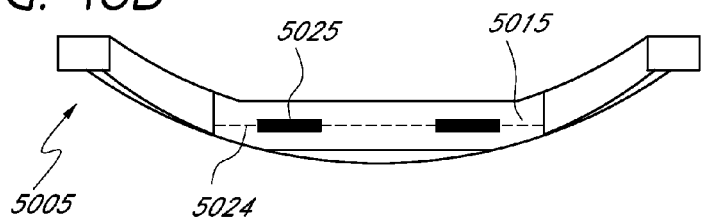
FIG. 48D is a side elevational view of an embodiment of an intraocular implant with a mask positioned midway between the posterior and anterior surfaces of the intraocular implant.
Figure 48E:
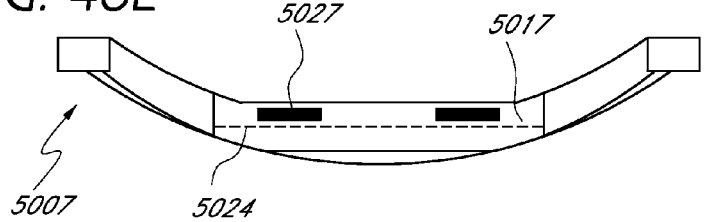
FIG. 48E is a side elevational view of an embodiment of an intraocular implant with a mask positioned between the posterior surface and a midway position between the posterior and anterior surfaces of the intraocular implant.
Figure 48F:
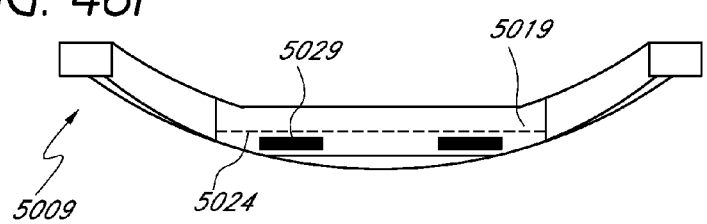
FIG. 48F is a side elevational view of an embodiment of an intraocular implant with a mask positioned between the anterior surface and a midway position between the posterior and anterior surfaces of the intraocular implant.
Figure 51A:
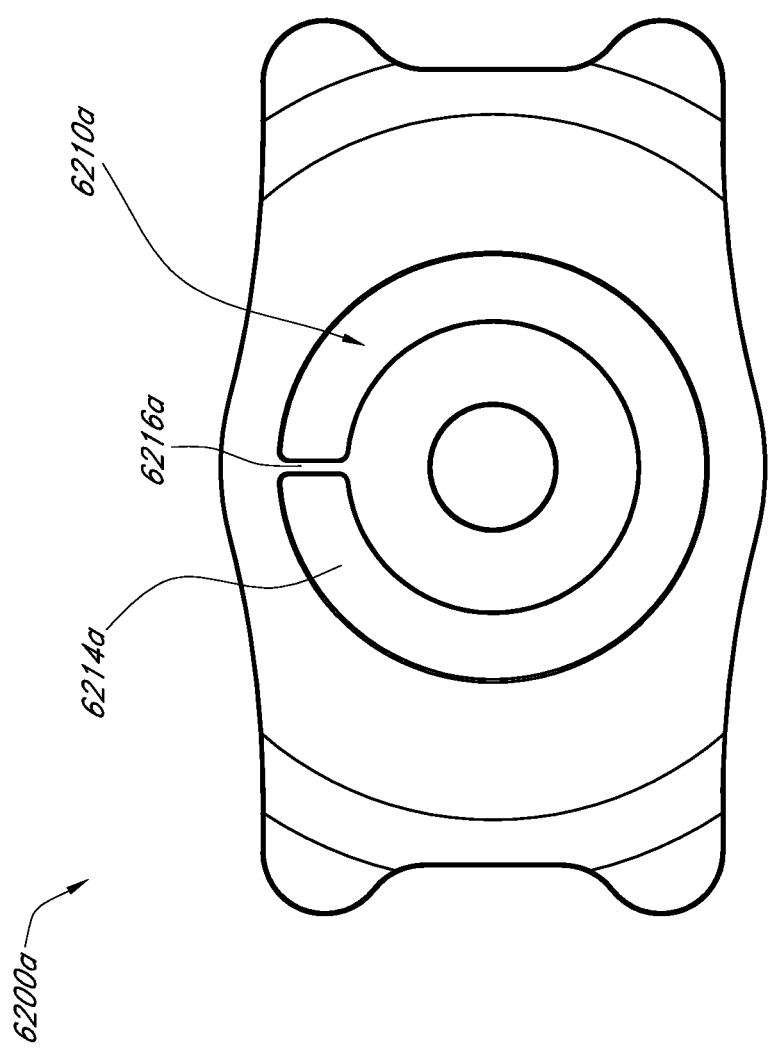
FIG. 51A is a top plan view of an embodiment of an intraocular implant with a single outer hole described herein.
Figure 51C:
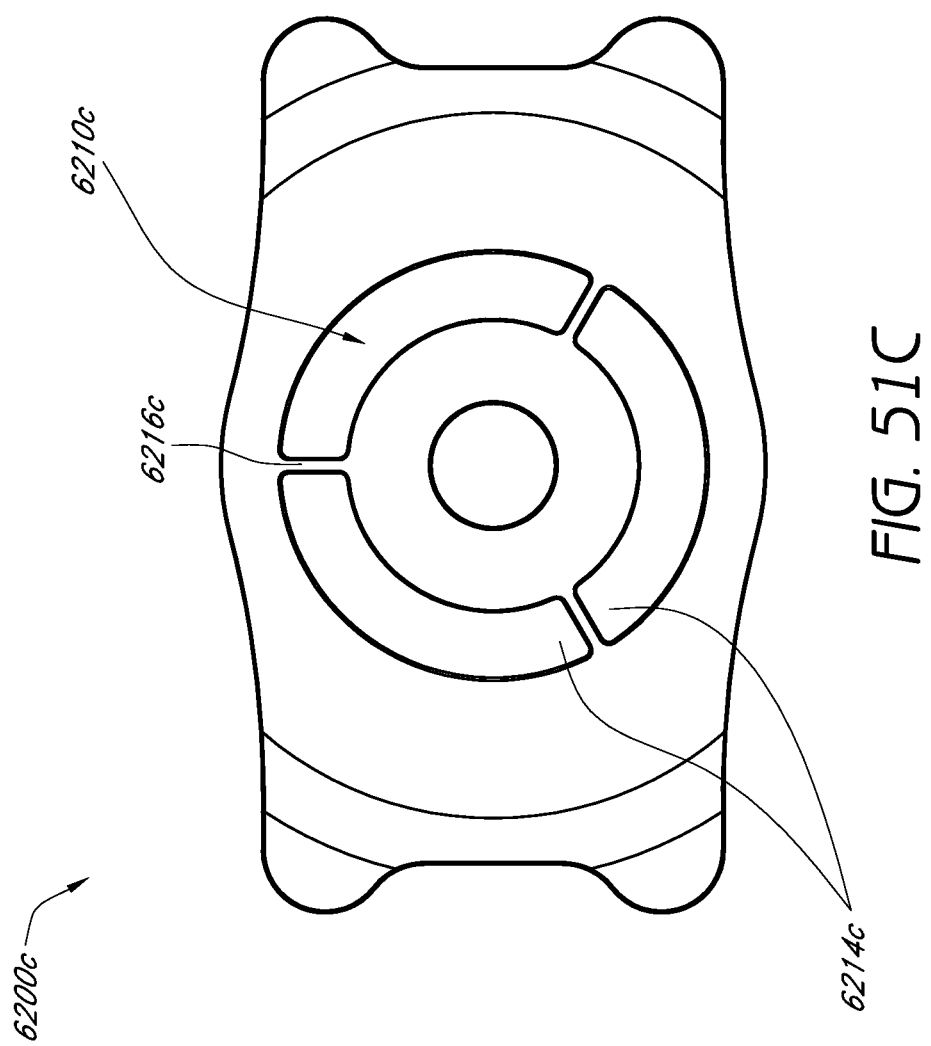
FIG. 51C is a top plan view of an embodiment of an intraocular implant with three outer holes described herein.
Figure 51D:
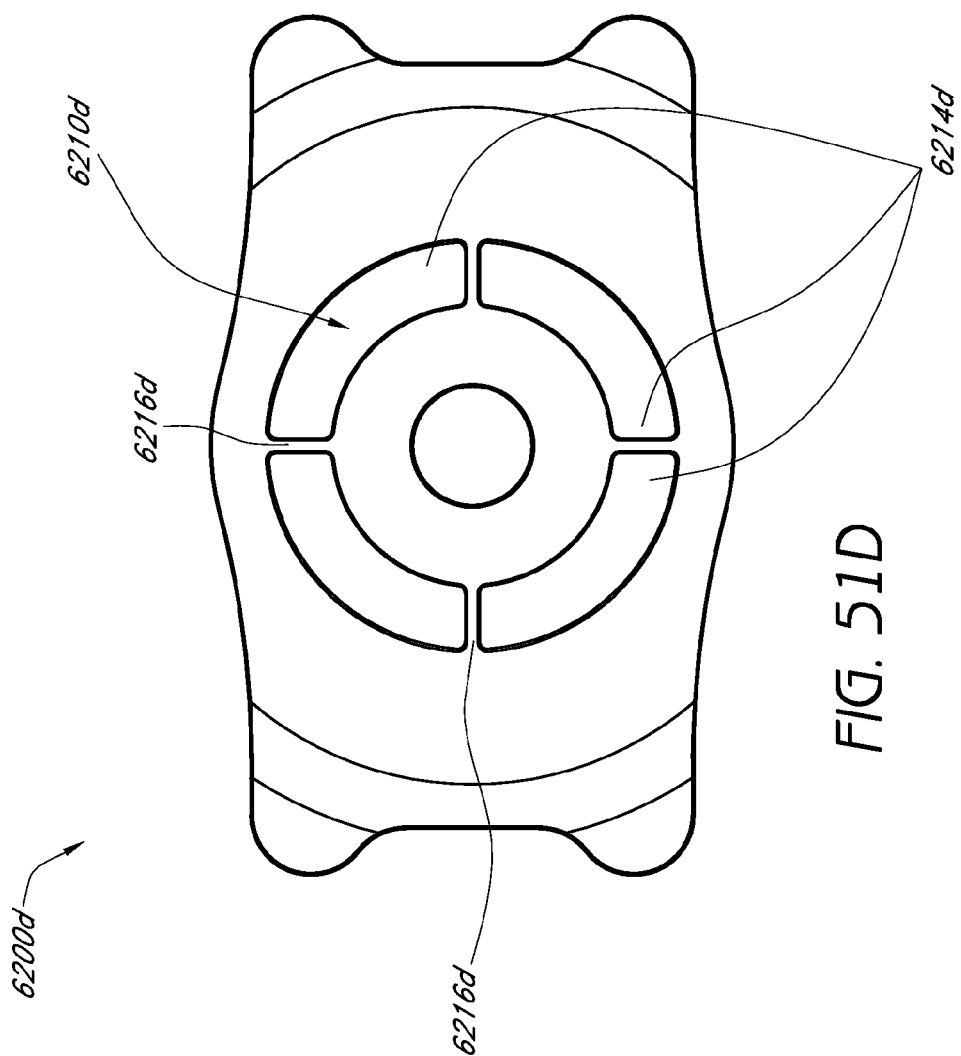
FIG. 51D is a top plan view of an embodiment of an intraocular implant with four outer holes described herein.

The mask 5021, 5023 can be positioned on, neighboring, near or adjacent the anterior or posterior surface of the implant body 5011, 5013, as illustrated in FIGS. 48B and 48C, respectively. In certain embodiments, the mask is spaced apart from the surfaces of the implant body. For example, the mask 5025 can be positioned substantially at a central portion 5024, e.g., midway between the posterior and anterior surfaces of the implant body 5015, as illustrated in FIG. 48D. In certain embodiments, the mask 5027 is positioned between the central portion 5024 and the posterior surface of the implant body 5017, as illustrated in FIG. 48E. Certain embodiments include the mask 5027 being positioned midway, one-third or two-thirds between the central portion 5024 and the posterior surface of the implant body 5017. In certain other embodiments, the mask 5029 is positioned between the central portion 5024 and the anterior surface of the implant body 5019, as illustrated in FIG. 48F. Certain embodiments include the mask 5029 being positioned midway, one-third or two-thirds between the central portion 5024 and the anterior surface of the implant body 5019.

VIII. Intraocular Implants with Masks

Intraocular implants for improving the vision of a patient, such as by increasing the depth of focus of an eye of a patient, can include different types of structures. FIGS. 49A-C illustrate an embodiment of intraocular implant 6000 with an implant body 6002. The implant body 6002 can include a mask 6006, an aperture 6008 surrounded by the mask 6006, and an outer hole region 6010 around the mask 6006. The outer hole region 6010 can have an outer portion 6012 of the implant body 6002 around it.

The intraocular implant 6000 may include one or more haptics 6004 to prevent the intraocular implant 6000 from moving or rotating within the eye. The haptics 6004 can be a variety of shapes and sizes depending on the location the intraocular implant 6000 is implanted in the eye. For example, the haptics 6004 illustrated in FIGS. 49A-C and the haptics 6104 illustrated in FIGS. 50A-C have different haptics. The haptics 6004, 6104 illustrated FIGS. 49-50 are generally suited for sulcus fixated intraocular implants 6000, 6100; however the intraocular implants 6000, 6100 can be interchanged with any variety of haptic (e.g. haptics described above), and can be implanted into any suitable location within the eye (e.g. anterior chamber and posterior chamber).

As illustrated in FIGS. 49A and 49B, the outer hole region 6010 includes five outer holes 6014 that form an annulus around the aperture 6008. The outer hole region 6010 can include one or more connection portions 6016. The connection portions 6016 can be between at least two of the outer holes 6015. The connection portion 6016 connects or links the mask 6006 and the outer portion 6012 of the implant body 6002. In certain embodiments, the mask 6006, the connection portions 6016 and the outer portion 6012 are a single integrated piece. In certain embodiments, the single integrated piece also includes haptics 6004. The outer holes 6014 can be formed into the single integrated piece by stamped, cutting, burning, etching, etc.

In certain embodiments, at least a portion of the implant body is opaque. As used herein the term "opaque" is intended to indicate a transmission of no more than about 2% of incident visible light. In one embodiment, at least a portion of the implant body 6002 is configured to be opaque to more than 99% of the light incident thereon. In certain embodiments, at least a portion of the mask 6006 is opaque. In certain other embodiments, at least a portion of the mask 6006 is configured to transmit between 2 and 5% of incident visible light. In certain embodiments, the mask 6006 transmits no more than 95% of incident visible light. In certain embodiments, the intraocular implant 6000 is a single integrated opaque piece.

The size of the aperture 6008 may be any size that is effective to increase the depth of focus of an eye of a patient suffering from presbyopia. For example, the aperture 6008 can be circular. In one embodiment, the aperture 6008 has a diameter of less than about 2 mm. In another embodiment, the diameter of the aperture is between about 1.6 mm and about 2.0 mm. In another embodiment, the aperture 6008 has a diameter of about 1.6 mm or less. In another embodiment, the diameter of the aperture is about 1.4 mm. In certain embodiments, the diameter of the aperture is between about 0.85 mm to about 2.2 mm. In further embodiments, the diameter of the aperture is between about 1.1 mm to about 1.7 mm.

In certain embodiments, the outer hole region 6010 of intraocular implant s 6000 can improve low light vision. As the pupil of the eye enlarges, eventually light rays will enter and pass through the outer hole region 6010 of the intraocular implant 6000. If the pupil of the eye is large enough so that light rays pass through outer hole region 6010 of the intraocular implant 6000, additional light rays will strike the retina.

The outer hole region 6010 can be a variety of shapes and sizes. FIGS. 51-54 illustrate various embodiments of intraocular implants. FIGS. 51A-E illustrate intraocular implants similar to the intraocular implant 6000 of FIGS. 49A-C except that the number of connection portions 6016 that connect the mask 6006 with the outer portion 6012 of the implant body 6002 and the number of outer holes 6014 vary. FIGS. 51A, 51B, 51C, 51D and 51E illustrate intraocular implants 6200a, 6200b, 6200c, 6200d, 6200e with one connection portion 6216a and one outer hole 6214a in the outer hole region 6010a, with two connection portions 6216b and two outer holes 6214b in the outer hole region 6010b, with three connection portions 6216c and three outer holes 6214c in the outer hole region 6010c, with four connection portions 6216d and four outer holes 6214d in the outer hole region 6010d, and with six connection portions 6216e and six outer holes 6214e in the outer hole region 6010e, respectively.

Intraocular implants 6000 can have any number of connection portions 6016. Embodiments include intraocular implants with at least one connection portion, at least two connection portions, at least three connection portions, at least four connection portions, at least five connection portions, at least six connection portions, less than ten connection portions, less than six connection portions, between one and ten connection portions.

Similarly, intraocular implants 6000 can have any number of outer holes 6014. Embodiments include intraocular implants with at least one outer hole, with at least two outer holes, with at least three outer holes, with at least four outer holes, at least five outer holes, at least six outer holes, less than ten outer holes, less than six outer region holes, between one and ten outer region holes.

In certain embodiments, the cross-sectional area perpendicular to the length of an outer hole of at least one outer hole is at least about 1 mm$^2$. In certain embodiments, the cross-sectional area perpendicular to the length of the outer holes of at least two outer holes is at least about 1 mm$^2$ for each of the at least two outer holes. In certain embodiments, area on the implant body of the outer hole region is at least about 5 mm$^2$ or at least about 10 mm$^2$.

The distance between the outer perimeter 6018 of the aperture 6008 (e.g. inner perimeter 6018 of the mask 6006) and outer perimeter 6020 of the mask 6006 can also vary. For example, the distance between the outer perimeter 6018 of the aperture 6008 and outer perimeter 6020 of the mask 6006 can be adjusted depending on the particular patient and the location within the eye that the intraocular implant 6000 is positioned. Embodiments include the distance between the outer perimeter 6018 of the aperture 6008 and outer perimeter 6020 of the mask 6006 to be about 1.1 mm, between about 0.8 and about 1.4 mm, between about 0.4 and about 2.5 mm, greater than zero, greater than about 0.4 mm, and greater than about 0.8 mm.

In certain embodiments, the aperture 6008 and/or the outer hole region 6010 includes an optical power and/or refractive properties. For example, the aperture 6008 and/or the outer hole region 6010 can include an optic and can have an optical power (e.g. positive or negative optical power). In certain embodiments, the aperture 6008 and/or the outer hole region 6010 can correct for refractive errors of an eye.

Figure 52:
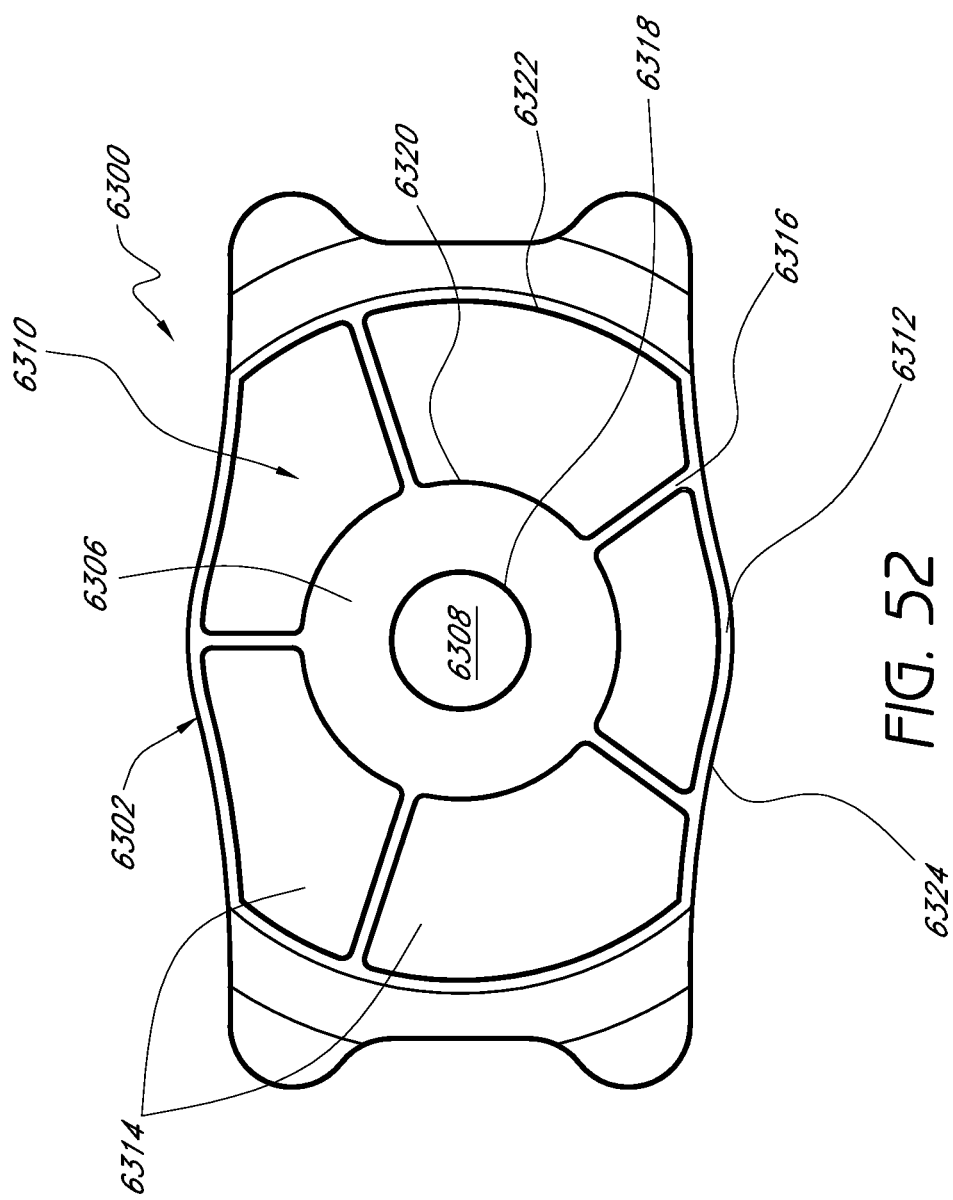
FIG. 52 is a top plan view of an embodiment of an intraocular implant with an outer hole region that extends out near the periphery of the implant body described herein.

The distance between the inner perimeter 6020 of the outer hole region 6010 (e.g. outer perimeter 6020 of the mask 6006) and the outer perimeter 6022 of the outer hole region 6010 can be a variety of sizes. Embodiments include the distance between the inner perimeter 6020 of the outer hole region 6010 and the outer perimeter 6022 of the outer hole region 6010 to be about 0.85 mm, greater than about 0.7 mm, greater than about 0.4 mm, greater than zero, between about 0.6 and about 1.0 mm, and between about 0.2 and about 1.5 mm. FIG. 52 illustrates an embodiment of an intraocular implant 6300 where the outer perimeter 6322 of the outer hole region 6310 extends to near the outer perimeter 6324 of the implant body 6302. For example, the distance between the outer perimeter 6322 of the outer hole region 6310 and the outer perimeter 6324 of the implant body 6302 can be less than 0.5 mm or less than 0.1 mm.

In certain embodiments, the outer hole region 6010 has a incident visible light transmission of at least 90% or at least 95%. In certain embodiments, the outer hole region 6010 area includes at least 90% or at least 95% outer holes 6014. In certain embodiments, the outer hole region 6010 area includes no more than 10% or no more than 5% connection portions 6016.

Figure 53A:
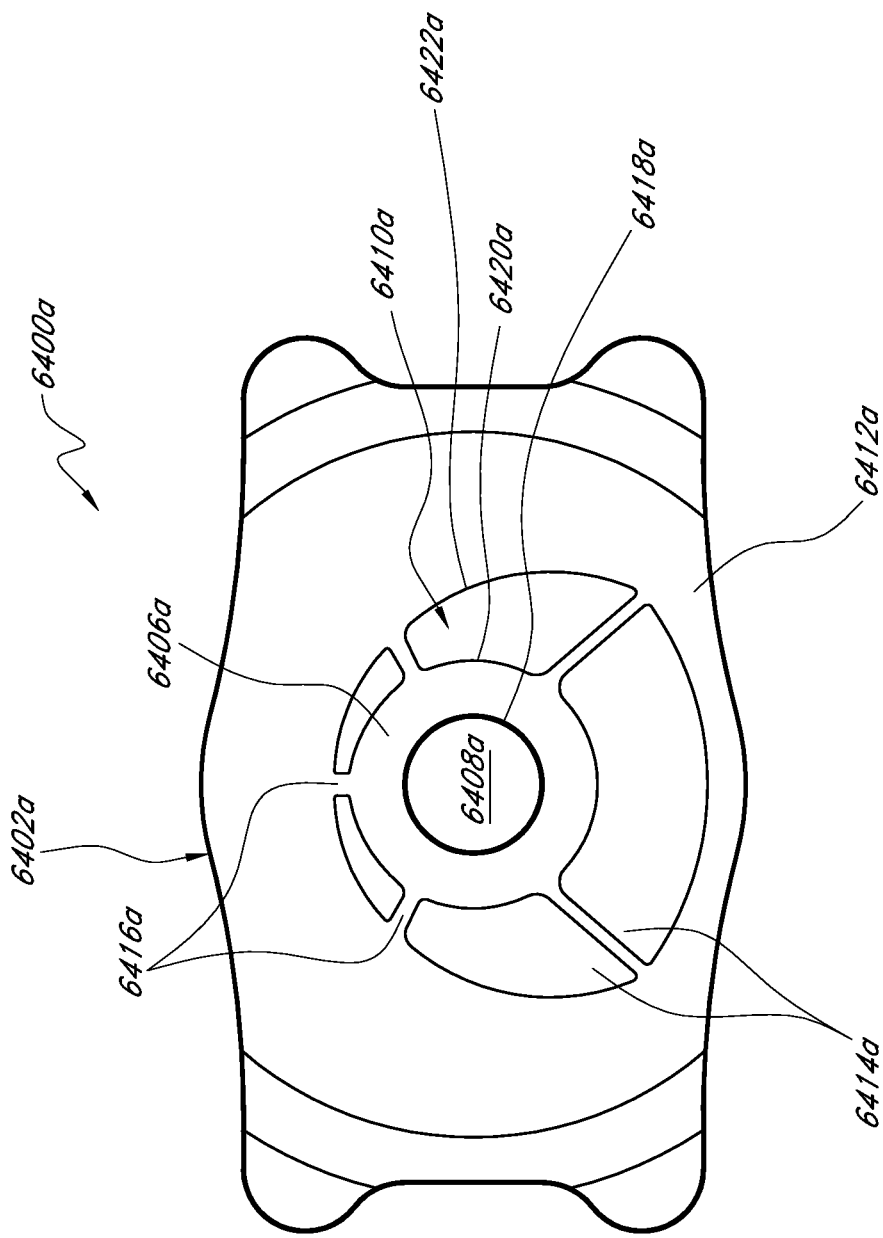
FIG. 53A is a top plan view of an embodiment of an intraocular implant with an outer hole region that extends out further away from the aperture in one direction than another described herein.
Figure 53B:
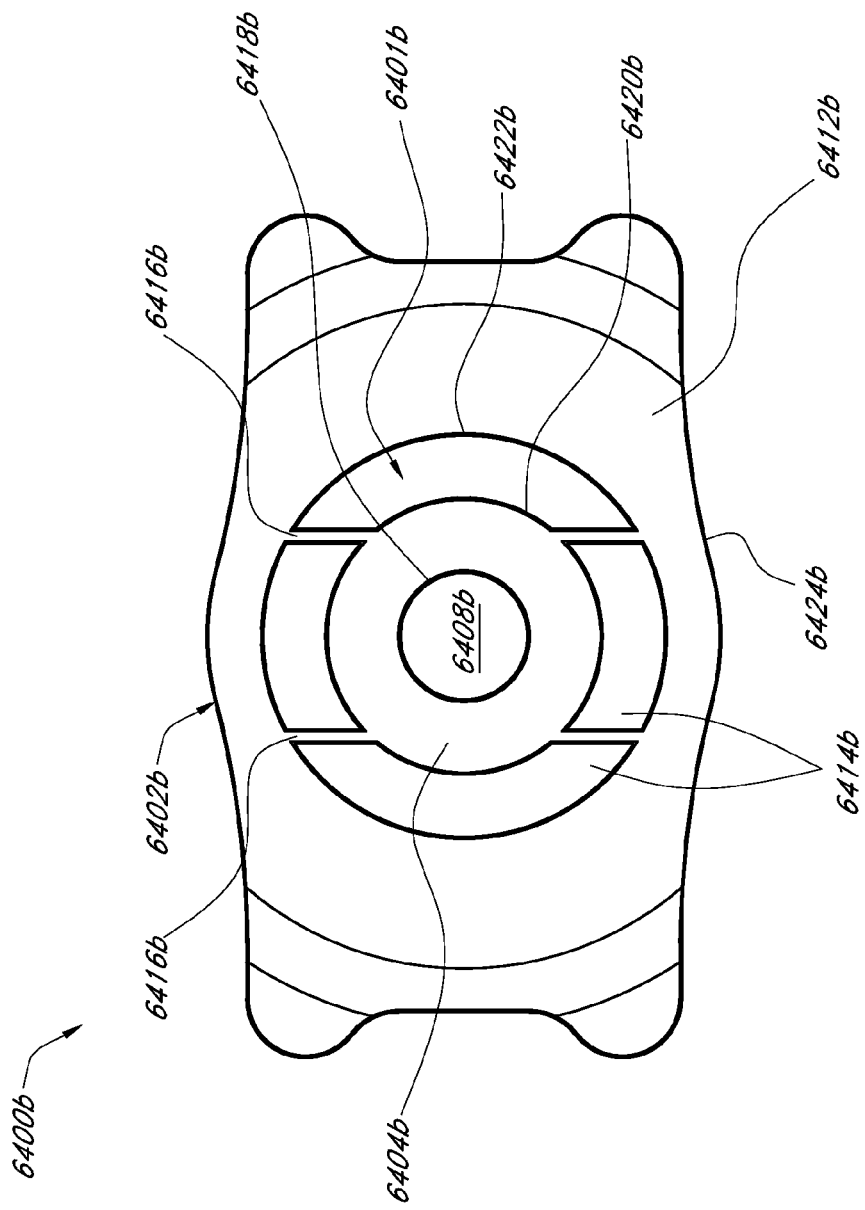
FIG. 53B is a top plan view of an embodiment of an intraocular implant with non-uniform outer holes described herein.

The outer hole region 6010 can have irregular annular shapes. FIGS. 53A-C illustrate examples of variations in annular shapes. As illustrated in FIG. 53A, the outer hole region 6410a has different sized outer holes 6414a. The distance between the inner perimeter 6420a of the outer hole region 6410a and the outer perimeter 6422a of the outer hole region 6410a can vary annularly around the outer hole region 6410a. The distance between the outer perimeter 6422a of the outer hole region 6410a and the outer perimeter 6424a of the implant body 6402a can also vary annularly around the outer hole region 6410a.

In certain embodiments, connection portions 6016 extend substantially radially out from the center of the implant body 6002, as illustrated in FIG. 49B. FIG. 53B illustrates an embodiment where the connection portions 6416b do not extend radially out from the center of the implant body 6402b. For example, the lengths of the connection portions 6416b can be substantially parallel.

In certain embodiments, the outer hole region 6010 is substantially annularly circle-shaped, as illustrated in FIGS. 49-51. As illustrated in FIG. 53C, the outer hole region 6410c can be substantially annularly square-shaped. In certain embodiments, the outer hole region 6410c is annularly polygon-shaped.

In certain embodiments, the outer hole region 6010 can be a substantially continuous annulus, as illustrated in FIGS. 49-53. As illustrated in FIG. 54, the outer hole region 6500 can have a partial annular shape. In certain embodiments, the outer hole region 6010 at least partially surrounds the mask 6506 and/or the aperture 6508.

Figure 55:
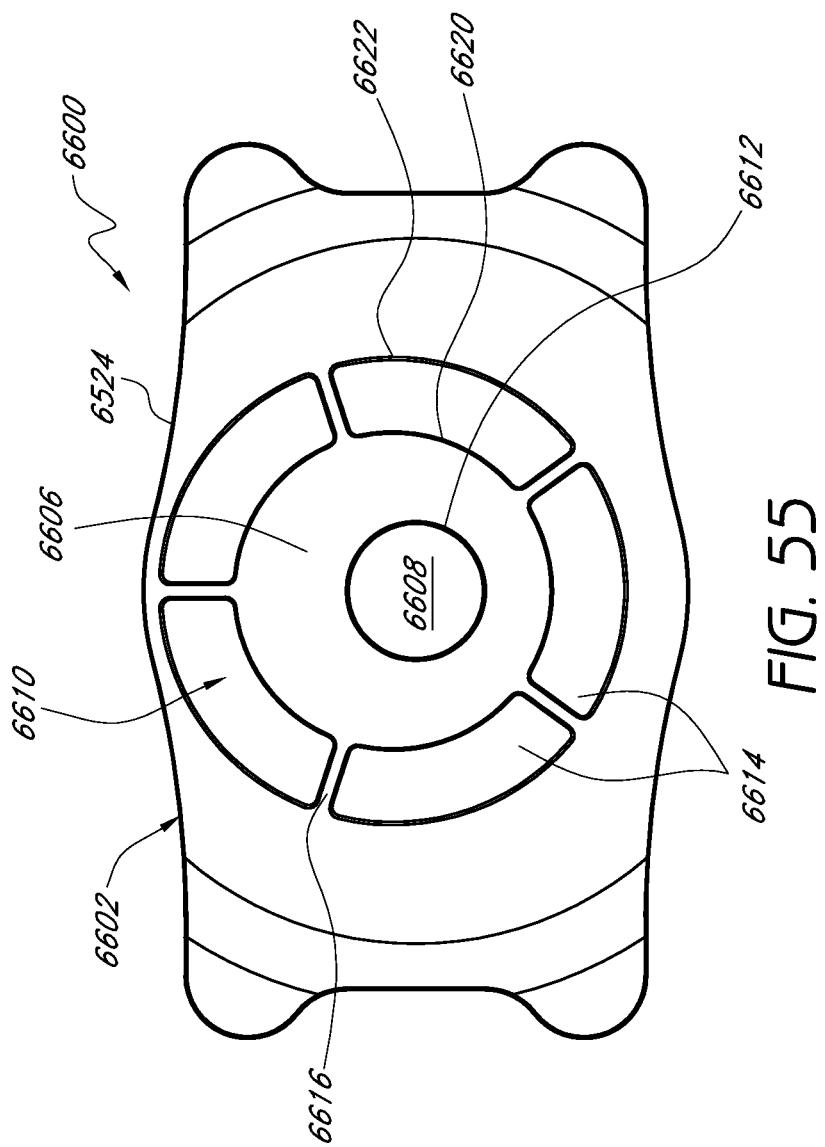
FIG. 55 is a top plan view of an embodiment of an intraocular implant with a centrally located aperture and an off-center outer hole region described herein.
Figure 56:
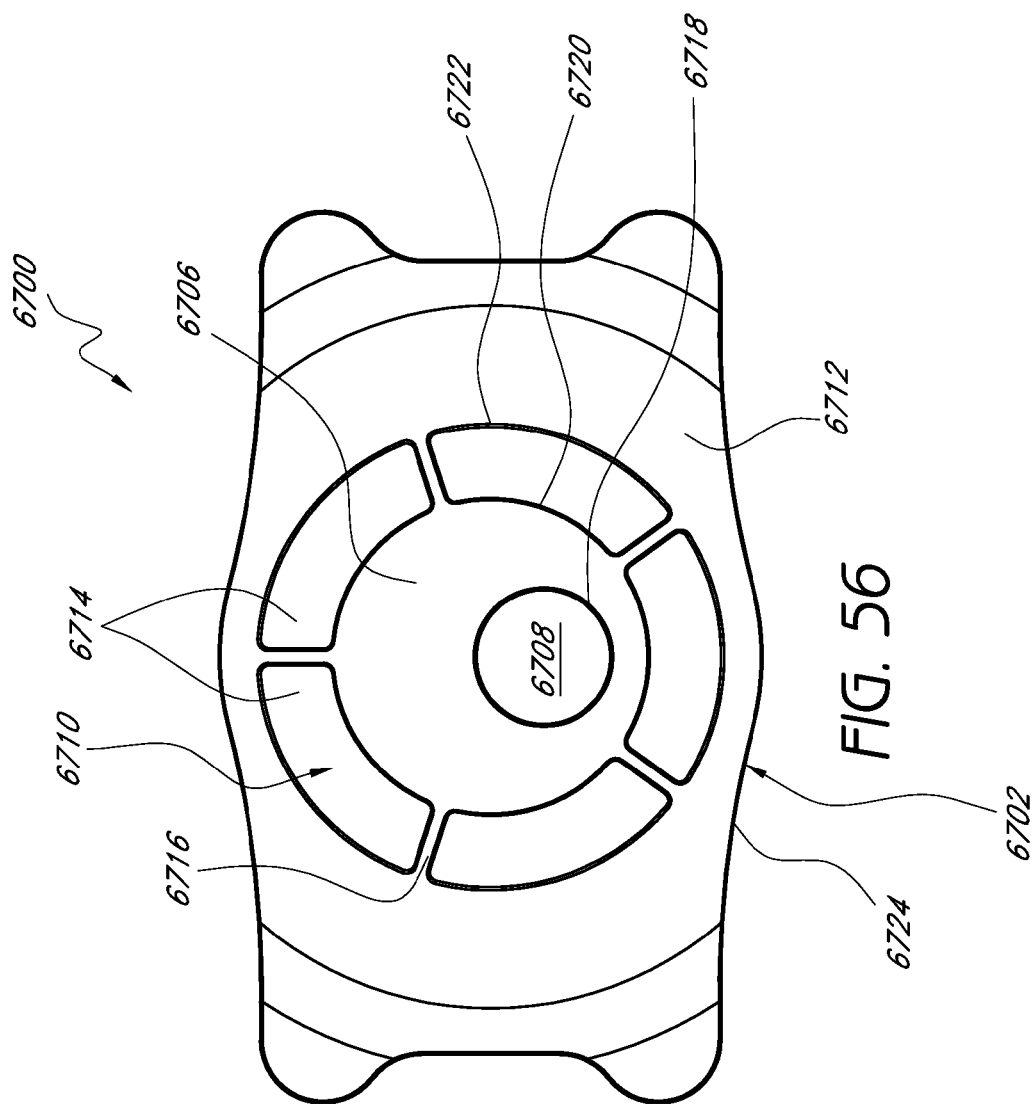
FIG. 56 is a top plan view of an embodiment of an intraocular implant with a centrally located outer hole region and an off-center aperture described herein.

In certain embodiments, the aperture 6008 is substantially centered in the mask 6006, as illustrated in FIGS. 49-53. The aperture 6608, 6708 can also be off-center in the mask 6606, 6706, as illustrated in FIGS. 55 and 56. FIG. 55 illustrates an embodiment with the aperture 6608 substantially centered in the implant body 6602 with the outer hole region 6610 off-center in the implant body 6602 (e.g. the outer hole region 6610 closer to one edge of the implant body 6602 than an opposite edge of the implant body 6602). FIG. 56 illustrates an embodiment with the outer hole region 6710 substantially centered in the implant body 6702 with the aperture 6708 off-center within the outer hole region 6710. The aperture 6008 can be substantially circular or any shape as described above.

The intraocular implant 6000 can be a variety of thicknesses (e.g. distance between the posterior and anterior surfaces). For example, the thickness of the intraocular implant 6000 can be about 0.2 mm, less than about 0.5 mm, less than about 0.3 mm, or less than about 0.2 mm.

The outer holes 6014 can be open holes or can be filled with a substantially transparent material. For example, the outer holes 6014 can be formed in the implant body 6002, and a substantially transparent material can used to fill the outer holes 6014.

Figure 57:
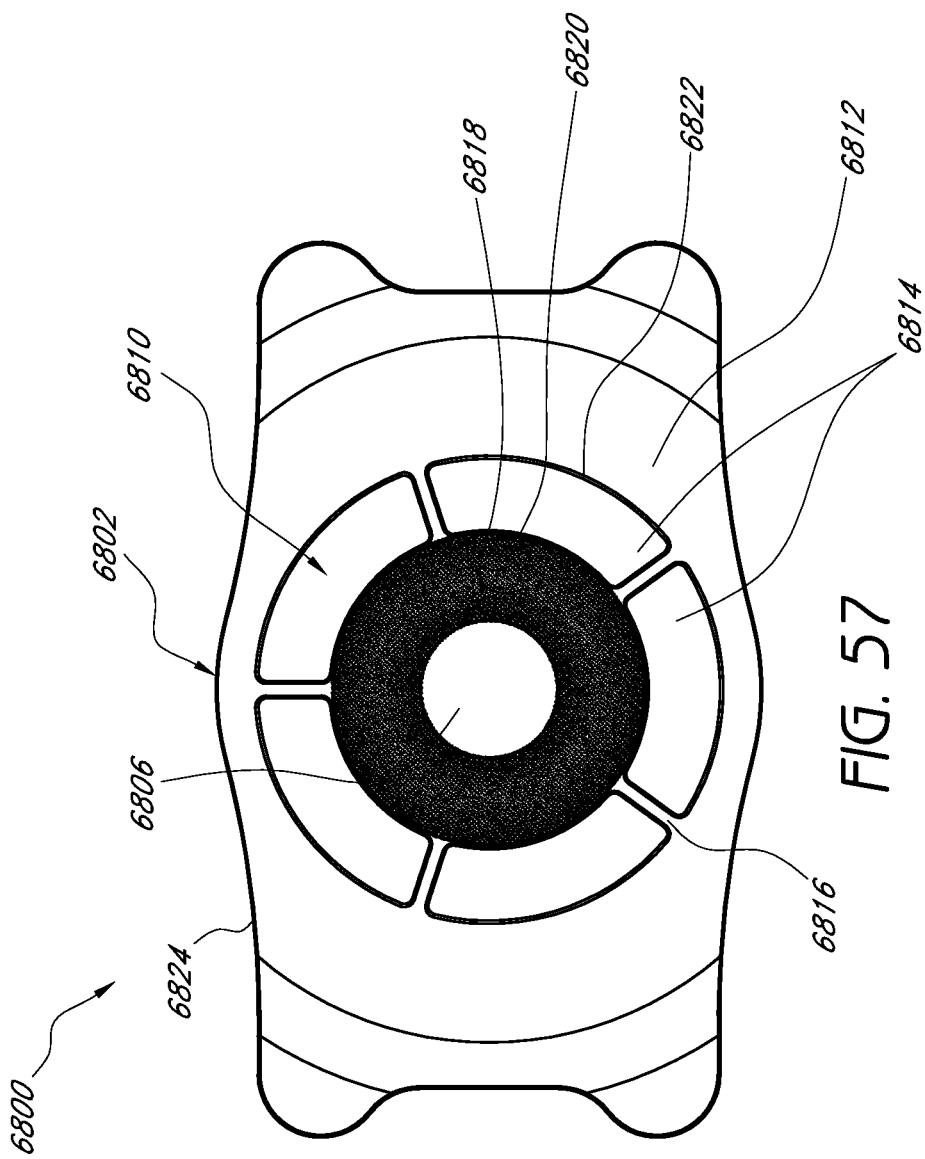
FIG. 57 is a top plan view of an embodiment of an intraocular implant wherein the mask includes light transmission holes described herein.

The mask 6006 of the intraocular implant 6000 can be any of the variations described above. In certain embodiments, the mask 6006 includes light transmission holes. For example, the configuration of the mask 4000 illustrated in FIG. 24A can be a configuration of a mask 6806 used in an intraocular implant 6800, as illustrated in FIG. 57.

Figure 58:
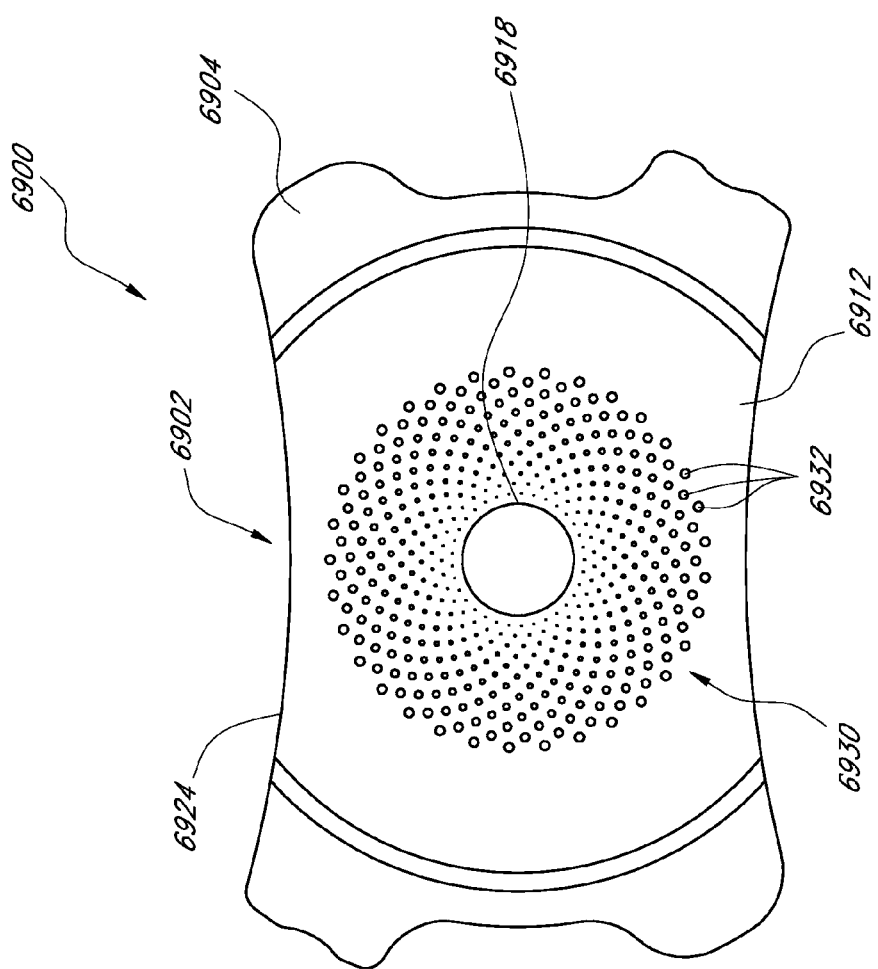
FIG. 58 is a top plan view of an embodiment of an intraocular implant with light transmission holes gradually increasing in size radially out from the aperture.

FIG. 58 illustrates another embodiment of an intraocular implant 6900 with a mask region 6930 with light transmission holes 6932. In certain embodiments, the intraocular implant 6900 is opaque in at least one region. For example, the mask region 6930 can be opaque. The light transmission holes 6932 can vary in size, density (e.g., number of holes per unit area) and/or surface area (e.g., percentage of surface area of light transmission holes 6932 compared to the total surface area of the mask region 6930) in one or more portions of the mask region 6930. For example, the size, density and/or surface area of the light transmission holes 6932 can increase or decrease radially from the inner periphery 6918 of the mask region 6930 to the outer periphery 6924 of the implant body 6902. The transition of the size and/or density of light transmission holes 6932 can be gradual or one or more steps. As illustrated in the embodiment in FIG. 58, the size of the light transmission holes 6932 gradually increase in size radially out from the aperture 6908 while the number of light transmission holes per unit area decreases. In certain embodiments, the light transmission holes 6932 have irregular spacing or have an irregular pattern.

Various embodiments have been described above. Although the invention has been described with reference to these specific embodiments, the descriptions are intended to be illustrative and are not intended to be limiting. Various modifications and applications may occur to those skilled in the art without departing from the true spirit and scope of the invention as defined in the appended claims.

What is claimed is:

1. An intraocular device comprising:
 a single, monofocal lens comprising an optically powered portion, the optically powered portion including a surface with a transition zone, the transition zone configured to reduce a thickness of the lens, measured from an anterior outer surface of the lens to a posterior outer surface of the lens, adjacent to the transition zone in a direction toward an optical axis of a recessed central region of the lens compared to a thickness of the lens, measured from the anterior outer surface of the lens to the posterior outer surface of the lens, adjacent to the transition zone in a direction toward the outer periphery of the lens; and
 a mask configured to block a substantial portion of light from passing through the transition zone so as to block a substantial portion of optical aberrations that would be created by light passing through the transition zone.

2. The intraocular device of claim 1, wherein the surface with the transition zone is a posterior surface of the lens.

3. The intraocular device of claim 1, wherein the surface with the transition zone is an anterior surface of the lens.

4. The intraocular device of claim 1, wherein an inner portion of the surface with the transition zone is convex, the transition zone is concave and an outer portion of the surface is convex, wherein the transition zone is adjacent the inner portion and the outer portion.

5. The intraocular device of claim 1, wherein an inner portion and an outer portion of the surface with the transition zone have a positive optical power, and the transition zone is adjacent the inner portion and the outer portion.

6. The intraocular device of claim 1, wherein the surface with the transition zone comprises an inner portion and an outer portion, and an outer perimeter of the inner portion is surrounded by an inner perimeter of the transition zone.

7. The intraocular device of claim 6, wherein an outer perimeter of the transition zone is surrounded by an inner perimeter of the outer portion.

8. The intraocular device of claim 1, wherein the surface with the transition zone comprises an inner portion and an outer portion, and a maximum thickness of the lens in a region of the inner portion is less than the maximum thickness of the lens in a region of the transition zone.

9. The intraocular device of claim 1, wherein the mask is between the surface with the transition zone and a second surface of the lens.

10. The intraocular device of claim 1, wherein the mask comprises an aperture and an opaque region adjacent the aperture.

11. The intraocular device of claim 10, wherein the aperture comprises a diameter of about 0.85 mm to about 1.8 mm.

12. The intraocular device of claim 11, wherein the mask comprises an outer diameter of about 3 mm to about 5 mm.

13. The intraocular device of claim 1, wherein the mask increases depth of focus of a patient.

14. The intraocular device of claim 1, further comprising a haptic attached to the lens to prevent the intraocular device from moving after being implanted within an eye.

15. The intraocular device of claim 1, wherein the mask comprises a plurality of holes characterized in that at least one of the hole size, shape, orientation, and spacing of the plurality of holes is varied to reduce the tendency of the holes to produce visible diffraction patterns.

16. The intraocular device of claim 1, further comprising a support member coupled to the mask and extending from the mask to an outer surface of the lens.

17. The intraocular device of claim 16, wherein the mask comprises a plurality of holes characterized in that at least one of the hole size, shape, orientation, and spacing of the plurality of holes is varied to reduce the tendency of the holes to produce visible diffraction patterns.

18. The intraocular device of claim 17, wherein the support member comprises a plurality of holes characterized in that at least one of the hole size, shape, orientation, and spacing of the plurality of holes is varied to reduce the tendency of the holes to produce visible diffraction patterns.

19. The intraocular device of claim 1, further comprising haptics coupled to the lens.

20. An intraocular device comprising:
a monofocal lens comprising a first surface and a second surface, the first surface comprising:
a first portion positioned at a central region of the first surface,
an annular second portion, and
an annular third portion positioned at an outer periphery of the first surface, the annular third portion positioned radially outward from the first portion,
wherein an optical axis of the lens passes through the first portion, and the annular second portion extends from the first portion to the annular third portion;
a mask positioned between the second surface and the annular second portion of the first surface; and
wherein the first surface comprises a single sloped portion such that the first portion is closer to the second surface than the third portion, the single sloped portion being the second portion.

21. The intraocular device of claim 1, wherein the transition zone reduces the thickness of the lens between 31% and 64%.

22. The intraocular device of claim 20, wherein the mask comprises a plurality of holes characterized in that at least one of the hole size, shape, orientation, and spacing of the plurality of holes is varied to reduce the tendency of the holes to produce visible diffraction patterns.

23. The intraocular device of claim 20, wherein the mask comprises an aperture and an opaque region adjacent the aperture.

24. The intraocular device of claim 1, wherein the mask is configured to block substantially all of the light passing through the transition zone.

25. The intraocular device of claim 1, wherein the surface with the transition zone includes an outer portion and an inner portion, and wherein the transition zone extends from the outer portion to the inner portion of the surface.

26. The intraocular device of claim 1, wherein the mask is spaced apart from the surface with the transition zone and positioned across the entire transition zone.

27. The intraocular device of claim 1, wherein the optically powered portion is configured to improve a patient's vision when the intraocular device is implanted in an eye.

28. The intraocular device of claim 1, wherein a non-reduced thickness of the lens is between 0.26 mm and 1.40 mm.

29. The intraocular device of claim 28, wherein the transition zone is configured to reduce the thickness of the lens between 31% and 64%.

* * * * *